US011065201B2

(12) United States Patent
Andresen et al.

(10) Patent No.: US 11,065,201 B2
(45) Date of Patent: Jul. 20, 2021

(54) GEL FORMULATIONS FOR LOCAL DRUG RELEASE

(71) Applicant: TECHNICAL UNIVERSITY OF DENMARK, Kgs. Lyngby (DE)

(72) Inventors: Thomas Lars Andresen, Vanløse (DK); Linda Maria Bruun, Fredriksberg (DK); Trine Bjørnbo Larsen, København N (DK); Rasmus Irming Jølck, Kgs. Lyngby (DK); Anders Elias Hansen, Bunkeflostrand (SE)

(73) Assignee: TECHNICAL UNIVERSITY OF DENMARK, Kgs. Lyngby (DK)

( * ) Notice: Subject to any disclaimer, the term of this patent is extended or adjusted under 35 U.S.C. 154(b) by 0 days.

(21) Appl. No.: 15/527,878

(22) PCT Filed: Nov. 20, 2015

(86) PCT No.: PCT/EP2015/077282
§ 371 (c)(1),
(2) Date: May 18, 2017

(87) PCT Pub. No.: WO2016/079330
PCT Pub. Date: May 26, 2016

(65) Prior Publication Data
US 2018/0325819 A1 Nov. 15, 2018

(30) Foreign Application Priority Data
Nov. 21, 2014 (SE) .................................. 1451411-1

(51) Int. Cl.
*A61K 9/06* (2006.01)
*A61K 47/26* (2006.01)
*A61K 9/00* (2006.01)

(52) U.S. Cl.
CPC .............. *A61K 9/06* (2013.01); *A61K 9/0024* (2013.01); *A61K 47/26* (2013.01)

(58) Field of Classification Search
CPC ............. A61K 9/00; A61K 9/06; A61K 47/26
See application file for complete search history.

(56) References Cited

U.S. PATENT DOCUMENTS

| 3,678,152 | A | 7/1972 | Bjork et al. |
| 3,763,226 | A | 10/1973 | Ingelman |
| 3,763,227 | A | 10/1973 | Ingelman |
| 3,804,892 | A | 4/1974 | Ingelman |
| 3,852,341 | A | 12/1974 | Lindberg et al. |
| 4,239,747 | A | 12/1980 | Pfeiffer et al. |
| 4,406,878 | A | 9/1983 | Deboer |
| 4,439,356 | A | 3/1984 | Khanna et al. |
| 5,066,580 | A | 11/1991 | Lee |
| 5,198,136 | A | 3/1993 | Tatemoto et al. |
| 5,356,635 | A * | 10/1994 | Raman ................. A61K 9/2013 424/423 |
| 5,371,109 | A * | 12/1994 | Engstrom ............ A61K 9/1274 514/769 |
| 5,750,409 | A | 5/1998 | Herrmann et al. |
| 6,008,379 | A | 12/1999 | Benson et al. |
| 6,352,722 | B1 * | 3/2002 | Blair ..................... A61K 9/145 424/464 |
| 6,413,536 | B1 | 7/2002 | Gibson et al. |
| 6,541,020 | B1 * | 4/2003 | Ding .................... A61K 9/0019 424/422 |
| 7,666,844 | B2 | 2/2010 | Buch-Rasmussen et al. |
| 7,871,383 | B2 | 1/2011 | Wiksell et al. |
| 2004/0162505 | A1 | 8/2004 | Kaplan et al. |
| 2004/0258698 | A1 * | 12/2004 | Wightman ............ A61K 47/50 424/178.1 |
| 2005/0036946 | A1 | 2/2005 | Pathak et al. |
| 2006/0148776 | A1 * | 7/2006 | Ulm ...................... A61K 31/33 514/183 |
| 2009/0110644 | A1 | 4/2009 | Margel et al. |
| 2010/0290995 | A1 | 11/2010 | Pathak et al. |
| 2010/0297007 | A1 | 11/2010 | Lanza et al. |
| 2012/0065614 | A1 | 3/2012 | Omary et al. |

FOREIGN PATENT DOCUMENTS

| CN | 102762528 A | 10/2012 |
| EP | 0023992 B1 | 6/1982 |
| EP | 0049745 B1 | 11/1984 |

(Continued)

OTHER PUBLICATIONS

Xiaoli et al., "Injectable Long-Acting in Situ Forming Systems for Radix Ophiopogonis Polysaccharide", International Journal of Biological Macromolecules, Elsevier BV, NL, vol. 72, pp. 553-559, Sep. 16, 2014.
Jølck et al., "Injectable Colloidal Gold in a Sucrose Acetate Isobutyrate Gelating Matrix with Potential Use in Radiation Therapy", Advanced Healthcare Materials, vol. 3, Issue 10, pp. 1680-1687, Oct. 1, 2014.
International Search Report dated Apr. 20, 2016 for PCT Application No. PCT/EP2015/077282.
Chiellini et al., "Biomedical Polymers and Polymer Therapeutics", Springer, pp. 470, 2001.

(Continued)

*Primary Examiner* — Michael G. Hartley
*Assistant Examiner* — Jagadishwar R Samala
(74) *Attorney, Agent, or Firm* — Moser Taboada

(57) ABSTRACT

The present invention relates to a composition comprising non-water soluble carbohydrates, wherein at least 50% of the non-water soluble carbohydrates are carbohydrates selected from derivatives of lactose, maltose, trehalose, raffinose, glucosamine, galactosamine, lactosamine, or derivatives of disaccharides with at least two pyranose saccharide units, trisaccharides, tetrasaccharides, or mixtures thereof, and wherein the composition is a liquid before administration into the human or animal body and increases in viscosity by more than 1,000 centipoise (cP) after administration, for use as a medicament.

21 Claims, 46 Drawing Sheets

(56) References Cited

FOREIGN PATENT DOCUMENTS

| | | |
|---|---|---|
| EP | 0108638 B1 | 7/1986 |
| EP | 0686046 B1 | 5/2000 |
| EP | 1042339 B1 | 3/2003 |
| EP | 1173151 B1 | 7/2003 |
| EP | 1189305 A3 | 8/2003 |
| EP | 1006935 B1 | 1/2005 |
| EP | 1212092 B1 | 10/2005 |
| EP | 2518040 A1 | 10/2012 |
| JP | 2001516728 A | 10/2001 |
| SE | 403255 B | 8/1978 |
| WO | WO-9208691 A1 | 5/1992 |
| WO | WO-9403155 A1 | 2/1994 |
| WO | WO-9519184 A1 | 7/1995 |
| WO | WO-9700240 A1 | 1/1997 |
| WO | WO-9913913 A2 | 3/1999 |
| WO | WO-9933853 A2 | 7/1999 |
| WO | WO-0026179 A1 | 5/2000 |
| WO | WO-0115734 A2 | 3/2001 |
| WO | WO-0162296 A2 | 8/2001 |
| WO | WO-0232914 A2 | 4/2002 |
| WO | WO-03080554 A3 | 4/2004 |
| WO | WO-2009071605 A1 | 6/2009 |
| WO | WO 2013/067597 * | 5/2013 |

OTHER PUBLICATIONS

Hindenlang et al., "Iodine-containing radio-opaque polyphosphazenes", The Royal Society of Chemistry, Polymer Chemistry, vol. 1, pp. 1467-1474, 2010.

Japanese Office Action on Patent Application No. 2017-526555, dated Aug. 30, 2019.

* cited by examiner

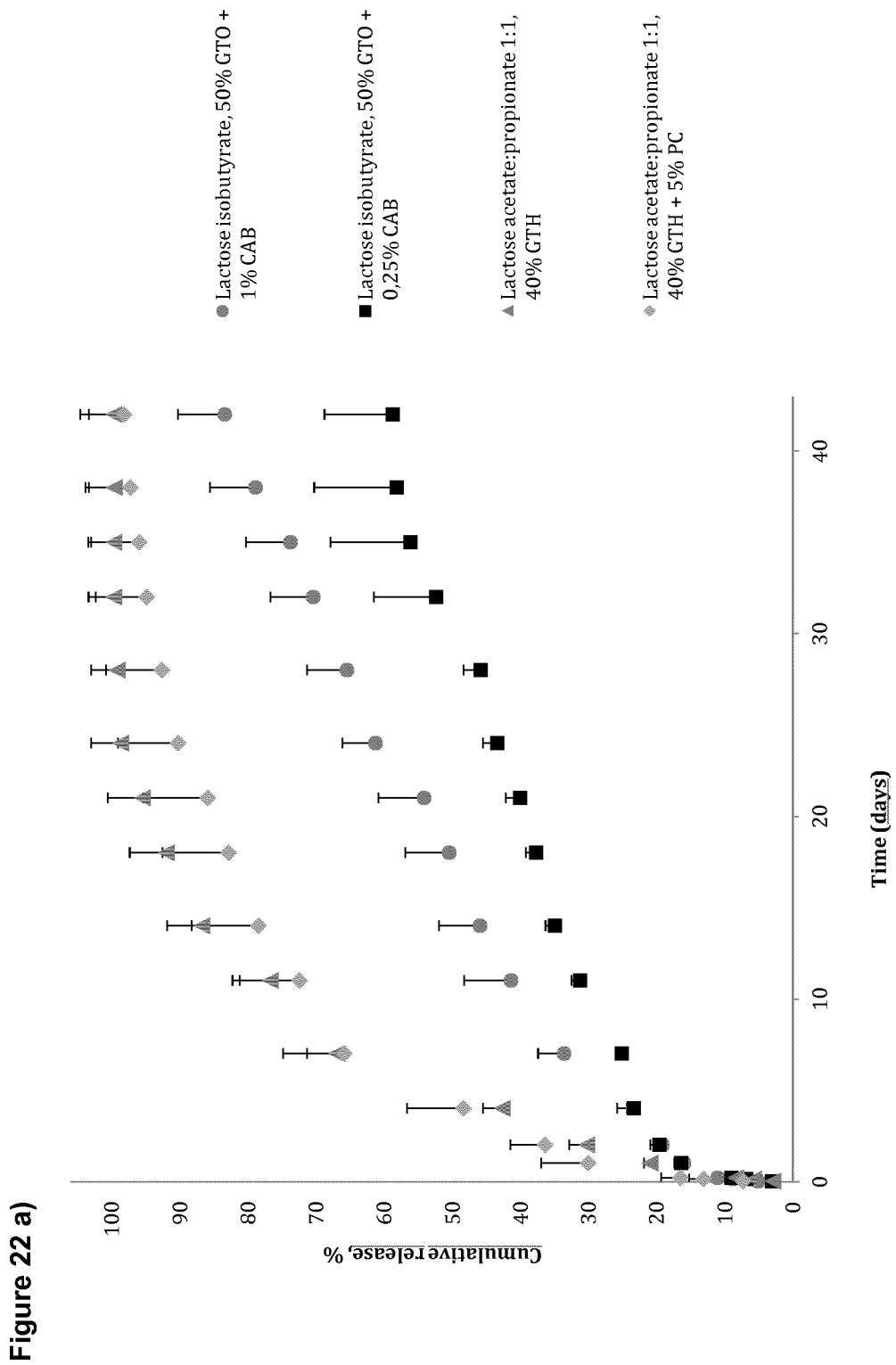

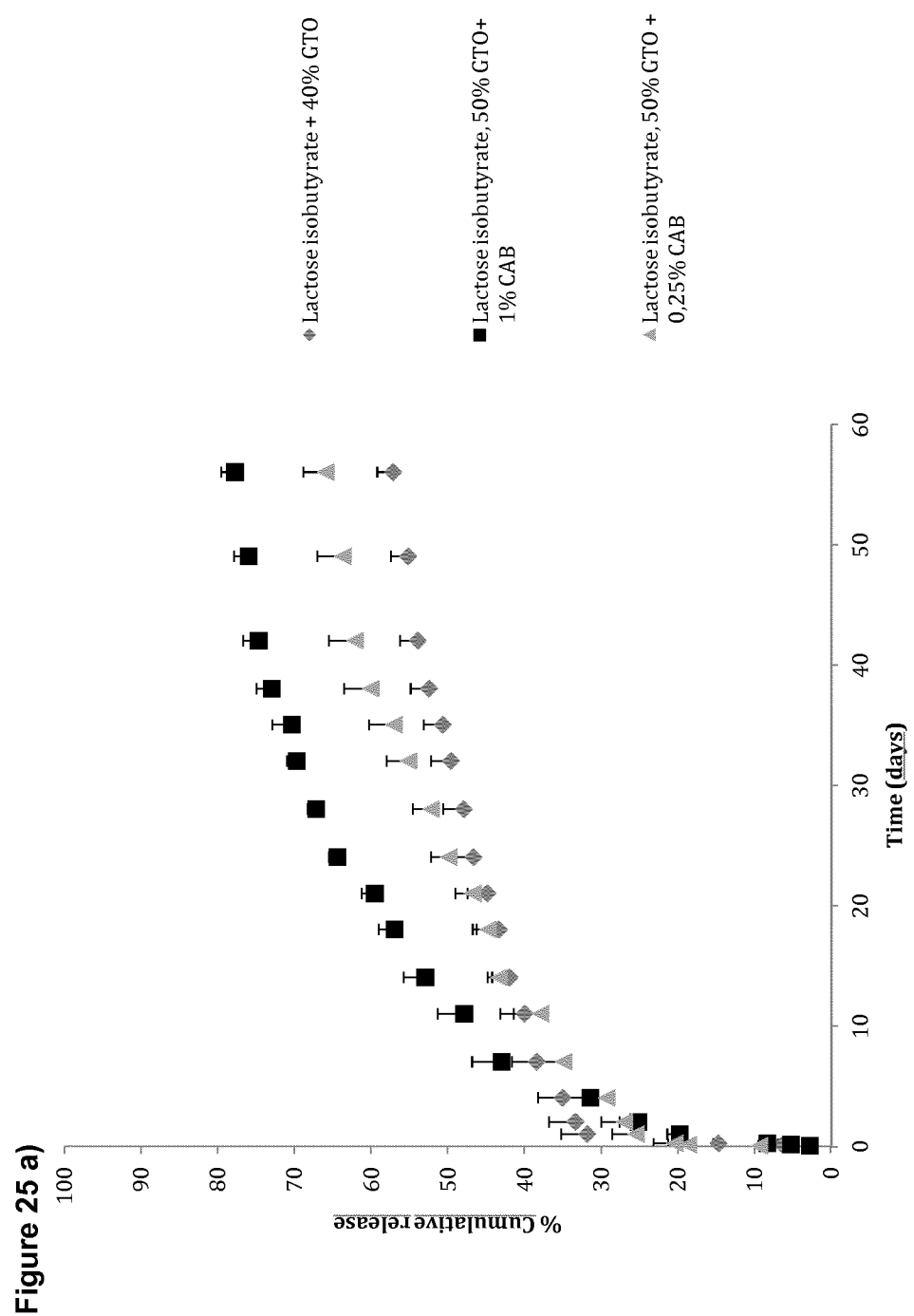

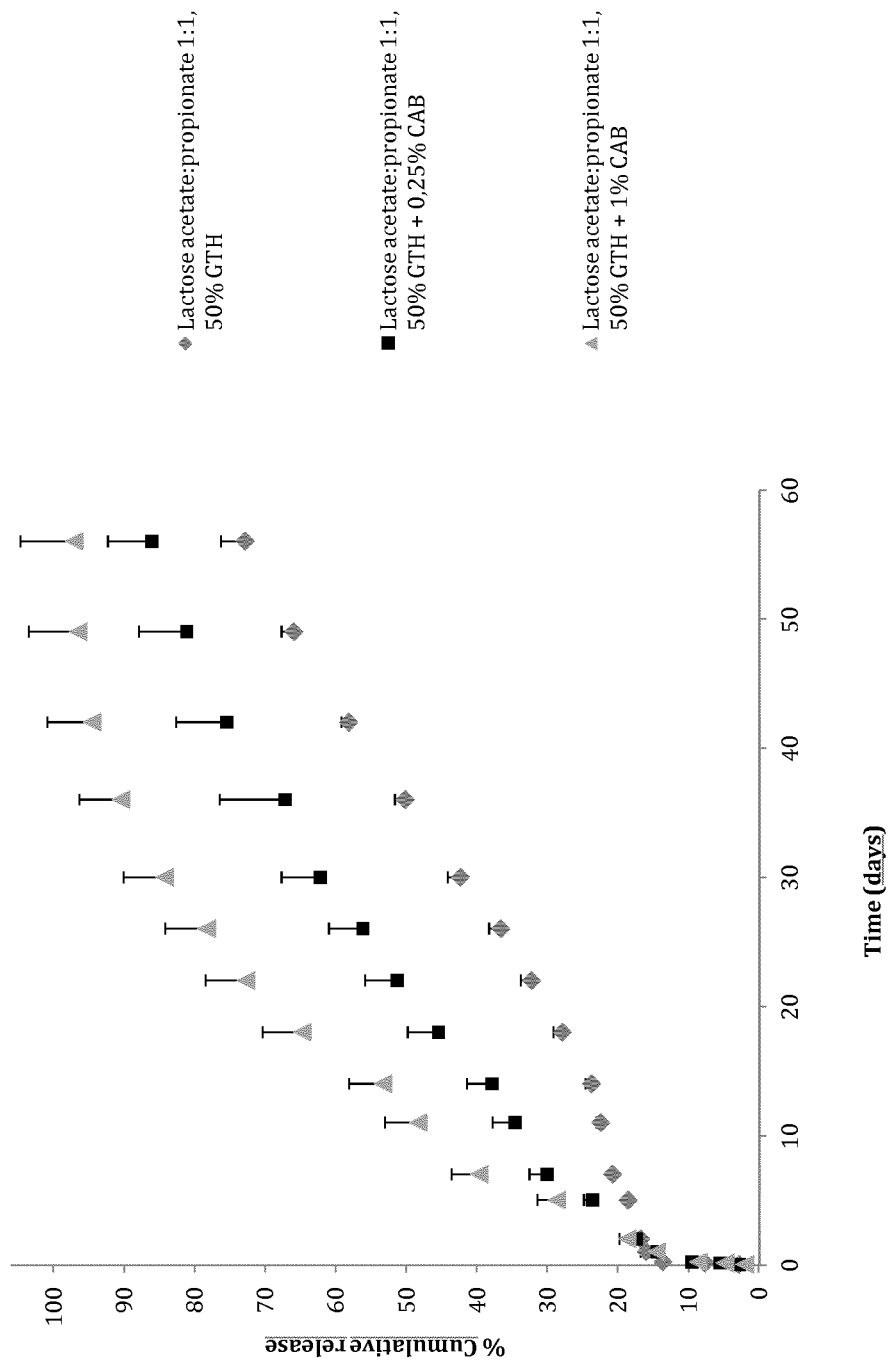
Figure 27 b1)

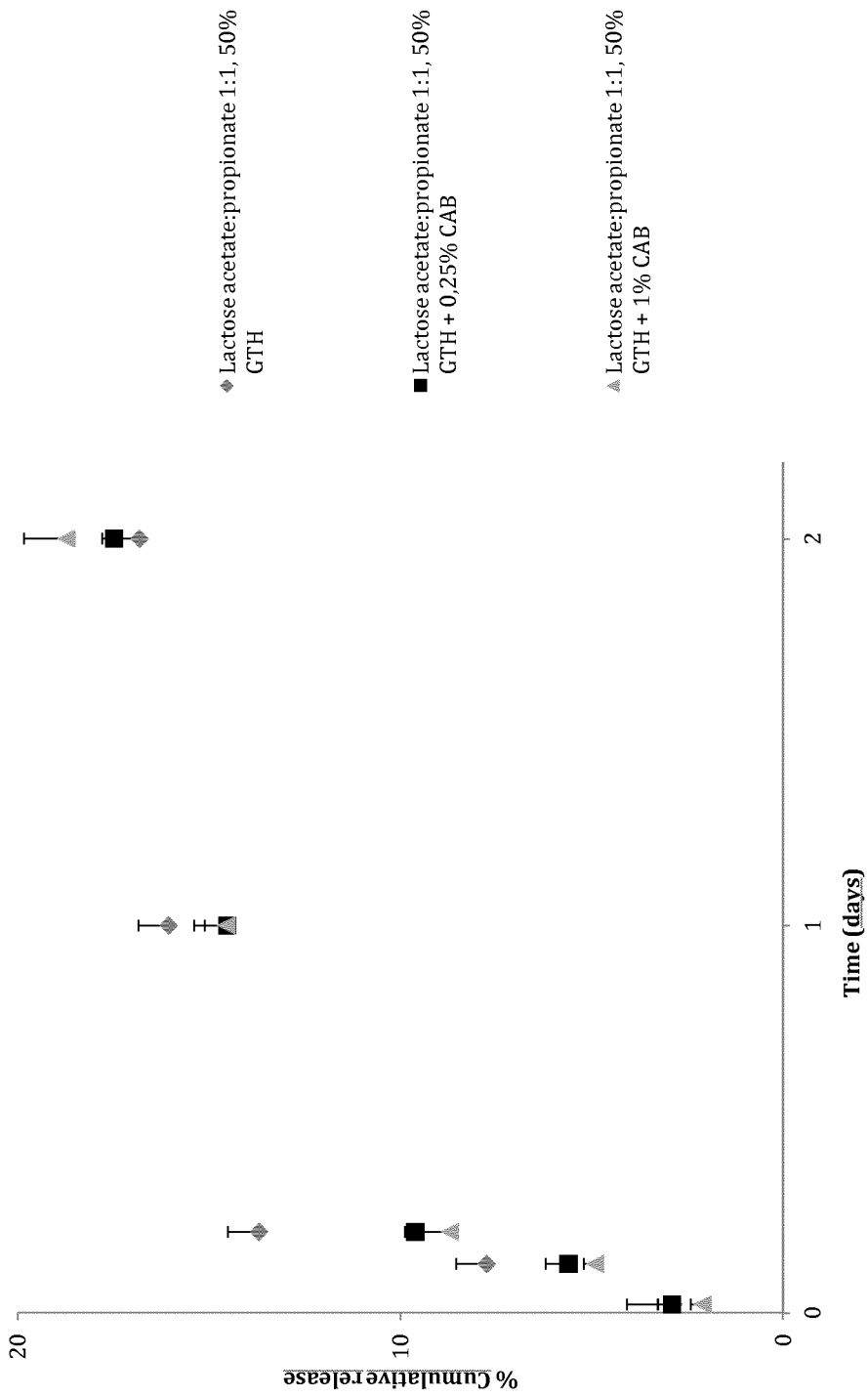
Figure 27 b2)

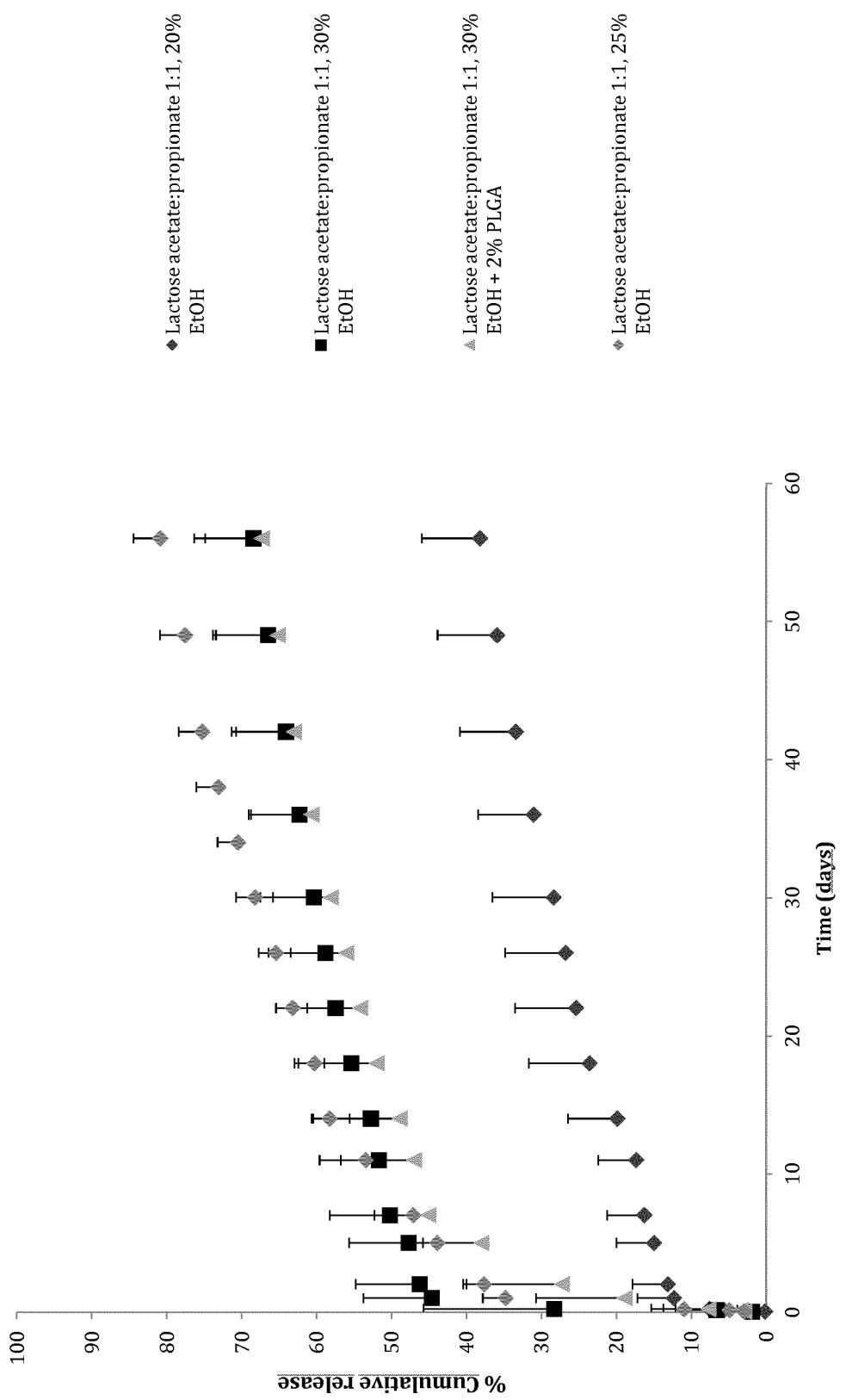

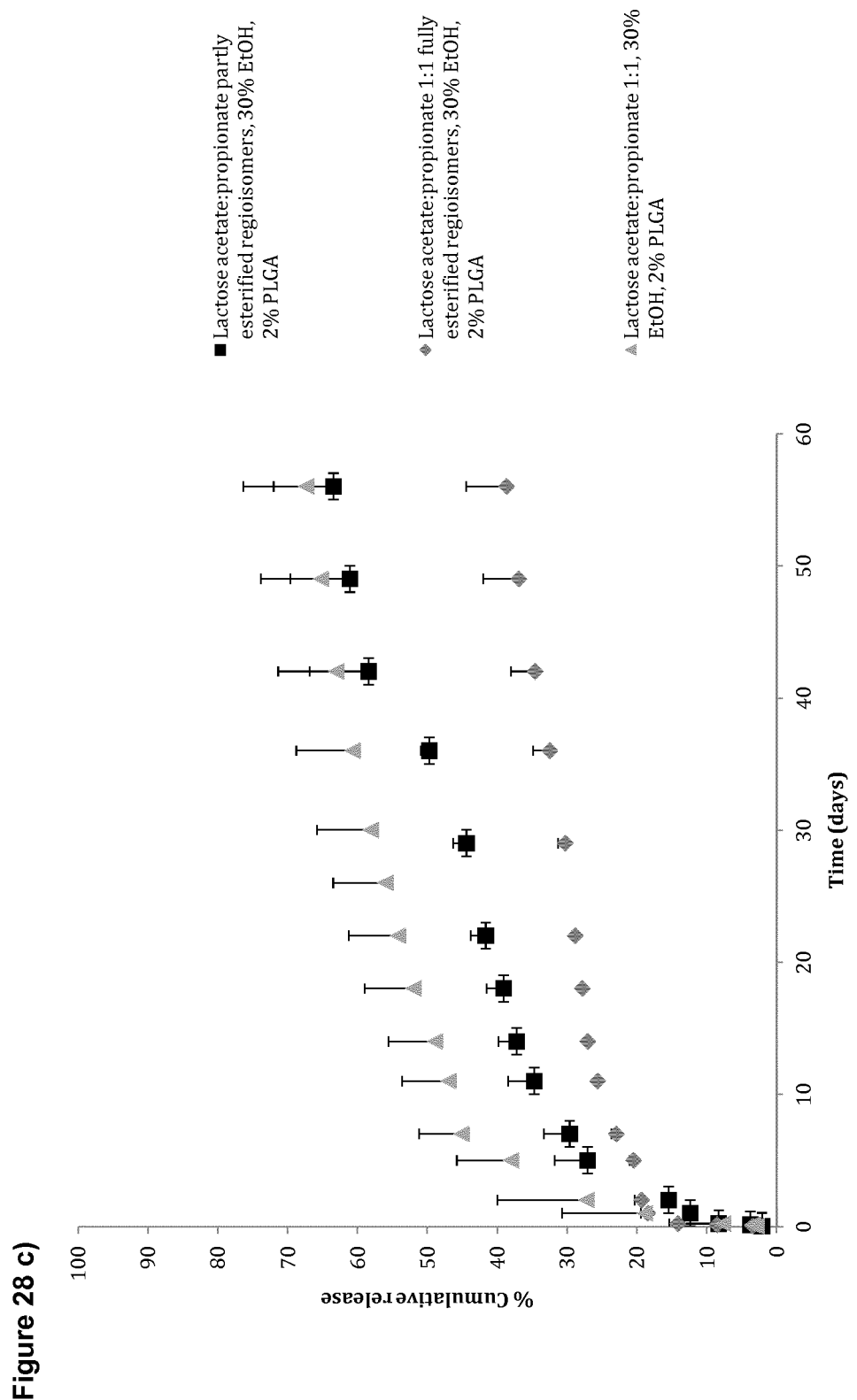

GEL FORMULATIONS FOR LOCAL DRUG RELEASE

FIELD OF THE INVENTION

The present invention provides controlled release of drugs from gel formulations for treatment of disease.

TECHNICAL BACKGROUND

Biomaterials for use as drug delivery systems have found wide interest for treatment of multiple diseases and conditions in humans and animals, such as pain, inflammation, infection, allergy, and cancer. Advanced imaging techniques are furthermore important to diagnose patients and guide advanced treatments such as surgery and radiotherapy and new contrast agents and biomaterials to guide such procedures are of great importance. The present invention provides injectable liquids that gels or solidifies after administration to human or animal body after which it provides a system for controlled drug release and/or acts as a tissue marker for imaging by one or multiple imaging modalities.

Other patents and articles have described the use of biomaterials for controlled release of drugs for various applications. EP1212092 and U.S. Pat. No. 6,413,536 describe formulations for drug delivery based on a hydrophobic gel matrix consisting of organic solvent, a saccharide ester based on sucrose derivatives such as SAIB or other poly-ols and one or several drugs. EP1173151B1 and U.S. Pat. No. 7,666,844 describes injectable micro-implants for intramuscular or subcutaneous injection of hormones, antidiabetic drugs, growth factors, and blood factors. The injectable formulations are based on derivatized carbohydrates. The needle formed solid micro-implants are thought to be so small, that they can be injected by the patient him/herself by some manual device. EP1042339 and U.S. Pat. No. 6,352,722 describes isomers of derivatives of sucrose, lactose, cellobiose and trehalose for drug delivery. In this patent, the medicinal molecules are incorporated in a solid carbohydrate matrix by either mixing it with solvent following evaporation or by melting the carbohydrates and then mixing them with the drug, which results in a solid matrix to be administered to the patient. Every year more than 12 million people are diagnosed with cancer worldwide and over 7.5 million people die from cancer each year. These numbers are expected to increase because of population growth and due to the lifestyle in the Western world. There are four standard treatments of cancer; surgery, chemotherapy, radiotherapy and immunotherapy, which can be combined to provide treatment benefit for patients. Radiotherapy is an important part of modern cancer treatment and more than 50% of cancer patients receive radiotherapy at least once. Modern radiotherapy relies on advanced high precision planning, treatment equipment and imaging techniques (such as, e.g., computed tomography (CT), positron-emission tomography (PET) and magnetic imaging resonance (MRI)) in order to deliver high radiation doses to a precisely defined target in patients. Newer treatment regimes include photodynamic therapy, high intensity ultrasound therapy, and methods for thermal ablation to create tissue damage.

One of the main difficulties in external beam radiotherapy and other therapies that rely on external energy delivery to tissues is that both tumors and other tissue move significantly and unpredictably during radiation; both within each single treatment, and during the whole course of treatment. These movements can be dramatic (e.g. several cm within seconds) and may be caused by various factors such as respiration, bladder- and bowel filling, air passing colon, tumor shrinkage and set-up variation of the patient. One way of minimizing this problem is the implantation of markers in or adjacent to the tumor allowing frequent imaging and treatment adaptation.

Ideally, a tissue marker should enable tracking of tissue movement; be visible on several image modalities; be visible for an extended period (e.g., at least 4 weeks); be non-toxic; and be easy to insert.

Various attempts have been made for improvements within the field of radiotherapy. EP1006935 describes a composition for controlled release of a substance WO9403155 describes a hydrogel composition prepared from a backbone bonded to a cross-linking agent. The hydrogels may be loaded with therapeutic drugs and diagnostic labels, including X-ray contrast imaging agents for disease diagnostics and treatment. US20120065614 discloses a hybrid system for bio imaging. Gold is bound into a matrix comprising a hydrogel or polymer or similar. In US20100297007 a substantially bi concave shaped nanoparticle is disclosed, the nanoparticle comprising an aqueous inner core and a hydrophilic outer shell comprising an amphiphilic polymer.

Furthermore, US2009110644 discloses a nanoparticle consisting of a polymer which is a metal chelating agent coated with a magnetic metal oxide, wherein at least one active agent is covalently bound to the polymer. In the documents US20100290995 and US2005036946, radiopaque biodegradable compositions are disclosed by modifying terminal groups of synthetic and natural biodegradable polymers such as polylactones with iodinated moieties and in SE403255 a contrast agent is disclosed that comprises a polymer comprising hydroxy- and/or carboxy- and/or amino groups further comprising X-ray contrast giving iodo-substituted aromatic groups. Further yet, the document WO 9519184 discloses air encapsulating micro particles formed by ionotropically gelling synthetic polyelectrolytes such as poly(carboxylato-phenoxy)phosphazene, poly(acrylic acid), poly(methacrylic acid) and methacrylic acid copolymers (Eudragit's) by contact with multivalent ions such as calcium ions.

There are several drawbacks to the current clinical practice using solid markers and the methods described in the documents above. Installation of solid markers is invasive due to the large dimension of the solid implant which may cause severe complications limiting is usefulness in radiotherapy. By combining gel-forming, low-viscosity solutions with solid particles and/or organic X-ray contrast agents (or other imaging modalities) injectable gels can be formulated with fine-tuned properties as these can be modified by multiply parameters with respect to the gel forming solution and the contrast agents used. The solid particles can, besides contributing to the overall contrast of the system, also carry pharmaceutical substances and control their release in a controlled manner.

Unfortunately, radiotherapy is only able to provide local control of the primary tumor and is not suitable for treating patients with metastatic disease. However, by utilizing the weak immune stimulating effects that radiotherapy provides, in combination with potent immune modulating drugs, it may be possible to cure patients with metastatic disease and obtain systemic tumor control. Cancer immunotherapy attempts to stimulate the immune system to reject and destroy tumors. Radiotherapy (RT) induces tumor cell death by several mechanisms, one represented by induction of immunogenic cell death that leads to secretion of immunogenic proteins like Calreticulin and HMGB1, and small molecules like ATP. These factors activate antigen-presenting cells like monocytes, dendritic cells (DC) and macrophages in the tumor microenvironment. Furthermore, the cells phagocytose dead tumor cells and cell components, and migrate to local lymph nodes to raise an antigen specific response against antigens from the resident dead tumor cells. Unfortunately, radiation alone does not induce a sufficiently high immunogenic response to provide a specific immunodependent eradication of the cancer cells due to the immunosuppressive environment, systemically as well as locally in the tumors. An effect caused by M2 macrophages, Treg-cells, immature DCs and myeloid derived suppressor cells. However, a combination of radiotherapy with administered Toll Like Receptor (TLR) agonists or other immune stimulating compounds can potentially provide a sufficiently high immune cell activation to induce a highly effective systemic response.

The combination of radiotherapy with chemotherapeutic drugs or radiosensitizers is also highly interesting for combination therapies if efficient drug delivery systems were available.

One aim of the present invention is to provide new formulations comprising gel-forming, low-viscosity systems that are easy to administer parenterally, and wherein the present invention provides good control of drug release and potentially also visualization by one or multiple imaging modalities.

SUMMARY OF THE INVENTION

The present invention relates to a composition comprising non-water soluble carbohydrates, wherein at least 50% of the non-water soluble carbohydrates are carbohydrates selected from derivatives of lactose, maltose, trehalose, raffinose, glucosamine, galactosamine, lactosamine, or derivatives of disaccharides with at least two pyranose saccharide units, trisaccharides, tetrasaccharides, or mixtures thereof, and wherein the composition is a liquid before administration into the human or animal body and increases in viscosity by more than 1,000 centipoise (cP) after administration, for use as a medicament.

DESCRIPTION OF THE DRAWINGS

FIG. 22 b): Release of Tirapazamine from lactose acetate:propionate 1:1 and lactose isobutyrate-triglyceride formulations with and without 5-15% propylene carbonate or 1-0.25% cellulose acetate butyrate (Mn~12.000).

FIG. 25 b): Release of 5-FU from lactose acetate:propionate 1:1 or lactose isobutyrate-triglyceride formulations.

FIG. 26 b): Release from high concentration 5-FU lactose isobutyrate gel formulations.

FIG. 26 c): Release from high concentration 5-FU lactose isobutyrate gel formulations.

FIG. 26 d): Release from high concentration 5-FU lactose isobutyrate gel formulations.

FIG. 27 b1): Release from high concentration 5-FU lactose acetate:propionate 1:1 gel formulations.

FIG. 27 b2): Release from high concentration 5-FU lactose acetate:propionate 1:1 gel formulations.

FIG. 27 c): Release from high concentration 5-FU lactose acetate:propionate 1:1 gel formulations.

FIG. 27 d): Release from high concentration 5-FU lactose acetate:propionate 1:1 gel formulations.

FIG. 28 b): Release of 5-FU from lactose acetate:propionate regioisomer-triglyceride/EtOH formulations.

FIG. 28 c): Release of 5-FU from lactose acetate:propionate regioisomer-triglyceride/EtOH formulations.

DETAILED DESCRIPTION OF THE INVENTION

Figure 1:
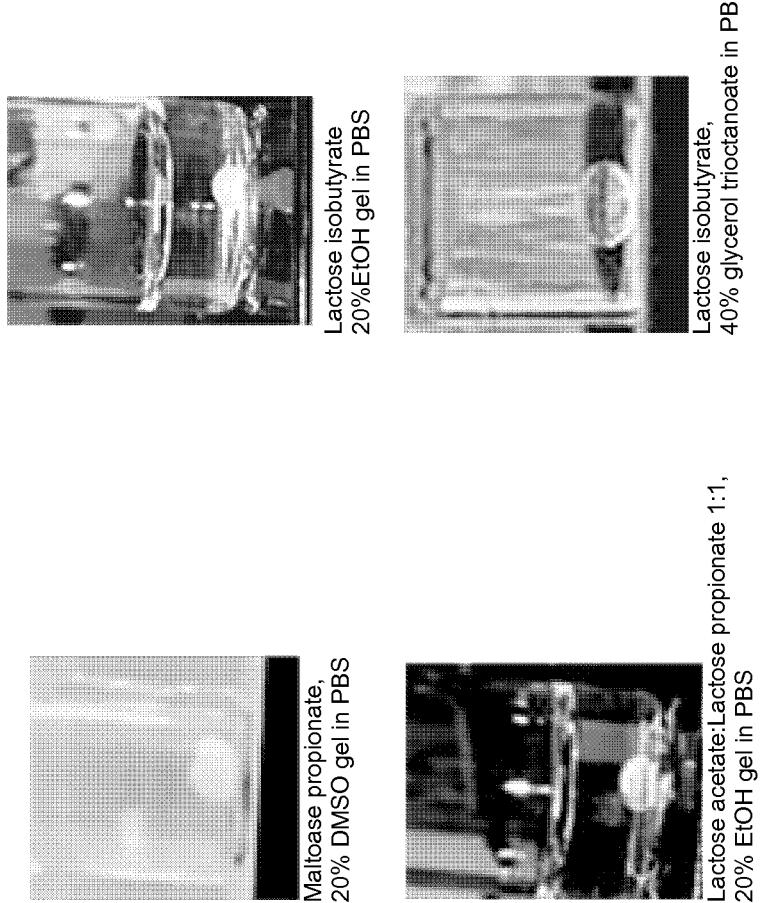
FIG. 1: In vitro studies of gel forming systems comprised of non-water soluble carbohydrates

The present invention discloses a composition comprising non-water soluble carbohydrates, wherein at least 50% of the non-water soluble carbohydrates are carbohydrates selected from derivatives of lactose, maltose, trehalose, raffinose, glucosamine, galactosamine, lactosamine, or derivatives of disaccharides with at least two pyranose saccharide units, trisaccharides, tetrasaccharides, or mixtures thereof, and wherein the composition is a liquid before administration into the human or animal body and increases in viscosity by more than 1,000 centipoise (cP) after administration, for use as a medicament.

Definitions

"Non-water soluble carbohydrates" refers to carbohydrates that are insoluble in water, which is defined as carbohydrates that precipitates when the concentration exceeds 0.1 M at 25 degrees Celsius.

In the context of the present invention, a "gel" is defined as a carrier matrix in which the detectable agent (contrast agent) or active pharmaceutical ingredient is dispersed and/or dissolved within. The term "gel" as used in the present invention includes systems such as gels or amorphous glass matrices, crystalline solids, amorphous solids, which upon injection into a human or an animal increases viscosity where the composition changes from being liquid like to gel like in its appearance.

In the context of the present invention, a "marker" or "tissue marker" is a detectable agent or composition which does not move, or stays substantially in the same position, for several days or weeks once it has been administered or implanted into a specific site or tissue of a mammalian body. A tissue marker can, for example, comprise one or more X-ray contrast agents, radioactive compounds, paramagnetic compounds, fluorescent agents, ultrasound contrast agent, agents visible with PET imaging, or other detectable agents.

An "imageable tissue marker" or "imageable marker" comprises a detectable agent in a form and/or a sufficient amount to allow for detection of the tissue marker by an external imaging modality if administered or implanted into a mammalian body. Exemplary external imaging modalities include, but are not limited to, X-ray imaging, CT imaging, MRI, PET imaging, single photon emission computed tomography (SPECT) imaging, nuclear scintigraphy imaging, ultrasonography imaging, ultrasonic imaging, near-infrared imaging and/or fluorescence imaging.

With the term "carbohydrates", as used herein, we refer to monosaccharides, disaccharides and trisaccharides or oligosaccharides, including amino sugars.

With the term "hydrofobicity" we refer to the effect that molecule is seemingly repelled from water, which means that it has a very low solubility in water.

With the term "viscosity" we refer to that the viscosity of a fluid is a measure of its resistance to gradual deformation by shear stress or tensile stress With the term "gel-like" compound or material, as used herein, we refer to any compound comprising some of the properties of a gel i.e. a material that exhibits limited flow when in the steady-state. By weight, gels are mostly liquid, yet they behave like solids due to a three-dimensional interactions within the liquid. It is the interactions within the fluid that gives a gel its structure (hardness) and contributes to the adhesive stick. In this way gels are a dispersion of molecules of a liquid within a solid in which the solid is the continuous phase and the liquid is the discontinuous phase providing a gel-like material with a higher viscosity than for that of a liquid.

The terms "drug", "medicament", "agent", or "pharmaceutical agent" as used herein include, biologically, physiologically, or pharmacologically active substances that act locally or systemically in the human or animal body.

The terms "treating", "treatment" and "therapy" as used herein refer equally to curative therapy, prophylactic or preventative therapy and ameliorating therapy. The term includes an approach for obtaining beneficial or desired physiological results, which may be established clinically. For purposes of this invention, beneficial or desired clinical results include, but are not limited to, alleviation of symptoms, diminishment of extent of disease, stabilized (i.e., not worsening) condition, delay or slowing of progression or worsening of condition/symptoms, amelioration or palliation of the condition or symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering compositions of the present invention.

DETAILED DESCRIPTION OF THE INVENTION

The formulation is preferably in the form adapted for parenteral administration and/or for administration using topical route, and/or for administration using intracavitary routes such as bladder, uterus, and vagina, and should preferably consist of pharmaceutically acceptable constituents. The formulation that as such has a comparable low viscosity is intended for injection in the body of a human or animal, where after the formulation becomes more viscous, i.e. it goes through a sol-gel transition (liquid to gel) transition, due to the presence of the gel-forming system. It is preferred that the viscosity of the formulation after injection in the body of a human or animal increases by at least 50%, such as at least 80%, such as at least 100%, or at least 150%, or at least 200%, or at least 300%, or at least 500%, or at least 750%, or at least 1000%, or at least 10,000%, or that the formulation becomes essentially solid (non-viscous).

The formulation is preferably adapted for injection via a thin needle used for injection into a body or surgical related procedures, such as but not limited to biopsy. The viscosity of the gel-forming formulation before injection can be any suitable viscosity such that the formulation can be parenterally administered to a patient.

Exemplary formulations include, but are not limited to, those having a viscosity (prior to administration/injection) lower than 10,000 centipoise (cP), e.g. lower than 2,000 cP, such as 10 to 2,000 cP, such as 20 to 1,000 cP, such as 150 to 350 cP, such as 400 to 600 cP, such as 600 to 1,200 cP or such as 1,000 to 2,000 cP, or 10 to 600 cP, or 20 to 350 cP, at 20° C. Alternative formulations include, but are not limited to, those having a viscosity (prior to administration/injection) lower than 10,000 centipoise (cP), e.g. lower than 2,000 cP, such as 10 to 2,000 cP, such as 20 to 1,000 cP, such as 150 to 350 cP, such as 400 to 600 cP, such as 600 to 1,200 cP or such as 1,000 to 2,000 cP, or 10 to 600 cP, or 20 to 350 cP, at 5° C. When referred to herein, the (dynamic) viscosity is measured at the specified temperature in accordance with the method described in ASTM D7483. Gels in the present invention are formed by hydrophobic interactions and/or physical (non-covalent) cross-links by complexation, hydrogen bonding, desolvation, Van der Waals interactions, ionic bonding, combinations thereof, and the like, and may be initiated by mixing two precursors that are physically separated until combined in situ, or as a consequence of a prevalent condition in the physiological environment. Chemical (covalent) cross linking may be accomplished by any of a number of mechanisms, including free radical polymerization, condensation polymerization, anionic or cationic polymerization, step growth polymerization, electrophile-nucleophile reactions, combinations thereof, and the like.

The gel forming compositions may be loaded with organic x-ray agents such as iodinated polymers or sugars and nanoparticles or submicron particles either prior to or during gel formation, such as when the gel is in a liquid state or in transition to the gel-state, e.g., by diffusion into the gel composition. These x-ray agents or particles may either be entrapped in the hydrogel matrix without any chemical bond, or they may be bonded, non-covalently or covalently, to the gel composition. The organic x-ray agents may be one component in the gel and the particles another component, where the particles are either a contrast agent for imaging by x-ray, MRI, PET, SPECT, fluorescence, proton radiation or ultrasound including HIFU, and/or contain pharmaceutical agents. Pharmaceutical agents may be, but not limited to, radiosensitzers, chemotherapeutics, immunomodulators, anesthetics or hormones. MRI agents such as gadolinium may be a component in the gel forming systems. Pharmaceutical agents can furthermore be covalent or non-covalently embedded in the gel. After injection, the gelled or solidified formulation typically provides a well defined gel that remains at the injection site for several days, weeks or months and may contain an assembly of imaging contrast agents which provides contrast in e.g. X-ray imaging, and which may serve as a tissue marker, thus, enabling tracking of tissue or tumor movement during e.g. radiotherapy or surgical procedures.

The gel forming system may be used for aid or guidance of one or more external or internal stimuli (or a combination of both). It may also be used in combination with external or internal stimuli to enhance the therapeutic effect of the stimuli. In one interesting embodiment, the gel forming system may be used in combination with photodynamic therapy (PDT) in combination with a drug (photosensitizer or photosensitizing agent) with a specific type of light to kill cancer cells. In another embodiment, the gel forming system may be used in combination with hyperthermia based treatments such as high-intensity focused ultrasound (HIFU), radiofrequency thermal ablation (RFA) and laser-induced interstitial thermotherapy (LITT), but not limited to those. In high-intensity focused ultrasound (HIFU) the gel forming system may be used to direct or aid in delivery of acoustic energy into the desired tissue thereby destroying the diseased tissue by e.g. thermal ablation (coagulation necrosis). In another embodiment, the gel forming system may be used to direct or aid in insertion of the needle electrode into the target site for use in radiofrequency thermal ablation (RFA). In yet another embodiment, the gel forming system may be used to direct or aid in Laser-induced interstitial thermotherapy (LITT) to ensure correct laser irradiation of the target tissue.

Gel Forming Component

Suitable gel-forming components include those composed of organic constituents such as derivatized saccharides such as esterified saccharides, derivatized polyols such as esterified polyols, polymers, lipids, peptides, proteins, low molecular weight gelators and non-water soluble high-viscosity liquid carrier materials as well as combinations hereof.

In one specific embodiment of the invention the hydration sensitive gel forming component is hydrophobic saccharides. Preferred scaffolds are monosaccharides, disaccharides, trisaccharides, or oligosaccharides. Other suitable alcohol moieties include those derived by removing one or more hydrogen atoms from: monofunctional C1-C20 alcohols, difunctional C1-C20 alcohols, trifunctional alcohols, hydroxy-containing carboxylic acids, hydroxy-containing amino acids, phosphate-containing alcohols, tetrafunctional alcohols, sugar alcohols, monosaccharides, and disaccharides, sugar acids, and polyether polyols. More specifically, alcohol moieties may include one or more of: dodecanol, hexanediol, more particularly, 1,6-hexanediol, glycerol, glycolic acid, lactic acid, hydroxybutyric acid, hydroxyvaleric acid, hydroxycaproic acid, serine, ATP, pentaerythritol, mannitol, sorbitol, glucose, galactose, fructose, maltose, lactose, glucuronic acid, polyglycerol ethers containing from 1 to about 10 glycerol units, polyethylene glycols containing 1 to about 20 ethylene glycol units. Additionally, any oligosaccharide containing from 3 to about 6 monosaccharides may be used as the scaffold in the present invention. In general, the scaffold esters of the invention can be made by reacting one or more alcohols, in particular one or more polyols, which will form the alcohol moiety of the resulting esters with one or more carboxylic acids, lactones, lactams, carbonates, or anhydrides of the carboxylic acids which will form the acid moieties of the resulting esters. The esterification reaction can be conducted simply by heating, although in some instances addition of a strong acid or strong base esterification catalyst may be used. Alternatively, an esterification catalyst such as stannous 2-ethylhexanoate or activation reagents such as N-(3-Dimethylaminopropyl)-N'-ethylcarbodiimide (EDC), N,N'-Dicyclohexylcarbodiimide (DCC), O-(7-azabenzotriazol-1-yl)-N,N,N',N'-tetramethyluronium hexafluorophosphate (HATU) and the like can be used.

The acyl groups forming the acyloxy substituents of the invention may be any moiety derived from a carboxylic acid. More particularly, the acyl groups of the compositions of the invention may be of the RCO—, where R is optionally oxy-substituted alkyl of 2-10 carbon atoms which may be linear or branched hydrocarbons with one or more functional groups present in the chain. Using carboxylic acids and/or polyols of different chain length and using carboxylic acids having oxy-substitution allows control of the degree of hydrophilicity and of the solubility of the resulting ester. Such materials are sufficiently resistant to dissolution in vivo that they are able to form stabile hydrophobic gels, which may encapsulate the acitive pharmaceutical ingredients and/or the contrast agents of the present invention.

Suitable monosaccharides in either D or L-form include but are not limited to the following structures, in which α,β anomeric mixtures at any ratio may exist: Glucosamine, Galactosamine, Mannosamine, Mannose, Rhamnose, Rhamnosamine, Galactose, Allose, Allosamine, Altrose, Altrosamine, Gulose, Gulosamine, Idose, Idosamine, Talose and Talosamine.

Suitable disaccharides, include but are not limited to the following structures in which α,β anomeric mixtures at any ratio may exist, and where the individual sugars may be linked by either α or β glycosidic bonds and the individual sugars can D or L: Galp-(1→2)-Glc, Galp-(1→3)-GlcN, Galp-(1→4)-Glc, Glcp-(1→4)-Glc, Glcp-(1→6)-Glc, Glcp-(1→2)-GlcN, Galp-(1→4)-ManN, Glcp-(1→4)-GalN, Manp-(1→3)-Glc, ManNp-(1→4)-Gal, GalNp-(1→3)-ManN, GlcNp-(1→6)-GalN, Rhamnp-(1→6)-Glc, Glcp-(1↔1)-Glcp, Talp-(1→4)-Glu, Glup (1→3)-Ido, GlcAlp-(1→4)-GlcN, GlcAlp-(1→6)-GlcN.

Suitable trisaccharides include but are not limited to the following structures in which α,β anomeric mixtures at any ratio may exist, and where the individual sugars can be linked by either α or β glycosidic bonds and the individual sugars can be D or L: Galp-(1→2)-Glcp-(1→3)-Galp, Galp-(1→4)-Glcp-(1→6)-GlcN, Galp-(1→4)-Glcp-(1→6)-Gal, Glcp-(1→4)-Glcp-(1→4)-Glcp, Glcp-(1→6)-Glcp-(1→6)-Glc, Galp-(1→6)-Glcp (1↔2)-Fruf, Glcp-(1→3)-Fruf-(2↔1)-Glcp, Galp-(1→4)-ManNp-(1→3)-Glu, Glcp-(1→4)-GalN-(1→2)-Man, Manp-(1→3)-Glcp-(1→4)-GlcN, ManNp-(1→4)-Galp-(1→3)-Glc, GalNp-(1→3)-ManNp-(1→6)-GlcN. Rhamnp-(1→6)-Glcp-(1→4)-GlcN, Galp-(1→6)-Glcp-(1↔1)-Glcp, Talp-(1→4)-Glup-(1→2)-Man, Glup (1→3)-Idop-(1→6)-Glu, GlcNp-(1→6)-GlcNp (1→4)-GlcN.

Suitable tetrasaccharides include but are not limited to the following structures in which α,β anomeric mixtures at any ratio may exist, and where the individual sugars can be linked by either α or β glycosidic bonds and the individual sugars can be D or L: Galp-(1→4)-Glcp-(1→6)-glcp-(1→4)-Glc, Galp-(1→4)-Glcp-(1→4)-Glcp-(1→4)-Glcp-(1→4)-Glc, Galp-(1→4)-Glcp-(1→4)-Galp-(1→4)-Glc, Glcp-(1→4)-Glcp-(1→4)-Glcp-(1→4)-Glc, Galp-(1→6)-Glcp-(1→6)-Galp-(1→6)-Glc, Galp-(1→6)-Glcp-(1→6)-Galp-(1→4)-Glc, Galp-(1→6)-Glcp-(1→6)-Glcp-(1→4)-Glc, GlcNp-(1→4)-GlcNp-(1→6)-GlcNp-(1→4)-GlcN, GlcNp-(1→6)-Galp-(1→6)-Glcp-(1↔2)-Fruf, Galp-(1→4)-Glcp-(1→3)-Fruf-(2↔1)-Glcp, Talp-(1→4)-Glup-(1→2)-Man-(1-3)-Glu, Glup (1→3)-Idop-(1→6)-Glup-(1→2)-Gal.

Solvent

The composition of the solvent (dispersion medium) should not be particularly limited, and examples include biocompatible organic solvents such as ethanol, ethyl lactate, propylene carbonate, glycofurol, N-methylpyrrolidone, 2-pyrrolidone, propylene glycol, acetone, methyl acetate, ethyl acetate, methyl ethyl ketone, benzyl alcohol, triacetin, dimethylformamide, dimethylsulfoxide, tetrahydrofuran, caprolactam, decylmethylsulfoxide, such as but not limited to N-methyl-2-pyrrolidone, glycofurol, polyethylene glycol (PEG), benzyl benzoate, triglycerides, acetone, benzyl alcohol, N-(betahydromethyl) lactamide, butylene glycol, caprolactam, caprolactone, corn oil, decylmethylsulfoxide, dimethyl ether, dimethyl sulfoxide, 1-dodecylazacycloheptan-2-one, ethanol, ethyl acetate, ethyl lactate, ethyl oleate, glycerol, glycofurol (tetraglycol), isopropyl myristate, methyl acetate, methyl ethyl ketone, esters of caprylic and/or capric acids with glycerol or alkylene glycols, oleic acid, peanut oil, polyethylene glycol, propylene carbonate, 2-pyrrolidone, sesame oil, [±]-2,2-dimethyl-1,3-dioxolane-4-methanol, tetrahydrofuran, diethylene glycol monoethyl ether, carbitol, triacetin, triethyl citrate, and combinations thereof; or desirably from trichlorofluoromethane, dichlorofluoromethane, tetrafluoroethane (R-134a), dimethyl ether, propane, butane, and combinations thereof; or specifically from caprylic/capric triglyceride, oleic acid, 1-dodecylazacycloheptan-2-one and the like. Although the formulation can be stably dispersed in these solvents (dispersion media), the solvents may be further added with a saccharide derivatives of for example, triglycerides such as tri-pentanoyl glycerol, tri-octanoyl glycerol, tri-dodecanoyl glycerol, a monosaccharide such as glucose, galactose, mannose, fructose, inositol, ribose and xylose, disaccharide such as lactose, sucrose, cellobiose, trehalose and maltose, trisaccharide such as raffinose and melezitose, and polysaccharide such as α-, β-, or γ-cyclodextrin, sugar alcohol such as erythritol, xylitol, sorbitol, mannitol, and maltitol, or a polyhydric alcohol such as glycerin, diglycerin, polyglycerin, propylene glycol, polypropylene glycol, ethylene glycol, diethylene glycol, triethylene glycol, polyethylene glycol, ethylene glycol mono-alkyl ether, diethylene glycol mono-alkyl ether and 1,3-butylene glycol. Additives may furthermore be selected from the group consisting of bioavailable materials such as amiloride, procainamide, acetyl-beta-methylcholine, spermine, spermidine, lysozyme, fibroin, albumin, collagen, transforming growth factor-beta (TGF-beta), bone morphogenetic proteins (BMPs), fibroblast growth factor (bFGF), dexamethason, vascular endothelial growth factor (VEGF), fibronectin, fibrinogen, thrombin, proteins, dexrazoxane, leucovorin, ricinoleic acid, phospholipid, small intestinal submucosa, vitamin E, polyglycerol ester of fatty acid, Labrafil, Labrafil M1944CS, citric acid, glutamic acid, hydroxypropyl, isopropyl myristate, Eudragit, tego betain, dimyristoylphosphatidylcholine, scleroglucan, and the like; organic solvents such as cremophor EL, ethanol, dimethyl sulfoxide, and the like; preservatives such as methylparaben and the like; sugars such as starch and derivatives thereof, sugar-containing polyols such as sucrose-mannitol, glucose-mannitol, and the like; amino acids such as alanine, arginine, glycine, and the like; polymer-containing polyols such as trehalose-PEG; sucrose-PEG, sucrose-dextran, and the like; sugar-containing amino acid such as sorbitol-glycine, sucrose-glycine, and the like; surfactants such as poloxamer of various molecular weights, Tween 20 Tween 80, Triton X-100, sodium dodecyl sulfate(SDS), Brij, and the like; sugar-containing ions such as trehalose-$ZnSO_4$, maltose-$ZnSO_4$, and the like; and bio-acceptable salts such as silicate, NaCl, KCl, NaBr, NaI, LiCl, n-Bu$_4$NBr, n-Pr$_4$NBr, Et$_4$NBr, Mg(OH)$_2$, Ca(OH)$_2$, ZnCO$_3$, Ca$_3$(PO$_4$)$_2$, ZnCl$_2$, (C$_2$H$_3$O$_2$)$_2$Zn, ZnCO$_3$, CdCl$_2$, HgCl$_2$, CaCl$_2$, (CaNO$_3$)$_2$, BaCl$_2$, MgCl$_2$, PbCl$_2$, AlCl$_2$, FeCl$_2$, FeCl$_3$, NiCl$_2$, AgCl, AuCl, CuCl$_2$, sodium tetradecyl sulfate, dodecyltrimethyl-ammonium bromide, dodecyltrimethylammonium chloride, tetradecyltrimethyl-ammonium bromide, and the like, but not limited to those.

In one embodiment of the present invention, the content of the additive is from $1\times10^{-6}$-50 wt %, preferably $1\times10^{-3}$ to 30 wt %, based on the total weight of the gel forming component(s).

Contrast Agents

Contrast may be achieved using organic x-ray contrast agents, such as radiopaque agents such as iodinated compounds, which may be combined with chelators of MRI agents such as gadolinium, and/or combined with chelators of PET imaging agents such as copper-64, which may further be combined with solid inorganic particles. Chelators may be DOTA, EDTA, or DTPA and chelators will be non-covalently embedded or covalently conjugated to the gel-forming components. The combined contrast agents should preferably be visible by at least CT imaging. Preferred contrast agents are iodinated compounds such as polymers or sugar molecules such as derivatives of glucose or sucrose or other oligosaccharides. Solid particles may comprise, or consist of, one or more X-ray contrast agents, i.e., compounds that are able to block or attenuate X-ray radiation. Such compounds include transition metals, rare earth metals, alkali metals, alkali earth metals, other metals, as defined by the periodic table. A metal or alkali metal may appear in non-oxidized or any of the existing oxidation states for the metal. These oxidation states include monovalent cations, divalent cations, trivalent cations, tetravalent cations, pentavalent cations, hexavalent cations and heptavalent cations.

In one embodiment, the one or more X-ray contrast agents are selected from Iodine (I), gold (Au), bismuth (Bi), gadolinium (Gd), iron (Fe), barium (Ba), calcium (Ca) and magnesium (Mg). In a particular embodiment, the detectable compound comprises one or more compounds selected from the group of gold (Au) and bismuth (Bi). The one or more X-ray contrast agents are typically present in metal form, in alloy form, in oxide form or in salt form.

It should be understood that besides iodinated compounds which provides a useful contrast for X-ray imaging, the formulation may also include solid particles that are visible by X-ray imaging or other imaging modalities than X-ray imaging. In one embodiment, the solid-particles are furthermore visible by MR and/or PET imaging, or by other imaging modalities.

In a particular embodiment, the gel-forming composition may further comprise a radioactive or paramagnetic compound for one or more imaging modalities such as MRI, PET imaging, SPECT imaging, nuclear scintigraphy imaging, ultrasonography imaging, ultrasonic imaging, near-infrared imaging and/or fluorescence imaging.

In some interesting embodiments, the formulation according to any one of the preceding claims, contain solid particles that comprise one or more radioactive, paramagnetic or ferromagnetic particles.

Moreover, individual particles may comprise two or more types of compounds which are visible in different imaging modalities.

Said radioactive compounds may comprise isotopes of Copper ($^{61}$Cu, $^{64}$Cu, and $^{67}$Cu), Iodide ($^{123}$I, $^{124}$I, $^{125}$I, $^{131}$I), Indium ($^{111}$In), Technetium ($^{99m}$Tc), Rhenium ($^{186}$Re, $^{188}$Re), Gallium ($^{67}$Ga, $^{68}$Ga), Strontium ($^{89}$Sr), Samarium ($^{153}$Sm), Ytterbium ($^{169}$Yb), Thallium ($^{201}$Tl), Astatine ($^{211}$At), Lutetium ($^{177}$Lu), Actinium ($^{225}$Ac), Yttrium ($^{90}$Y), Antimony ($^{119}$Sb), Tin ($^{117}$Sn, $^{113}$Sn), Dysprosium ($^{159}$Dy), Cobalt ($^{56}$Co), Iron ($^{59}$Fe), Ruthenium ($^{97}$Ru, $^{103}$Ru), Palladium ($^{103}$Pd), Cadmium ($^{115}$Cd), Tellurium ($^{118}$Te, $^{123}$Te), Barium ($^{131}$Ba, $^{140}$Ba), Gadolinium ($^{149}$Gd, $^{151}$Gd), Terbium ($^{169}$Tb), Gold ($^{198}$Au, $^{199}$Au), Lanthanum ($^{140}$La), Zirconium ($^{89}$Zr), Titanium ($^{45}$Ti) and Radium ($^{223}$Ra, $^{224}$Ra), wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations.

Said paramagnetic or ferromagnetic compounds may also be selected from the group of Scandium (Sc), Yttrium (Y), Lanthanum (La), Titanium (Ti), Zirconium (Zr), Hafnium (Hf), Vandium (V), Niobium (Nb), Tantalum (Ta); Chromium (Cr), Molybdenium (Mo), Tungsten (W), Manganese (Mn), Technetium (Tc), Rhenium (Re), Iron (Fe), Ruthenium (Ru), Osmium (Os), Cobalt (Co), Rhodium (Rh), Iridium (Ir), Nickel (Ni), Palladium (Pd), Platinum (Pt), Copper (Cu), Silver (Ag), Gold (Au), Zinc (Zn), Cadmium (Cd), Mercury (Hg), the lanthanides such as Lanthanum (La), Cerium (Ce), Praseodymium (Pr), Neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), Lutetium (Lu)) and the actinides such as Actinium (Ac), Thorium (Th), Protactinium (Pa), Uranium (U), Neptunium (Np), Plutonium (Pu), Americium (Am), Curium (Cm), Berkelium (Bk), Californium (Cf), Einsteinium (Es), Fermium (Fm), Mendelevium (Md), Nobelium (No) and Lawrencium (Lr), wherein said paramagnetic or ferromagnetic compounds may appear in any of the existing oxidation states for the metal. These oxidation states include monovalent cations, divalent cations, trivalent cations, tetravalent cations, pentavalent cations, hexavalent cations and heptavalent cations.

Said one or more radioactive, paramagnetic or ferromagnetic compounds may be covalently linked to gel-forming components or the nano-sized particles or non-covalently associated with the gel-forming components or nano-sized particles.

In one embodiment, the gel-forming components or nano-sized particles further comprise one or more fluorophore compounds for near infrared fluorescence imaging. Said compounds may comprise a fluorescent proteins, peptides, or fluorescent dye molecules. Common classes of fluorescent dyes include xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes, polymethine, oxabenzanthrane, xanthene, pyrylium, carbostyl, perylene, acridone, quinacridone, rubrene, anthracene, coronene, phenanthrecene, pyrene, butadiene, stilbene, lanthanide metal chelate complexes, rare-earth metal chelate complexes, and derivatives of such dyes. Typical fluorescein dyes include 5-carboxyfluorescein, fluorescein-5-isothiocyanate and 6-carboxyfluorescein; examples of other fluorescein dyes can be found, for example, in U.S. Pat. Nos. 6,008,379, 5,750,409, 5,066,580, and 4,439,356. The species may also include a rhodamine dye, such as, for example, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED), and other rhodamine dyes. The species may alternatively include a cyanine dye, such as, for example, Cy3, Cy3B, Cy3.5, Cy5, Cy5.5, Cy. Or IRDye 800CW, IRDye 680LT, Qdot 800 nanocrystal, Qdot 705 nanocrystal or porphyrazine compounds In another embodiment, the nano-sized particles further comprise or consist of one or more gasses encapsulated in lipid, polymer or inorganic based particles for ultrasonography imaging. Said gasses may comprise air, sulphur halides such as sulphur hexafluoride or disulphur decafluoride; fluorocarbons such as perfluorocarbons; fluorinated (e.g. perfluorinated) ketones such as perfluoroacetone; and fluorinated (e.g. perfluorinated) ethers such as perfluorodiethyl ether. Representative perfluorocarbons, which may for example contain up to 7 carbon atoms, include perfluoroalkanes such as perfluoromethane, perfluoroethane, perfluoropropanes, perfluorobutanes (e.g. perfluoro-n-butane, optionally in a mixture with other isomers such as perfluoro-iso-butane), perfluoropentanes, perfluorohexanes and perfluoroheptanes; perfluoroalkenes such as perfluoropropene, perfluorobutenes (e.g. perfluorobut-2-ene) and perfluorobutadiene; perfluoroalkynes such as perfluorobut-2-yne; perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane; and mixtures of any of the foregoing, including mixtures with gases such as nitrogen, carbon dioxide, oxygen etc, but not limited to those.

In another embodiment, contrast in achieved using small organic iodine containing compounds. Said small organic iodine containing compounds includes commercial available iodinated contrast agents such as diatrizoate (marketed e.g. under the trade name Gastrografen™), ionic dimers such as ioxaglate (marketed e.g. under the trade name Hexabrix™), nonionic monomers such as iohexol (marketed e.g. under the trade name Omnipaque™), iopamidol (marketed e.g. under the trade name Isovue™) iomeprol (marketed e.g. under the trade name Iomeron™) and the non-ionic dimer iodixanol (marketed under the trade name and Visipaque™). Additional examples of small organic iodine containing compounds includes the ones disclosed in WO 2009/071605, EP1186305, EP686046, EP108638, EP0049745, EP0023992, WO 2003080554, WO 2000026179, WO 1997000240, WO 9208691, U.S. Pat. Nos. 3,804,892, 4,239, 747, 3,763,226, 3,763,227 and U.S. Pat. No. 3,678,152, but not limited to those. In another interesting embodiment, the said small organic iodine containing compounds includes iodinated derivates of sucrose acetate isobutyrate (SAIB). In contrast to what is disclosed in for example EP1006935, where a composition for controlled release of a substance is disclosed which composition comprises SAIB, this specific embodiment according to the present invention aims at providing a stable contrast agent embedded in SAIB-gel. Such compounds may be used alone or in combination with solid particles to achieve an injectable gel visible by at least CT imaging. In one specific embodiment of the invention the hydration sensitive gel forming component is sucrose acetate isobutyrate (SAIB) a hydrophobic component composed of sucrose (the scaffold), which has been acylated with isobutyrate and acetate. Preferred scaffolds of this invention are monosaccharides, disaccharides or trisaccharides. A particularly preferred dissaccharide scaffold are sucrose and lactose, however, the alcohol containing scaffold may be derived from a polyhydroxy alcohol having from about 2 to about 20 hydroxy groups and may be formed by esterifying 1 to 20 polyol molecules. Suitable alcohol moieties include those derived by removing one or more hydrogen atoms from: monofunctional C1-C20 alcohols, difunctional C1-C20 alcohols, trifunctional alcohols, hydroxy-containing carboxylic acids, hydroxy-containing amino acids, phosphate-containing alcohols, tetrafunctional alcohols, sugar alcohols, monosaccharides, and disaccharides, sugar acids, and polyether polyols. More specifically, alcohol moieties may include one or more of: dodecanol, hexanediol, more particularly, 1,6-hexanediol, glycerol, glycolic acid, lactic acid, hydroxybutyric acid, hydroxyvaleric acid, hydroxycaproic acid, serine, ATP, pentaerythritol, mannitol, sorbitol, glucose, galactose, fructose, maltose, lactose, glucuronic acid, polyglycerol ethers containing from 1 to about 10 glycerol units, polyethylene glycols containing 1 to about 20 ethylene glycol units. Additionally, any oligosaccharide containing from 3 to about 6 monosaccharides may be used as the scaffold in the present invention. In general, the scaffold esters of the invention can be made by reacting one or more alcohols, in particular one or more polyols, which will form the alcohol moiety of the resulting esters with one or more carboxylic acids, lactones, lactams, carbonates, or anhydrides of the carboxylic acids which will form the acid moieties of the resulting esters. The esterification reaction can be conducted simply by heating, although in some instances addition of a strong acid or strong base esterification catalyst may be used. Alternatively, an esterification catalyst such as stannous 2-ethylhexanoate or activation reagents such as N-(3-Dimethylaminopropyl)-N'-ethylcarbodiimide (EDC), N,N'-Dicyclohexylcarbodiimide (DCC), O-(7-azabenzotriazol-1-yl)-N,N,N',N'-tetramethyluronium hexafluorophosphate (HATU) and the like can be used.

The acyl groups forming the acyloxy substituents of the invention may be any moiety derived from a carboxylic acid. More particularly, the acyl groups of the compositions of the invention may be of the RCO—, where R is optionally oxy-substituted alkyl of 2-10 carbon atoms which may be linear or branched hydrocarbons with one or more functional groups present in the chain. Using carboxylic acids and/or polyols of different chain length and using carboxylic acids having oxy-substitution allows control of the degree of hydrophilicity and of the solubility of the resulting ester. Such materials are sufficiently resistant to dissolution in vivo that they are able to form stabile hydrophobic gels which may encapsulate the said contrast agents of the present invention.

In one embodiment the composition for use is an X-ray contrast agent comprises one or more iodinated polymers, iodinated oligomers, iodinated lipids, iodinated saccharides, iodinated disaccharides, iodinated polysaccharides, iodinated peptides, or a derivative or a combination thereof. The composition for use according to any of the preceding claims, wherein the composition comprises iodinated derivates of carbohydrate or iodinated derivative of poly-alcohols, such as iodinated derivatives of sucrose acetate isobutyrate (SAIB), such as iodinated derivatives of lactose, such as iodinated derivatives of trehalose, such as iodinated derivatives of arabinose, such as iodinated derivatives of maltose, such as iodinated derivatives of glucose, such as iodinated derivatives of galactose, iodinated derivatives of glucosamine, such as iodinated glucosamine, and the like. In yet another embodiment the composition comprises an iodinated derivate of a carbohydrate doped into a composition of the same class of non-idoninated carbohydrate derivatives.

Further, in one embodiment, the X-ray contrast composition comprises sucrose acetate isobutyrate (SAIB) or a derivative thereof and in one specific embodiment of the present invention, the X-ray contrast composition comprises an iodinated derivate of sucrose acetate isobutyrate (SAIB). Furthermore in another specific embodiment of the present invention the X-ray contrast composition comprises an iodinated derivate of sucrose acetate isobutyrate (SAIB) doped into sucrose acetate isobutyrate (SAIB). This has been evaluated for stability and the amount of this iodo-SAIB/SAIB that can be doped into SAIB, is at least 50 mol %.

The iodo-SAIB provides high X-ray contrast. The iodo-SAIB compound is poorly soluble in ethanol and is a white solid whereas SAIB is highly soluble in ethanol and is a thick oil. However, a mixture of ethanol and SAIB can solubilize the iodo-SAIB very nicely. This means that the SAIB helps solubility of iodo-SAIB, which is an interesting feature and which provides an injectable solution which gelates after administration (through a thin needle, thinner than 20 gauge) that can function as a high contrast X-ray marker. When injected into mice, the iodo-SAIB/SAIB provides high contrast and has the desirable stability properties. Furthermore, the gel seems homogeneous. In one embodiment of the present invention the X-ray contrast composition comprises an iodinated derivate of sucrose acetate isobutyrate (SAIB) solubilised in a mixture of ethanol and sucrose acetate isobutyrate (SAIB).

Features of Injectable Medical Gel-Forming System (1) In order to be injectable, the system should be in a sol state such as a liquid like state before administration. The sol state should be of sufficiently low viscosity—typically lower than 10,000 cP, preferably lower than 2,000 cP, at 20° C. (or alternatively lower than lower than 10,000 cP, preferably 2,000 cP, at 5° C.)—to allow for small needle head to alleviate the patient discomfort and simplify insertion procedure.

(2) Gelation via physical association or hydration starts to happen or is complete after injection.

(3) The gels should be biodegradable or gradually dissolvable within a controlled time period, and the products should be cleared/secreted through normal pathways.

(4) The polymer itself and the degradable products should be biocompatible. Likewise, if additives are added, such as cross-linking agents, initiators etc. these should also be biocompatible.

(5) The gel could potentially have cell/tissue-adhesive properties.

It should be understood, that the gel-forming system should preferably be biocompatible, i.e. does not stimulate a severe, long-lived or escalating biological response to the formulation when injected into a mammal, in particular a human. To facilitate metabolism of the gel scaffold, degradable linkages can be included through the use of polylactide, polyglycolide, poly(lactide-co-glycolide), polyphosphazine, polyphosphate, polycarbonate, polyamino acid, polyanhydride, and polyorthoester-based building blocks, among others. Additionally, small molecule crosslinking agents containing similar hydrolyzable moieties as the polymers such as carbonates, esters, urethanes, orthoesters, amides, imides, imidoxy, hydrazides, thiocarbazides, and phosphates may be used as building blocks. Additionally, polyglycolide diacrylate, polyorthoester diacrylate and acrylate-substituted polyphosphazine, acrylate-substituted polyamino acid, or acrylate-substituted polyphosphate polymers can be used as degradable building blocks. Methacrylate or acrylamide moieties can be employed instead of acrylate moieties in the above examples. Similarly, small molecules containing a hydrolyzable segment and two or more acrylates, methacrylates, or acrylamides may be used. Such degradable polymers and small molecule building blocks may be functionalized with acrylate, methacrylate, acrylamide or similar moieties by methods known in the art.

In order to be injectability, the system should be in a sol state before administration. The sol state should be of sufficiently low viscosity to allow for small needle head to alleviate the patient discomfort and simplify insertion procedure. Gelation via physical association starts to happen or is complete after injection.

In one embodiment, the composition according to the present invention is administered using topical route.

In one embodiment, the composition according to the present invention is intra-cavitary administration into existing or established body cavities. The existing cavities include, but are not limited to; urinary bladder, uterus, gall bladder, sinuses, middle ear. The established or formed cavities include, but are not limited to cavities formed in relation to surgery and infections.

Viscosity of the Formulation

The viscosity of the formulation is before the injection preferably lower than 10,000 cP, in particular lower than 2,000 cP, at 20° C. Alternatively, the viscosity of the formulation is before the injection typically lower than 2,000 cP at 5° C.

In one embodiment, the gel-forming system of the formulation is preferably one which, after injection or under conditions mimicking those in a human body, forms a gel having a viscosity at 37° C. in the range of 2,000 to 50,000,000 cP. More particularly, the viscosity of the hydrogel can be about 2,000 cP, about 5,000 cP, about 10,000 cP, about 20,000 cP, about 30,000 cP, about 50,000 cP, about 75,000 cP, about 100,000 cP, about 125,000 cP, about 150,000 cP, about 200,000 cP, about 30,000 cP, about 800,000 cP, about 1,000,000 cP, about 2,000,000 cP, about 5,000,000 cP, about 10,000,000 cP, about 20,000,000 cP, about 30,000,000 cP, about 40,000,000 cP, about 50,000,000 cP, or ranges thereof. Preferably, the viscosity of the hydrogel after injection (i.e. when present in the desired location) is above 20,000 cP, e.g. in the range of 20,000 cP to 1,000,000 cP. In particular, the formulation after injection is preferably essentially solid.

Preferred Properties of the Gel-Forming System

In one embodiment, the preferred systems include non-water soluble high-viscosity liquid carrier materials such as non-water soluble carbohydrates and in particular carbohydrates selected from derivatives of disaccharides with at least two pyranose saccharide units, trisaccharides, tetrasaccharides or mixtures thereof, or derivatives of lactose, maltose, trehalose, raffinose, glucosamine, galactosamine, lactosamine, or mixtures thereof. Such systems may be mixed with solid particles that carry drug or contrast agent followed by parental injection, thus functioning as a injectable composition, which that can be visualized by one or multiple imaging modalities, including X-ray imaging.

In one embodiment of the invention the composition comprising a non-water soluble carbohydrate, wherein the composition is a liquid before administration into the human or animal body and increases in viscosity by more than 1,000 centipoise (cP) after administration. In one embodiment of the invention the composition comprising a non-water soluble carbohydrate, wherein the composition is a liquid before administration into the human or animal body and increases in viscosity by more than 10,000 centipoise (cP) after administration.

In one embodiment, at least 60% of an administered amount of the non-water soluble carbohydrate remains more than 24 hours within 10 cm from an injection point when administrated to a human or animal body.

In one preferred embodiment, the mixing of different acylated carbohydrates, results in controlled drug release providing tuning of release kinetics for the individual drug. The composition according to the present invention also relates to the release of one or more active pharmaceutical ingredients being controlled by mixing carbohydrates with different hydrophobicity by alteration of the substitutions on the carbohydrate hydroxyl groups. With the aid of tuning the hydrophobicity, the release rate of the present invention may be changed, this implies therefore increased control of the process. Rendering it suitable for controlled release of for example pharmaceutuicals and other substances. Active pharmaceuticals may be formulated in various forms and the present invention is to be seen as incorporating various forms of formulations of the active ingredient.

Other Constituents of the Formulation

In one embodiment a polymer may be used to work as a stabilizer between gel and biological surrounding and therefore, the composition may also comprises a molecule that increase gel stability in the human or animal body, such as an amphiphilic molecule, such as an emulsifier. Therefore in one embodiment the composition comprises poly(ethylene glycol-b-caprolactone) (PEG-PCL), sucrose acetate isobutyrate (SAIB), poly(D,L-lactic acid) (PLA), or poly(lactic-co-glycolic acid) (PGLA), or a combination thereof. In one embodiment of the present invention poly(D,L-lactic acid) (PLA) is added to the non-water soluble carbohydrate causing a reduction of burst release of said encapsulated contents e.g. drugs, particles, contrast agents, etc. The formulation may further include other constituents, such as α-, β-, and/or γ-cyclodextrins and any derivate hereof. Such constituents may form guest/host complexes with the gel forming system and the nano-sized particles, thus, both aiding in the gel formation and possible alter the particle leakage profile [Adv. Drug Delivery Rev., 2008, 60, 1000-1017]. In one very interesting embodiment the gel forming system is based on PEG-PHB-PEG triblock copolymers, α-cyclodextrin and PEG coated solid nano sized particles. In such a formulation, α-cyclodextrin may form inclusion complexes with both the PEG blocks of the PEG-PHB-PEG triblock copolymers and the PEG coated solid nano sized particles which, combined with hydrophobic interactions between the PHB middle block, forms a strong hydrogel with enhanced retention of solid nano sized particles due α-cyclodextrin interactions which thus altering the particle leakage profile.

The formulation may further comprise compounds or polymers, which are visible in imaging modalities other than X-ray imaging.

In one embodiment, the formulation further comprises an iodine-containing polymer, e.g. polyvinylpyrrolidone-iodine (PVP-I), or one selected from i) Polym. Chem., 2010, 1, 1467-1474, ii) U.S. Pat. No. 3,852,341, iii) U.S. Pat. No. 4,406,878, iv) U.S. Pat. No. 5,198,136, v) Biomedical polymers and polymers therapeutics, Ed. Chiellini E., Sunamoto J., Migliaresi C., Ottenbrite R. M., Cohn D., New York, Kluwer Academic Publishers, 2002, ISBN 0-30646472-1, Print, and references cited therein. Such polymers can be added to the gel forming components prior to gelation and function as contrast agent in vivo. Such polymers may additionally or alternatively be covalently bound to the one or more of the gel forming components or adhered to the particles of the present invention.

In one specific embodiment, the formulation consist of iodinated SAIB as contrast agent with high HU-contrast or a iodinated carbohydrate.

Pharmaceutical Agent

The gel-forming formulation may further comprise pharmaceutical agents including prodrugs (in short "drugs"; broadly interpreted as agents which are able to modulate the biological processes of a mammal). These drugs can be formulated as a single drug or as a combination of two or more of the below mentioned drugs in its active form or as a prodrug.

In one embodiment, the active pharmaceutical ingredient is an immunomodulating compound which is a ligand for intracellular proteins and/or receptors; or a ligand for cell surface proteins and/or receptors. In yet another embodiment, the intracellular proteins and/or receptors are selected from the group consisting of NOD-like receptor (NLR) family and the subfamilies NLRA, NLRB, NLRC, NLRP, NODs, NALP, IPAF, HLA complexes, Receptor tyrosine kinases (RTK), Integrins, tumor necrosis factor receptor superfamily (TNFRSF; TNFR1, TNFR2, OX40, 4-1BB, CD40), ATP and ADP receptors; P2x1-7 and G-protein coupled $P2Y_{1-8}$, cyclo-oxygenase (COX) receptors, prostaglandin receptors, chemokine receptors; CXCR and CCR, EIF2AK4, RIG-I-like receptors, cytokine receptors, interleukin receptors, CD proteins, CTLA proteins, PD1, T Cell receptor, B cell receptor, and the Toll-like-receptor (TLR) family; TLR1, TLR2 TLR3, TLR4, TLR5, TLR6, TLR7, TLR8, TLR9, TLR10, TLR11, TLR12, TLR13.

Examples of pharmaceutical active agents include small drugs, plasmid DNA (e.g. for gene therapy), dsRNA, ssRNA, mRNA, siRNA, carbohydrates, peptides and proteins. Specific examples of pharmaceutical agents include; a) chemotherapeutic agents such as alkylating agents, antimetabolites, enzymes (e.g. L-asparginase), natural product chemotherapeutics including tubulin stabilizing and destabilizing agents, hormones and antagonists, etc.; b) radiation sensitizing agents such as gemcitabine and doranidazole, porphyrins for photodynamic therapy (e.g. visudyne) or $^{10}$B clusters or $^{157}$Gd for neutron capture therapy; c) peptides or proteins that modulate apoptosis, the cell cycle, or other crucial signaling cascades; d) anti inflammatory drugs, such as methylprednisolone hemisuccinate, β-methasone; e) anti anxiety muscle relaxants such as diclofenac, pridinol; f) local anesthetics such as lidocaine, bupivacaine, dibucaine, tetracaine, procaine; g) analgesics such as opiods, non-steroidal anti-inflammatory drugs (NSAIDs); h) antimicrobial medications such as pentamidine, azalides; i) antipsychotics such as chlorpromazine, perphenazine; j) the antiparkinson agents such as budipine, prodipine, benztropine mesylate, trihexyphenidyl, L-DOPA, dopamine; k) Antiprotozoals such as quinacrine, chloroquine, amodiaquine, chloroguanide, primaquine, mefloquine, quinine; l) antihistamines such as diphenhydramine, promethazine; m) antidepressants such as serotonin, imipramine, amitriptyline, doxepin, desipramine; n) anti anaphylaxis agents such as epinephrine; o) anticholinergic drugs such as atropine, decyclomine, methixene, propantheline, physostigmine; p) antiarrhythmic agents such as quinidine, propranolol, timolol, pindolol; q) prostanoids such as prostaglandins, thromboxane, prostacyclin, but not limited to those; r) immunotherapeutic agents such as imidazoquinoline amine, immunomodulators, guanosine derivatives, pyrimidone derivatives, immunosuppressants, pro- or anti-inflammatory cytokines, antibodies, but not limited to those.

Additional examples of antitumor agents and/or radiation sensitizing agents include camptothecin derivatives such as irinotecan hydrochloride, nogitecan hydrochloride, exatecan, RFS-2000, lurtotecan, BNP-1350, Bay-383441, PNU-166148, IDEC-132, BN-80915, DB-38, DB-81, DB-90, DB-91, CKD-620, T-0128, ST-1480, ST-1481, DRF-1042 and DE-310, taxane derivatives such as docetaxel hydrate, IND-5109, BMS-184476, BMS-188797, T-3782, TAX-1011, SB-RA-31012, SBT-1514 and DJ-927, ifosfamide, nimustine hydrochloride, carboquone, cyclophosphamide, dacarbazine, thiotepa, busulfan, melphalan, ranimustine, estramustine phosphate sodium, 6-mercaptopurine riboside, enocitabine, gemcitabine hydrochloride, carmofur, cytarabine, cytarabine ocphosphate, tegafur, doxifluridine, hydroxycarbamide, fluorouracil, methotrexate, mercaptopurine, fludarabine phosphate, actinomycin D, aclarubicin hydrochloride, idarubicin hydrochloride, epirubicin hydrochloride, daunorubicin hydrochloride, pirarubicin hydrochloride, bleomycin hydrochloride, zinostatin stimalamer, neocarzinostatin, mytomycin C, bleomycin sulfate, peplomycin sulfate, vinorelbine tartrate, vincristine sulfate, vindesine sulfate, vinblastine sulfate, amrubicin hydrochloride, gefitinib, exemestan, capecitabine, TNP-470, TAK-165, KW-2401, KW-2170, KW-2871, KT-5555, KT-8391, TZT-1027, S-3304, CS-682, YM-511, YM-598, TAT-59, TAS-101, TAS-102, TA-106, FK-228, FK-317, E7070, E7389, KRN-700, KRN-5500, J-107088, HMN-214, SM-11355, ZD-0473, magnesium 5,10,15,20-tetrakis(4-sulphophenyl)-porphine dodecahydrate, PYROA protein (Emericella nidulans), photosan III, lomefloxacin, cyamemazine, tiaprofenic acid, doxorubicin, mitomycin, paclitaxel, nitrogen mustards, etoposide, camptothecin, 5-fluorouracil, nicotinamide, metronidazole, doxorubicine, Lomeguatrib, Temozolomide, tamoxifen, bleomycin, 5-fluorouracil, cyclophosphamide, methotrexate, gemcitabine, oxaliplatin, cisplatin, carboplatin, camptothecin, CPT-11 (SN-38), Etanidazole, Nimorazole, Mitomycin C, Tirapazamine, procaine, lidocaine, chlorpromazine, Fluordeoxyuridine, bromodeoxyuridine, iododeoxyuridine, hydroxyurea, fludarabine, Texaphyrins (motexafin gadolinium), N-ethylmalemide, paclitaxel, docetaxel, irinotecan, Mechrorethamine, Cyclophosphamide, Ifosfamide, Melphalan, Chlorambucil, Procarbazine (N-methylhydrazine, MIH), Busulfan, Camustine (BCNU), Streptozocin (streptozotocin), Bendamustine, Dacarbazine (DTIC; dimethyttriazenol midazole carboxamide), Temozolomide, Cisplatin, carboplatin, oxaliplatin, Methotrexate (Amethopterin), Pemetrexed, Fluorouracil (5-fluorouracil; 5-FU), capecitabine, Cytarabine (cytosine arabinoside), Gemcitabine, 5-aza-cytidine, Deoxy-5-aza-cytidine, Mercaptotirine (6-mercaptopurine; 6-MP), Pentostatin (2'-deoxycoformycin), camptothecin, SN-38 (CPT-11), Rudarabine, Clofarabine, Nelarabine, Tirapazamine, Vinblastine, Vinorelbine, Vincristine, Paclitaxel, docetaxel, Etoposide, Teniposide, Topotecan, Irinotecan, Dactinomycin, (actinomycin D). Daunorubicin (daunomycin, rubidomycin), Doxorubicin, Yondelis, Mitoxantrone, Bleomycin, Mitomycin C, L-Asparaginase, Mitotane (o.pDDD) Prednisone, Hydroxyprogesterone caproate, medroxyprogesterone acetate, megestrol acetate, Dietyhlstilbestrol, ethinyl estradiol, Tamoxifen, toremifene, Anastrozole, letrozole, exemestane, Testosterone propionate, fluoxymesterone, Flutamide, casodex, Leuprolide. Hydroxyurea, Tretinoin, arsenic trioxide, Histone deacetylase inhibitor (vorinostat), Imatinib, Dasatinib, nilotinib, Gefrtinib, ertoinib, Sorafenib, Sunitinib, Lapatinib, Bortezomib, interferon-alfa, Interleukin-2, interleukin-15, Thalidomide, Lenaiidomide, Temsiroiimus, Everolimus, and the like, but not limited to those.

Examples of immunotherapeutic agents include resiquimod, imiquimod, thalidomide, lenalidomide and pomalidomide, sargramostim, IL-2, IL-15, IFN-a, IFN-b, IFN-g, interferon-alfa, alemtuzumab, bevacizumab, brentuximab vedotin, cetuximab, gemtuzumab, ozogamicin, ibritumomab, tiuxetan, ipilimumab, ofatumumab, panitumumab, rituximab, tositumomab, trastuzumab, loxoribine, bropirimine, pomalidomide, sargramostim and the like, but not limited to those. In one embodiment, the active pharmaceutical ingredient is an immuno stimulating compound selected from the group consisting of polyinosinic:polycytidylic acid (poly I:C), Polyadenylic-polyuridylic acid (poly A:U), poly I:C-poly-L-lysine (poly-ICLC), poly-ICR, 3p'dsRNA, 3p'dsDNA, 2p'dsRNA, 2p'dsDNA, p'dsRNA, p'dsDNA, dsRNA, dsDNA, ssDNA, ssRNA, methyl-tryptophan, D-1MT, L-1MT, tryptophan, INCB24360, NLG919, INCB24360 (Incyte), NLG919 (NewLink Genetics), LM10 (Ludwig Institute), Compound 9 (The Institutes for Pharamceutical Discovery), NCX-4016 (NicOx), AT38 (IRCCS), Tadalafil (Eli Lilly), arginine, N-hydroxy-nor-L-arginine, AZ10606120 (University of Ferrara), NF340 (Uni Dusseldorf), SCH58261 (Peter MacCallum Cancer Centre), SCH420814 (Merck), PSB1115 (Uni Salerno), ARL67176 (Orega Biotech), AMPCP (Uni Texas San Antonio), Celecoxib (Pfizer), PF04418948 (Pfizer), RQ-15986 (RaQualia Pharma), Plerixafor (Sanofi-Avantis), PF-4136309 (Pfizer), Maraviroc, OM-174, 852A (Pfizer), VTX-2337 (VentiRx), IM-2055 (Idera Pharmaceuticals), LY2157299 (Eli Lilly), EW-7197 (Ewha), BLZ945, BMS-777607, PI-3065, TG100-115, Babrafenib, Vemurafenib, ARL67176, VS4718, ASP3026, Crizotinib, GSK1838705, KRCA0008, PF064639229, CL264, N-palmitoyl-S-[2,3-bis(palmitoyloxy)-(2R,S)-propyl]-(R)-cysteine-(S)serine-(S)lysine 4 (Pam$_3$Cys), Monophosphoryl lipid A (MPLA) and other lipopolysaccharides, alpha-galactosylceramide, Propirimine, Imiquimod (R837), resiquimod (R848), TMX-101, TMX-201, TMX-202, Gardiquimod, R850 (3M Pharma), R851 (3M Pharma), 852A (3M Pharma), S-27610, 3M-002 (CL075), 3M-003, 3M-005, 3M-006, 3M-007, 3M-012, 3M-13, 3M-031, 3M-854 (3M Pharma), CL097, CL264, IC-31, Loxoribine and other imidazoquinolines, ssPolyU, sotirimod (3M Pharma), Isatoribine (Anadys), ANA975 (Anadys/Novartis), SM360320 (Sumitomo), R1354 (Coley Pharmaceuticals) single stranded or double stranded RNA, ORN 02 (5'-UUAUUAUUAUUAUUAUUAUU-3'), ORN 06 5'-UUGUGGUUGUUGUUGUUGUU-3', CpG-ODN DSLIM (Mologen), AVE 0675 (Coley Pharmaceuticals), CpG B oligodeoxynucleotide (ODN) 1018 (Dynavax Technologies), AZD 1419 (Dynavax), ODN 1982, CpG B ODN 2006 (Coley Pharmaceuticals), IMO 2125 (Idera Pharma), CpG A ODN 2216, CpG A ODN 2336, CpG 2395, CpG ODN 7909 (Coley Pharmaceuticals), CpG 10101 (Coley Pharmaceuticals), CpG ODN AVE0675 (Coley Pharmaceuticals), CpG ODN HYB2093 (Idera Pharmaceuticals/Novartis), CpG ODN HYB2055 (Idera Pharmaceuticals), CpG-ODN IMO-2125 (Idera Pharmaceuticals), CpG C ODN M362, Tolamba (Amb a1 ragweed allergen with covalently linked CpG B class ODN 1018)(Dynavax Technologies), Heplisav (Dynavax Technologies), 10181SS (Dynavax Technologies), IM02055 (Idera Pharmaceuticals), IRS954 (Dynavax Technologies), (flagellin, muramyl dipeptide, saponins such as QS21, Leishmania elongation factor, SB-AS4, threonyl-muramyl dipeptide, L18-MDP, mifamurtid, A83-01, A4476, GW788383, LY364947, R268712, RepSox, SB431542, SB505124, SB525334, SD208, FAK inhibitor 14, PF431396, PF573228, Yll and OM-174. In yet another embodiment, the active pharmaceutical ingredient is an immuno suppressive compound comprising a steroid selected from the group consisting of 21-Acetoxyprefnenolone, Aalclometasone, Algestone, Amicinonide, Beclomethasone, Betamethasone, Betamethasone dipropionate, Betamethasone hemisuccinate, Budesonide, Chloroprednisone, Clobetasol, Blovetasone, Clocortolone, Cloprednol, Corticosterone, Cortisone, Cortivazol, Deflazacort, Desonide, Desoximethasone, dexamethason, Dexamethasone palmitate, Dexamethasone phosphate, Diflorasone, Diflucortolone, Difluprednate, Enoxolone, Fluazacort, Flucloronide, Flumethasone, Flunisolide, Fluocinolone Acetonide, Fludrocortisone, Fluocinonide, Fluocortin Butyl, Fluocortolone, Fluorometholone, Fluperolone, Fluprednidine, Fluprednisolone, Flurandrenolide, Formocortal, Halcinonide, Glucocorticoids, Halomethasone, Halopredone, Hydrocortamate, Hydrocortisone, Limethasone, Mazipredone, Medrysone, Meprednisone, Methyolprednisolone, Methyolprednisolone hemisuccinate, Mometasone Furoate, Paramethasone, Prednicarbate, Prednisolone, Prednisolone palmitate, Prednisolone phosphate, Prednisone, Prednival, Prednylidene, Tixocortal, and Triamcinolone. In yet another embodiment, the active pharmaceutical ingredient is an immuno suppressive compound comprising a small molecule inhibitor acting on intracellular targets selected from the group consisting of c-Fms, PDGFR□, Abl, PDGFR□, NFkB, IkB, JAK1, JAK2, JAK3, GSK3, p38 MAPK, JNK, KIT, EGFR, ERBB2, ERBB4, VEGFR1, VEGFR2, VEGFR3, FLT3, PKC□, RAF1, CDK1, CDK2, CDK4, NLRP3, IRF3, STAT1, STAT2, STAT3, STAT4, STAT5, STAT6, Hsp90, Hsp70, PI3K, mTOR, AKT, DNA-PK, ATM, AMPK, PDK-1, S6 kinase, RIP2, TRIF, MYD88, TAK1. In yet another embodiment, the active pharmaceutical ingredient is an immuno suppressive compound comprising a small molecule inhibitor acting on intracellular targets selected from the group consisting of indomethacin, CLI-095 (C15H17CIFNO4S, CAS #243984-11-4), Bayl1-7082 (C10H9NO2S, CAS #19542-67-7), Triptolide (PG 490), CGP53716, SU9518, PD166326, Celastrol, Tripterin, BIRB-796 (Doramapimod), SB 203580, SB202190, VX-702, NVP-BEZ235, GDC-0980 (RG7422), Ridaforolimus (Deforolimus, AP23573), Nilotinib (Tasigna, AMN107), Sorafenib tosylate (Nexavar), Dasatinib (Sprycel, BMS-354825), MLN518 (CT53518), Vatalanib (PTK787/ZK222584), OSI-930, AZD2171, Pazopanib (Votrient), IPI-504 (retaspimycin), Deforolimus (Ridaforolimus), GDC-0980 (RG7422, $C_{23}H_{30}N_8O_3S$, CAS #1032754-93-0), Palomid 529 ($C_{24}H_{22}O_6$ CAS #914913-88-5), Imatinib mesylate (Gleevec/Glivec), Everolimus (Afinitor, RAD001), Sirolimus (Rapamune, rapamycin), Temsirolimus (Torisel, CCI-779), Bortezomib (Velcade), Gefitinib (Iressa), Canertinib (CI-1033, CAS #267243-28-7, $C_{24}H_{25}CIFN_5O_3$), Erlotinib hydrochloride (Tarceva), Pelitinib (EKB-569) ($C_{24}H_{23}CIFN_5O_2$, CAS #257933-82-7), Vandetanib (Zactima, ZD6474, $C_{22}H_{24}BrFN_4O_2$, CAS No.: 443913-73-3), Sunitinib (Sutent, SU-11248, $C_{22}H_{27}FN_4O_2 \cdot C_4H_6O_5$, CAS No.: 341031-54-7), Tandutinib (MLN518), $C_{31}H_{42}N_6O_4$, CAS No.: 387867-13-2, Roscovitine (Seliciclib), $C_{19}H_{26}N_6O$, CAS No.: 186692-46-6. In yet another embodiment, the active pharmaceutical ingredient is an anti-infectious compound selected from the group consisting of Rifampicin, dideoxycytidine-5'-triphosphate, Clarithromycin, acyclovir, ciprofloxacin, fusidin, gentamicin, chloramphenicol, levofloxacin, oxytetracyclin, tobramycin, natriumcromoglicat, Amoxicillin, Ampicillin, Pivampicillin, Ertapenem, Meropenem, Doripenem, Cefotaxim, Ceftazidim, Ciprofloxacin, Valaciclovir, efavirenz, emtricitabin, tenofovirdisoproxil, Rilpivirine, penicillin, Trimethoprim-sulfamethoxazole, rifampicin, etambutol, isoniazid, pyrazinamide, voriconazole, amphotericin B, caspofungin, flucytosine, itraconazole, doxycyclin, sulfonamides, and sulfamethoxazole, vancomycin, polymyxin B, polymyxin E, Enoxacin, Norfloxacin, Ofloxacin Levofloxacin, Moxifloxacin, Nadifloxacin, Lomefloxacin, Fleroxacin, Gatifloxacin, Grepafloxacin, Pefloxacin, Sparfloxacin, Temafloxacin, Trovafloxacin, Danofloxacin, Enrofloxacin, Ibafloxacin, Marbofloxacin, Orbifloxacin.

The drugs are included in the composition in an amount sufficient to achieve a desired effect. The amount of drug or biologically active agent incorporated into the composition depends upon the desired release profile, the concentration of drug required for a biological effect, and the desired period of release of the drug. The biologically active substance is typically present in the composition in the range from about 0.5 percent to about 20 percent by weight relative to the total weight of the composition, and more typically, between approximately 1 percent to about 15 percent by weight. Another preferred range is from about 2 percent to about 10 percent by weight. For very active agents, such as growth factors, preferred ranges are less than 1% by weight, and less than 0.0001%.

Use of the Formulation as a Tissue Sealant

The present invention also provides the formulation as defined hereinabove for use as a tissue sealant, e.g. for needle canals formed by biopsy in conjunction with an imaging procedure according to the invention.

The tissue sealant may include an effective amount of a hemostatic agent, e.g. an agent selected from coagulation factors, coagulation initiators, platelet activators, vasoconstrictors and fibrinolysis inhibitors, e.g. epinephrine, adrenochrome, collagens, thrombin, fibrin, fibrinogen, oxidized cellulose and chitosan.

Specific Embodiments of the Invention as an X-Ray Contrast Composition

The present invention is in one embodiment an X-ray contrast composition for local administration, wherein the X-ray contrast composition exhibits contrast properties and wherein at least 60% of an administered amount of said X-ray contrast composition remains more than 24 hours within 10 cm from an injection point when the X-ray contrast composition is administered to a human or animal body. There are of course various forms of injection patterns possible and ways of injecting, such as, but not limited to, transcutane injection, using a scope (bronchoscope, gastroscope, or any other flexible wired systems used to navigate inside a body), attached to another such system, intracranial injection, inside air and fluent filled organs or cavities (e.g. bladder, stomach).

Further, there are various forms of dosing such as, but not limited to, fast injections ('bolus'), pulling back to needle while injecting, slowly injection on the site, pushing the needle forward, and pump giving a constant pressure for a defined period. Furthermore, there are various devices that may be used such as, but not limited to, needle with 1 or more holes on the side of the needle forming multiple smaller objects, flexible, multiple chamber systems.

In one embodiment, the present invention has gelating properties and is a liquid before administration and has the ability to transform into a gel after administration. In one specific embodiment, the present invention has gelating properties and is a homogeneous liquid before administration and has the ability to transform into a gel after administration. Furthermore, in one embodiment the present invention is a non-colloidal x-ray contrast agent as part of a homogeneous liquid x-ray contrast composition that gels upon injection into a human or animal subject. In yet another specific embodiment the X-ray contrast composition is a liquid before administration into a human or animal body that increases in viscosity by more than 10,000 centipoise (cP) after administration into a human or animal body. In another specific embodiment the present invention has a viscosity of less than 10,000 centipoise (cP) at 20° C.

Furthermore, from one perspective, the present invention, the X-ray contrast composition comprises an X-ray contrast agent that is part of the X-ray contrast composition and said X-ray contrast agent is an organic substance.

It is the organic substance that is being the contrast "agent" and in one specific embodiment the X-ray contrast composition comprises alginate and chitosan. In another specific embodiment the X-ray contrast agent comprises one or more natural polymers, synthetic polymers, oligomers, lipids, saccharides, disaccharides, polysaccharides, peptides or any combination thereof and as mentioned before these may be the contrast "agent". In yet another specific embodiment of the present invention the X-ray contrast agent comprises one or more iodinated polymers, oligomers, lipids, saccharides, disaccharides, polysaccharides, peptides, or a derivative or a combination thereof. Further, in one embodiment the X-ray contrast agent is an inorganic acid or salt, such as chloroauric acid.

The present invention may in one embodiment comprise particles for various purposes. One purpose may be an additive contrast effect; another purpose may be to potentiating the effect and a third purpose may be as a carrier of e.g. medication or other substances. According to one specific embodiment of the present invention, the X-ray contrast composition comprises nanoparticles comprising gold (Au). In yet another embodiment the X-ray contrast composition also comprises particles in the size range from 1-1000 nm, such as nanoparticles in the size range from 2 to 500 nm and in one specific embodiment the nanoparticles comprises gold (Au) which furthermore is the most likely substance. In yet another embodiment, the X-ray contrast composition comprising nanoparticle that may be an MRI, PET, ultrasound, fluorescence, radiofrequency, visible light contrast agent. Furthermore, in one specific embodiment the nanoparticle is an MRI or PET contrast agent or a combination of the above mentioned imaging modalities.

As mentioned previously the present invention may have gelating properties and the gelling may be initiated by various factors such as, but not limited to, temperature, hydration, enzymatic activation, ion concentration and/or pH. In one embodiment the X-ray contrast composition exhibits gel-formation in response to a temperature in the range of 35 to 40° C. In another embodiment the X-ray contrast composition exhibits gel-formation in response to hydration. In yet another embodiment the X-ray contrast composition exhibits gel-formation in response to an ion-concentration in the range of 1 µM to 500 mM, such as in the range of 1 mM to 200 mM. In one embodiment the ions are divalent ions, such as calcium ions. In one embodiment the X-ray contrast composition exhibits gel-formation in response to a pH in the range of 6 to 8. In yet another embodiment, the X-ray contrast composition exhibits gel-formation in response to contacting with an initiator and here an initiator can be many different things such as, but not limited to, ions, or a chemical reactive compound that cross link other molecules.

In one embodiment, the X-ray contrast composition according to the present invention may comprise radioactive compounds, paramagnetic compounds, fluorescent compounds or ferromagnetic compounds, or any mixture thereof.

As mentioned previously, the X-ray contrast composition may also act as a carrier of substances such as, but not limited to, pharmaceutical substances. The substance may be in the composition or in or coated/linked to the nanoparticles. The substance may also be other types of additives. Examples of substance could be, but is not limited to, substances suitable for chemotherapy, gemcitabine, cisplatin, doxorubicin, doranidazole, hormones or anti-bodies. In one embodiment the X-ray composition comprise at least one pharmaceutical substance. In one specific embodiment the X-ray contrast composition comprises particles in the size range from 1-1000 nm, such as nanoparticles in the size range from 2 to 500 nm and wherein the particle contains at least one pharmaceutical substance.

In one embodiment a polymer may be used to work as a stabilizer between gel and biological surrounding and therefore, the X-ray contrast composition may also comprises a molecule that increase gel stability in the human or animal body, such as an amphiphilic molecule, such as an emulsifier. Therefore in one embodiment the X-ray contrast composition comprises poly(ethylene glycol-b-caprolactone) (PEG-PCL), sucrose acetate isobutyrate (SAIB), poly(D,L-lactic acid) (PLA), or poly(lactic-co-glycolic acid) (PGLA), or a combination thereof. In one embodiment of the present invention poly(D,L-lactic acid) (PLA) is added to sucrose acetate isobutyrate (SAIB) gel causing a reduction of burst release of said encapsulated contents e.g. particles drugs etc. Further, in one embodiment, the X-ray contrast composition comprises sucrose acetate isobutyrate (SAIB) or a derivative thereof and in one specific embodiment of the present invention, the X-ray contrast composition comprises an iodinated derivate of sucrose acetate isobutyrate (SAIB). Furthermore in another specific embodiment of the present invention the X-ray contrast composition comprises an iodinated derivate of sucrose acetate isobutyrate (SAIB) doped into sucrose acetate isobutyrate (SAIB). This has been evaluated for stability and the amount of this iodo-SAIB/SAIB that can be doped into SAIB, is at least 50 mol %.

The iodo-SAIB provides high X-ray contrast. The iodo-SAIB compound is poorly soluble in ethanol and is a white solid whereas SAIB is highly soluble in ethanol and is a thick oil. However, a mixture of ethanol and SAIB can solubilize the iodo-SAIB very nicely. This means that the SAIB helps solubility of iodo-SAIB, which is an interesting feature and which provides an injectable solution which gelates after administration (through a thin needle, thinner than 20 gauge) that can function as a high contrast X-ray marker. When injected into mice, the iodo-SAIB/SAIB provides high contrast and has the desirable stability properties. Furthermore, the gel seems homogeneous. In one embodiment of the present invention the X-ray contrast composition comprises an iodinated derivate of sucrose acetate isobutyrate (SAIB) solubilised in a mixture of ethanol and sucrose acetate isobutyrate (SAIB).

One way of containing and also storing the composition may be, held in the interior of a syringe. This indicates a possible shelf-life of at least 6 months. One embodiment of the present invention is a kit comprising a syringe, a hypodermal needle adapted to the open end of said syringe, and a composition according to any one of the preceding claims.

The intended use of the present invention is for radio therapy or image-guided radio therapy, but not exclusively, other uses are thinkable such as, but not limited to, 2D X-ray scans, for use in imaging, diagnostics, treatment and/or quality rating of radio therapy. The present invention may be used as a tissue marker and/or for use as a controlled drug release composition.

In one embodiment the X-ray contrast composition according to the present invention is for use in administration of an amount of 0.01-5.0 mL and in one specific embodiment the X-ray contrast composition is for use in administration wherein the amount is 0.1-1.0 mL. In one embodiment the present invention may be used as a tissue sealant.

Methods for Treatment of Cancer

In one embodiment, the present invention relates to treatment of cancerous diseases associated with malignant neoplasia such as malignant neoplasm of lip, mouth or throat, such as malignant neoplasm of the tongue, the base of tongue, gum, floor of mouth, palate, parotid gland, major salivary glands, tonsil, oropharynx, nasopharynx, piriform sinus, hypopharynx or other parts of lip, mouth or throat or malignant neoplasms of digestive organs such as malignant neoplasms of oesophagus, stomach, small intestine, colon, rectosigmoid junction, rectum, anus and anal canal, liver and intrahepatic bile ducts, gallbladder, other parts of biliary tract, pancreas and spleen, malignant neoplasms of respiratory and intrathoracic organs such as malignant neoplasms of the nasal cavity and middle ear, accessory sinuses, larynx, trachea, bronchus and lung, thymus, heart, mediastinum and pleura, malignant neoplasms of bone and articular cartilage such as malignant neoplasm of bone and articular cartilage of limbs, bone and articular cartilage, malignant melanoma of skin, sebaceous glands and sweat glands, malignant neoplasms of mesothelial and soft tissue such as malignant neoplasm of mesothelioma, Kaposi's sarcoma, malignant neoplasm of peripheral nerves and autonomic nervous system, malignant neoplasm of retroperitoneum and peritoneum, malignant neoplasm of connective and soft tissue such as blood vessels, bursa, cartilage, fascia, fat, ligament, lymphatic vessel, muscle, synovia, tendon, head, face and neck, abdomen, pelvis or overlapping lesions of connective and soft tissue, malignant neoplasm of breast or female genital organs such as malignant neoplasms of vulva, vagina, cervix uteri, corpus uteri, uterus, ovary, Fallopian tube, placenta or malignant neoplasms of male genital organs such as malignant neoplasms of penis, prostate, testis, malignant neoplasms of the urinary tract, such as malignant neoplasms of kidney, renal pelvis, ureter, bladder, urethra or other urinary organs, malignant neoplasms of eye, brain and other parts of central nervous system such as malignant neoplasm of eye and adnexa, meninges, brain, spinal cord, cranial nerves and other parts of central nervous system, malignant neoplasms of thyroid and other endocrine glands such as malignant neoplasm of the thyroid gland, adrenal gland, parathyroid gland, pituitary gland, craniopharyngeal duct, pineal gland, carotid body, aortic body and other paraganglia, malignant neoplasms of head, face and neck, thorax, abdomen and pelvis, secondary malignant neoplasm of lymph nodes, respiratory and digestive organs, kidney and renal pelvis, bladder and other and urinary organs, secondary malignant neoplasms of skin, brain, cerebral meninges, or other parts of nervous system, bone and bone marrow, ovary, adrenal gland, malignant neoplasms of lymphoid, haematopoietic and related tissue such as Hodgkin's disease, follicular non-Hodgkin's lymphoma, diffuse non-Hodgkin's lymphoma, peripheral and cutaneous T-cell lymphomas, non-Hodgkin's lymphoma, lymphosarcoma, malignant immunoproliferative diseases such as Waldenstrom's macroglobulinaemia, alpha heavy chain disease, gamma heavy chain disease, immunoproliferative small intestinal disease, multiple myeloma and malignant plasma cell neoplasms such as plasma cell leukaemia, plasmacytoma, solitary myeloma, lymphoid leukaemia such as acute lymphoblastic leukaemia, myeloid leukaemia, monocytic leukaemia, blast cell leukaemia, stem cell leukaemia, and other and unspecified malignant neoplasms of lymphoid, haematopoietic and related tissue such as Letterer-Siwe disease, malignant histiocytosis, malignant mast cell tumour, true histiocytic lymphoma or other types of malignant neoplasia.

According to the present invention, treatment of carcinoma in situ of oral cavity, oesophagus, stomach, digestive organs, middle ear and respiratory system, melanoma in situ, carcinoma in situ of skin, carcinoma in situ of breast, carcinoma in situ of female or male genitals, carcinoma in situ of bladder, urinary organs or eye, thyroid and other endocrine glands, or other types of carcinoma in situ.

Specific Embodiments of the Invention for Use in HIFU/Proton Therapy:

Advances in modern radiation techniques have enabled increasingly conformal radiotherapy from three-dimensional conformal radiotherapy to intensity modulated radiotherapy (IMRT) and proton therapy. These techniques minimizes dose to organs at risk and may enable dose escalation. Dose escalation prerequisites accurate and reproducible patient positioning and target alignment as poor targeting accuracy may compromise local tumor control and increase the risk of radiation induced toxicity.

In image-guided radiation therapy (IGRT) with 2D-(kV-radiographs) or 3D x-ray (cone beam computed tomography (CT)) images are recorded before and sometimes during treatment. Alignments to bony anatomy or soft tissue are used depending on the anatomical characteristics of the target. In some clinical cases the target position does not correlate well with neither bony nor soft tissue anatomy, e.g. prostate cancer and lung tumors adjacent to the mediastinum. In these cases target localization can be enhanced by alignment to radiopaque fiducial markers implanted in or near the target.

Fiducial markers are routinely being used in connection with photon radiotherapy. However, use of fiducial markers in proton radiotherapy has been approached with care as their presence can cause extreme perturbations in the therapeutic proton dose, which translates into significant colds spots downstream from the fiducial marker.

Perturbations in the proton beam for a variety of solid fiducial markers of different material have been investigated showing dose perturbations up to 80% of the prescribed dose (4-10) ENREF 2 ENREF 2. Generally, small markers composed of low Z-materials yields the lowest dose perturbation. However, clinical relevant dose perturbation has been reported for solid markers less than one millimeter in size. Consequently, both the actual marker size and position must be correctly accounted for in the proton treatment planning system, especially if the marker is located inside the treatment field.

The ideal fiducial marker for proton therapy is visible in CT- or kV imaging, causes no dose perturbation in a proton beam and do not induce image artifacts on the CT-images used for treatment planning. Liquid markers have properties that are promising in this regard. A liquid marker is a radiopaque fluid that is injected into the tissue. In one embodiment the present invention is a composition wherein the composition is a fiducial marker for proton therapy. In another embodiment the present invention is a composition further comprising a contrast agent that makes the composition visible by CT or kV imaging.

High intensity focused ultrasound (HIFU, or sometimes MRgFUS for magnetic resonance guided focused ultrasound) is a medical procedure that applies high intensity focused ultrasound energy to locally heat and destroy diseased or damaged tissue through ablation.

HIFU is a hyperthermia therapy, a class of clinical therapies that use temperature to treat diseases. HIFU is also one modality of therapeutic ultrasound, involving minimally invasive or non-invasive methods to direct acoustic energy into the body. In addition to HIFU, other modalities include ultrasound-assisted drug delivery, ultrasound hemostasis, ultrasound lithotripsy, and ultrasound-assisted thrombolysis.

Clinical HIFU procedures are typically performed in conjunction with an imaging procedure to enable treatment planning and targeting before applying a therapeutic or ablative levels of ultrasound energy. When Magnetic Resonance Imaging (MRI) is used for guidance, the technique is sometimes called Magnetic Resonance guided Focused Ultrasound, often shortened to MRgFUS or MRgHIFU.

In one embodiment the present invention is a composition wherein the composition comprises contrast agents that makes the composition visible by High intensity focused ultrasound (HIFU). In another embodiment of the invention the composition comprises agents that enhance the therapeutic effect of HIFU when HIFU is used to treat diseased tissue.

Specific Embodiments of the Invention for use in PET Imaging:

Positron emission tomography (PET) is a modern and powerful technology to study non-invasively biological processes at the molecular level. This highly sophisticated imaging method relies on coincidence registration of annihilation photons having a characteristic energy of 511 keV. There is a wide range of positron-emitting halogens available; $^{18}F$, $^{75}Br$, $^{76}Br$, and $^{124}I$ which have been reported to be useful for applications in oncology—with $^{18}F$ as the most prominent among them. Generally, the decay of $^{75}Br$, $^{76}Br$, and $^{124}I$ results in positrons of higher energy compared with $^{18}F$. This means a loss in spatial resolution since the positrons take a longer distance in tissue until annihilation. These alternative radiohalogens also emit γ-rays of high energy resulting from electron capture ($^{75}Br$, $^{76}Br$, $^{124}I$) and internal transitions ($^{124}I$). Table 1 compares some selected physical properties of these radioisotopes.

TABLE 1

Physical properties of isotopes used in PET-imaging.

| Radio nuclide | $t_{1/2}$ | Ratio of β+ (%) | E (β+ max) | γ energy per decay (MeV) | Effective dose constant (μSv/MBq h) |
|---|---|---|---|---|---|
| $^{18}F$ | 110 in | 97 | 0.635 | — | 5.37 |
| $^{75}Br$ | 97 min | 91 | 1.74 | 0.473 | 7.85 |
| $^{76}Br$ | 16.2 h | 54 | 3.98, 3.44, | 2.226 | 12.5 |
| $^{124}I$ | 4.15 days | 23 | 2.13, 1.53, 0.808 | 0.852 | 4.91 |

18F can be produced using three different nuclear reactions, shown in Table 2. However, in practice only the $^{20}Ne(d,\alpha)$ and $^{18}O(p,n)$ processes are relevant. Because of its high target yield the $^{18}O(p,n)$ route has become the favored reaction. No-carrier-added (n.c.a.) $^{18}F$ is obtained from proton irradiation of $^{18}O$-enriched medium.

TABLE 2

Production routes for $^{18}F$

| Nuclear reaction | Energy range (MeV) | Theoretical thick target yield (MBq/μAh) |
|---|---|---|
| $^{20}Ne(d,\alpha)^{18}F$ | 14→0 | 1110 |
| $^{18}O(p,n)^{18}F$ | 16→3 | 2960 |
| $^{16}O(^{3}He,p)^{18}F$ | 41→14 | 481 |

PET-Imaging in Connection with Proton Therapy:

Positron emission tomography (PET) is potentially a very useful tool for monitoring the distribution of the dose deposited in the patient from proton therapy. This method is based on the detection of the positron-annihilation γ-rays following the decay of the small amounts of positron emitters (typically $^{11}C$ (t½=20.39 min), $^{13}N$ (t½=9.96 min) and $^{15}O$ (t½=2.04 min)) produced via non-elastic nuclear reaction of protons with the target nuclei of the irradiated tissue. Verification of the therapy can be achieved by comparing the PET images discerning the positron activity distribution with the predicted target dose distribution used to plan the treatment. The expected number of nuclear reactions is governed by three factors: nuclear reaction cross sections, the number of incoming particles limited by target dose, and the number of target particles.

Using isotopes produced during normal proton irradiation of soft tissue in problematic due to the short half-life of the $^{11}C$, $^{13}N$ and $^{15}O$ (FIG. 1), which often requires in-beam PET scanner and complex data analysis following data accusation. Furthermore, using natural isotopes is challenged by biological wash-out from proton irradiation to PET-imaging increasing the uncertainty of the measurements.

Accurate estimation of the Bragg-peak-distal-edge (BPDE) location is crucial in proton therapy dose delivery in order to verify that undershooting and overshooting is not introduced due to change in patient anatomy, motion etc. Current range verification techniques includes PET imaging which takes advantage of the β+ emitters produced following proton interaction within the patient body. However, such interactions produce negligible PET signal at the BPDE due largely to the decrease in proton energy with depth, which reduces the efficiency of β+ emitter production.

Inclusion of $^{18}O$ the present invention that is as a component in any composition described as well as sucrose based compositions and BioXmark™ as $[18O]_6$-sucrose octaacetate, or derivatives hereof facilitates the $^{18}O(p,n)^{18}F$ nuclear reaction in vivo resulting in formation of $^{18}F$ which can be detected using PET-imaging. The $^{18}O(p,n)^{18}F$ reaction benefits from having a low interaction energy threshold which enables monitoring of small proton doses, giving possibilities for radiation dose evaluation. Furthermore, the formed $^{18}F$ has a sufficient half-life for patient monitoring.

A marker, which does not introduce dose perturbation in proton beams, is clearly visible for patient alignment/motion management and at the same time can provide dosimetric output regarding the BPDE would be highly beneficial for the proton community.

In one embodiment the present invention is a composition wherein the composition comprises contrast agents that makes the composition visible by PET. In another embodiment the present invention is a composition further comprising $^{18}O$.

A Kit Comprising the Formulation

The present invention further comprises a kit comprising a syringe, a hypodermal needle adapted to the open end of said syringe, and a formulation as defined hereinabove. In one embodiment, the formulation is held in the interior or said syringe.

The gel forming system may be provided as a lyophilized powder, a suspension or a solution. Different components may be provided in one or more individual vials or pre-mixed in the interior or said syringe. Exemplary different components include, but are not limited to, the gel-forming system and the solid particles, and the formulation and one or more initiators.

The syringe may consist of a single, a multiple barrel syringe (e.g. MEDMIX SYSTEMS AG) or a double champer syringe (e.g. Debiotech S.A.) and the like, but not limited to those. Multiple barrel syringes and double champer syringes and the like may be useful for e.g. two components formulations were one component is a mixture of the gel forming system, the active pharmaceutical ingredient and potentially a contrast agent(s) and the other component is an initiator or salt suspension. In another embodiment a double chamber syringe may be useful where one chamber contains gel-forming component and the contrast agent(s) and the other chamber the active pharmaceutical ingredient(s).

The needle of the syringe can, in some embodiments, be one suitable for fine-needle biopsies. Non-limiting examples of syringes and needles for such embodiments are described in U.S. Pat. No. 7,871,383, U.S. patent publication No. 20040162505, and references cited therein. Such syringes and needles can advantageously be used in procedures where a biopsy of a tissue is to be taken in conjunction with imaging of the same, using a formulation of the invention. Preferably, the kit has a shelf-life of at least 6 months, such as at least 12 months when stored at, e.g., room temperature (typically 18 to 25° C.) or lower temperatures, such as, e.g., 2 to 10° C., such as about 5° C. The shelf-life can, for example, be determined as the period wherein the kit can be stored at 25° C., at 80% RH and 1 atm. pressure, and where the viscosity is kept within ±5% of the initial viscosity.

Structures

In a particular embodiment, the invention includes compositions wherein the gel has a structure selected from the group consisting of:

Monosaccaharides:
D-Glucosamine Derivatives:

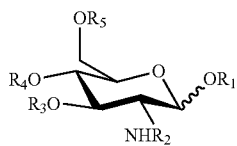

wherein $R_1$, $R_2$, $R_3$, $R_4$ and $R_5$ are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$ and $R_5$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl, carbohydrates and carbohydrate derivatives;

wherein all groups of $R_1$, $R_2$, $R_3$, $R_4$ and $R_5$ are selected collectively from the group consisting of acetyl, isobutyryl or propionyl; or wherein $R_1$, $R_2$, $R_3$, $R_4$ and $R_5$ are independently selected from the group consisting acetyl, isobutyryl or propionyl;

and wherein both pure anomers and mixtures of α- and β-anomers of the above mentioned structural variations are claimed.

Disaccharides:

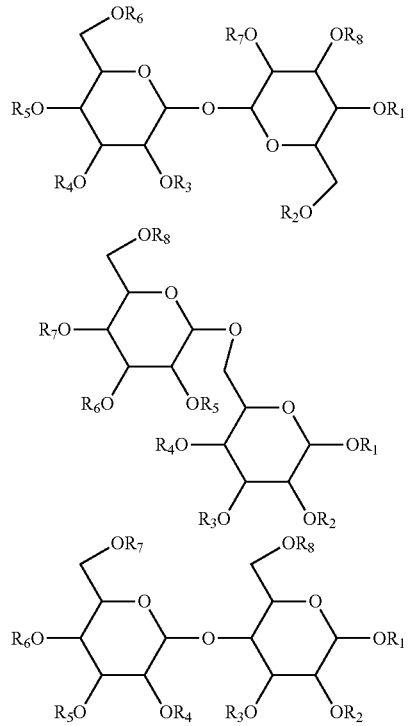

wherein $R_1$, $R_2$, $R_3$, $R_4$, $R_5$, $R_6$, $R_7$, and $R_8$ are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, and $R_8$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

wherein all groups of $R_1$, $R_2$, $R_3$, $R_4$, $R_5$, $R_6$, $R_7$, and $R_8$ are selected collectively from the group consisting of acetyl, isobutyryl or propionyl; or wherein $R_1$, $R_2$, $R_3$, $R_4$, $R_5$, $R_6$, $R_7$, and $R_8$ are independently selected from the group consisting acetyl, isobutyryl or propionyl;

and wherein both pure anomers and mixtures of α- and β-anomers of the above mentioned structural variations are claimed.

Lactose Derivatives:

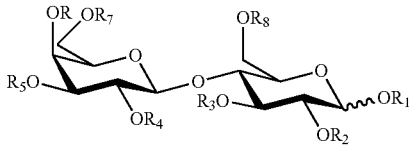

wherein $R_1$, $R_2$, $R_3$, $R_4$, $R_5$, $R_6$, $R_7$, and $R_8$ are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, and $R_8$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

wherein all groups of $R_1$, $R_2$, $R_3$, $R_4$, $R_5$, $R_6$, $R_7$, and $R_8$ are selected collectively from the group consisting of acetyl, isobutyryl or propionyl; or wherein $R_1$, $R_2$, $R_3$, $R_4$, $R_5$, $R_6$, $R_7$, and $R_8$ are independently selected from the group consisting acetyl, isobutyryl or propionyl;

and wherein both pure anomers and mixtures of α- and β-anomers of the above mentioned structural variations are claimed.

Trehalose Derivatives:

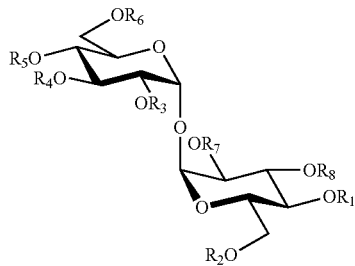

wherein $R_1$, $R_2$, $R_3$, $R_4$, $R_5$, $R_6$, $R_7$, and $R_8$ are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, and $R_8$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

wherein all groups of $R_1$, $R_2$, $R_3$, $R_4$, $R_5$, $R_6$, $R_7$, and $R_8$ are selected collectively from the group consisting of acetyl, isobutyryl or propionyl; or wherein $R_1$, $R_2$, $R_3$, $R_4$, $R_5$, $R_6$, $R_7$, and $R_8$ are independently selected from the group consisting acetyl, isobutyryl or propionyl;

and wherein both pure anomers and mixtures of α- and β-anomers of the above mentioned structural variations are claimed.

Maltose Derivatives:

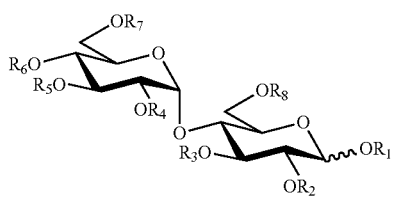

wherein $R_1$, $R_2$, $R_3$, $R_4$, $R_5$, $R_6$, $R_7$, and $R_8$ are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, and $R_8$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

wherein all groups of $R_1$, $R_2$, $R_3$, $R_4$, $R_5$, $R_6$, $R_7$, and $R_8$ are selected collectively from the group consisting of acetyl, isobutyryl or propionyl; or wherein $R_1$, $R_2$, $R_3$, $R_4$, $R_5$, $R_6$, $R_7$, and $R_8$ are independently selected from the group consisting acetyl, isobutyryl or propionyl;

and wherein both pure anomers and mixtures of α- and β-anomers of the above mentioned structural variations are claimed.

Trisaccharides:

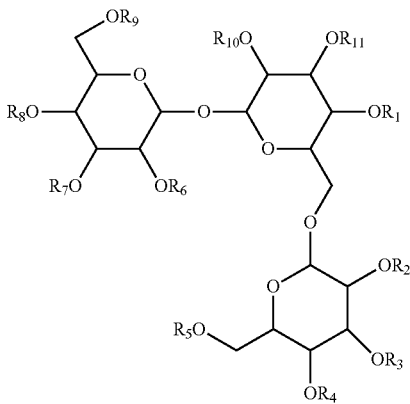

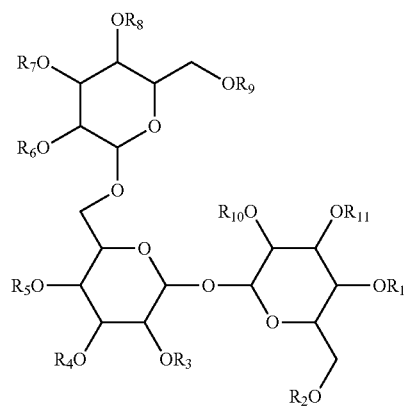

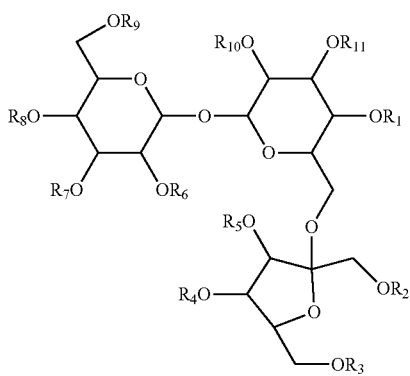

33
-continued
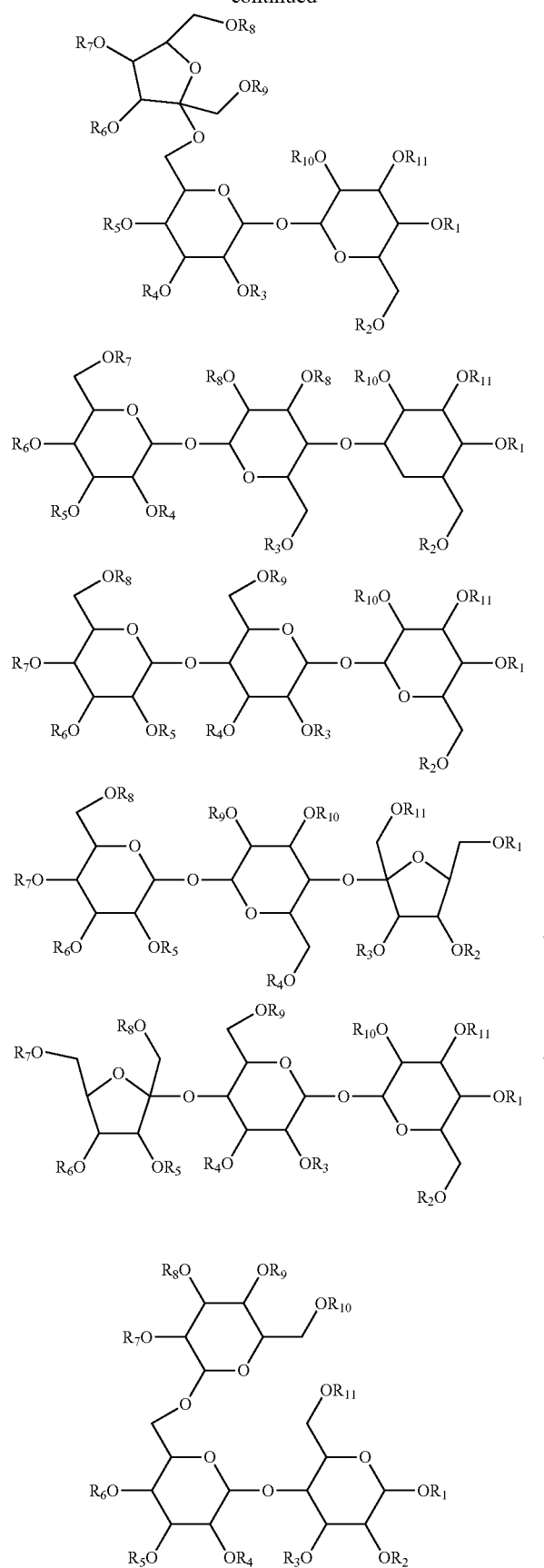
34
-continued
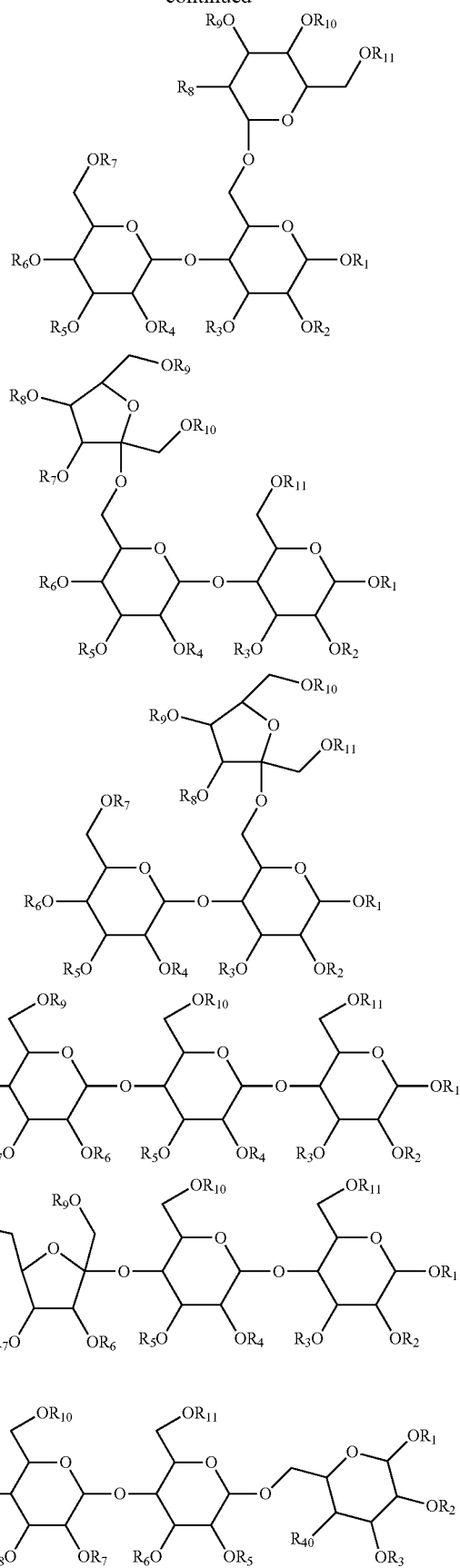

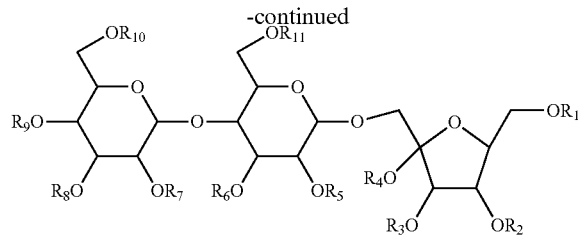

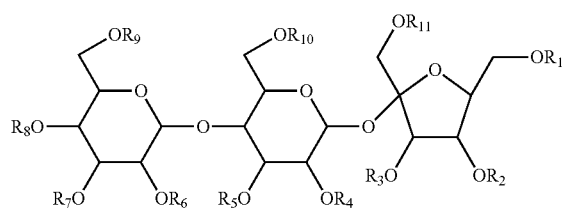

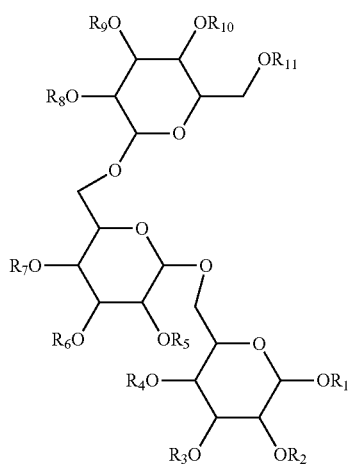

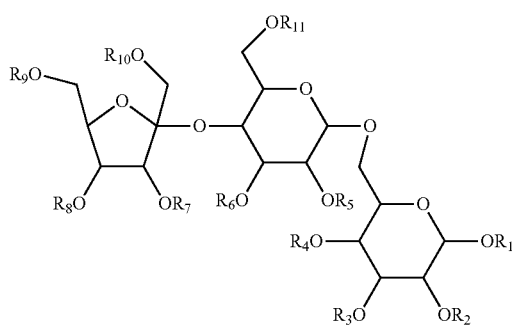

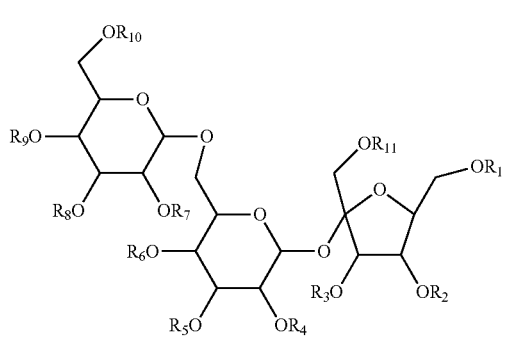

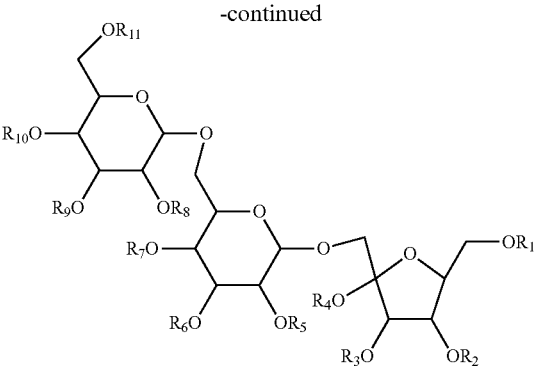

wherein $R_1$, $R_2$, $R_3$, $R_4$, $R_5$, $R_6$, $R_7$, $R_8$, $R_9$, $R_{10}$ and $R_{11}$ are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, $R_8$, $R_9$, $R_{10}$ and $R_{11}$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl; wherein all groups of $R_1$, $R_2$, $R_3$, $R_4$, $R_5$, $R_6$, $R_7$, $R_8$, $R_9$, $R_{10}$ and $R_{11}$ are selected collectively from the group consisting of acetyl, isobutyryl or propionyl; or wherein $R_1$, $R_2$, $R_3$, $R_4$, $R_5$, $R_6$, $R_7$, $R_8$, $R_9$, $R_{10}$ and $R_{11}$ are independently selected from the group consisting acetyl, isobutyryl or propionyl;

and wherein both pure anomers and mixtures of α- and β-anomers of the above mentioned structural variations are claimed.

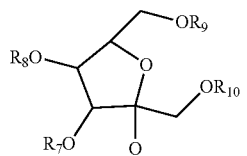

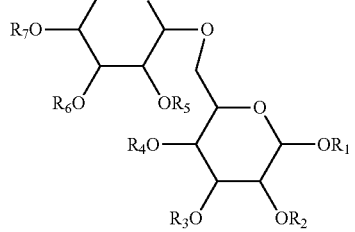

wherein $R_1$, $R_2$, $R_3$, $R_4$, $R_5$, $R_6$, $R_7$, $R_8$, $R_9$ and $R_{10}$ are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, $R_8$, $R_9$ and $R_{10}$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;
wherein all groups of $R_1$, $R_2$, $R_3$, $R_4$, $R_5$, $R_6$, $R_7$, $R_8$, $R_9$ and $R_{10}$ are selected collectively from the group consisting of acetyl, isobutyryl or propionyl; or
wherein $R_1$, $R_2$, $R_3$, $R_4$, $R_5$, $R_6$, $R_7$, $R_8$, $R_9$ and $R_{10}$ are independently selected from the group consisting acetyl, isobutyryl or propionyl;

and wherein both pure anomers and mixtures of α- and β-anomers of the above mentioned structural variations are claimed.

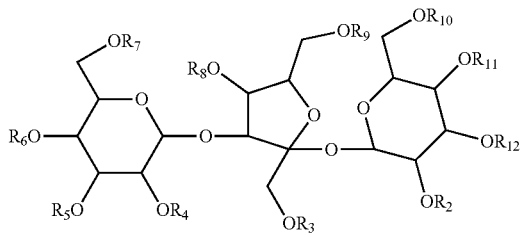

wherein $R_1$, $R_2$, $R_3$, $R_4$, $R_5$, $R_6$, $R_7$, $R_8$, $R_9$, $R_{10}$, $R_{11}$ and $R_{12}$ are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, $R_8$, $R_9$, $R_{10}$, $R_{11}$ and $R_{12}$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

wherein all groups of $R_1$, $R_2$, $R_3$, $R_4$, $R_5$, $R_6$, $R_7$, $R_8$, $R_9$, $R_{10}$, $R_{11}$ and $R_{12}$ are selected collectively from the group consisting of acetyl, isobutyryl or propionyl; or wherein $R_1$, $R_2$, $R_3$, $R_4$, $R_5$, $R_6$, $R_7$, $R_8$, $R_9$, $R_{10}$, $R_{11}$ and $R_{12}$ are independently selected from the group consisting acetyl, isobutyryl or propionyl;

and wherein both pure anomers and mixtures of α- and β-anomers of the above mentioned structural variations are claimed.

Raffinose Derivatives:

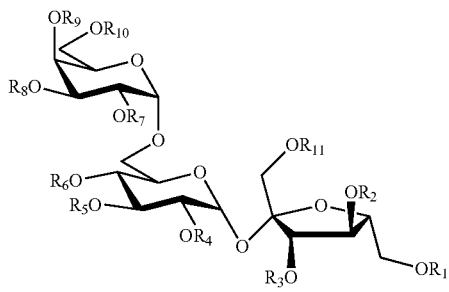

wherein $R_1$, $R_2$, $R_3$, $R_4$, $R_5$, $R_6$, $R_7$, $R_8$, $R_9$, $R_{10}$ and $R_{11}$ are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, $R_8$, $R_9$, $R_{10}$ and $R_{11}$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

wherein all groups of $R_1$, $R_2$, $R_3$, $R_4$, $R_5$, $R_6$, $R_7$, $R_8$, $R_9$, $R_{10}$ and $R_{11}$ are selected collectively from the group consisting of acetyl, isobutyryl or propionyl; or wherein $R_1$, $R_2$, $R_3$, $R_4$, $R_5$, $R_6$, $R_7$, $R_8$, $R_9$, $R_{10}$ and $R_{11}$ are independently selected from the group consisting acetyl, isobutyryl or propionyl;

and wherein both pure anomers and mixtures of α- and β-anomers of the above mentioned structural variations are claimed.

Specific Embodiments of the Invention

One embodiment of the present invention relates to a composition comprising non-water soluble carbohydrates, wherein at least 50% of the non-water soluble carbohydrates are carbohydrates selected from derivatives of lactose, maltose, trehalose, raffinose, glucosamine, galactosamine, lactosamine, or derivatives of disaccharides with at least two pyranose saccharide units, trisaccharides, tetrasaccharides, or mixtures thereof, and wherein the composition is a liquid before administration into the human or animal body and increases in viscosity by more than 1,000 centipoise (cP) after administration, for use as a medicament. Another embodiment relates to a composition for use as a controlled release system of one or more active pharmaceutical ingredients in a human or animal body. One embodiment relates to a composition for use as a controlled release system, wherein the composition is a liquid before administration into the human or animal body that increases in viscosity by more than 10,000 centipoise (cP) after administration into the human or animal body. One embodiment relates to a composition for use as a controlled release system, wherein the composition is a liquid before administration and has the ability to transform into a gel-like material after administration. One embodiment relates to a composition for use as a controlled release system, wherein the composition becomes a solid after administration, such as a crystalline or amorphous solid. One embodiment relates to a composition for use as a controlled release system, wherein an increase in viscosity after administration into the human or animal body is due to diffusion of a molecule out of the administered material and into surrounding tissue. One embodiment relates to a composition for use as a controlled release system, wherein an increase in viscosity after administration into the human or animal body is due to diffusion of solvent-like molecules. One embodiment relates to a composition for use as a controlled release system, wherein the non-water soluble carbohydrates are disaccharides with structures selected from:

Formulae I

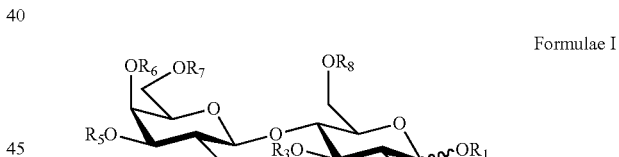

II

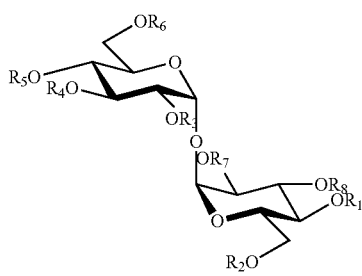

III

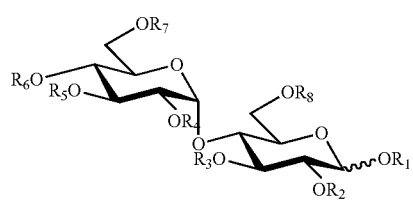

wherein $R_1$, $R_2$, $R_3$, $R_4$, $R_5$, $R_6$, $R_7$, and $R_8$ in formulae I, II and III are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, and $R_8$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

or wherein all groups of $R_1$, $R_2$, $R_3$, $R_4$, $R_5$, $R_6$, $R_7$, and $R_8$ are selected collectively from the group consisting of acetyl, isobutyryl or propionyl; or wherein $R_1$, $R_2$, $R_3$, $R_4$, $R_5$, $R_6$, $R_7$, and $R_8$ are independently selected from the group consisting acetyl, isobutyryl or propionyl;

and wherein both pure anomers and mixtures of α- and β-anomers of the above mentioned structural variations are claimed.

One embodiment relates to a composition for use as a controlled release system, wherein the non-water soluble carbohydrates are trisaccharides with structures selected from:

Formulae IV

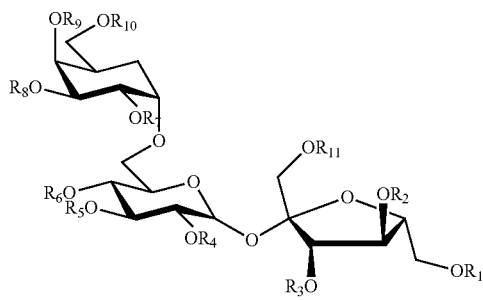

wherein $R_1$, $R_2$, $R_3$, $R_4$, $R_5$, $R_6$, $R_7$, $R_8$, $R_9$, $R_{10}$ and $R_{11}$ in formulae IV are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, $R_8$, $R_9$, $R_{10}$ and $R_{11}$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

or wherein all groups of $R_1$, $R_2$, $R_3$, $R_4$, $R_5$, $R_6$, $R_7$, $R_8$, $R_9$, $R_{10}$ and $R_{11}$ are selected collectively from the group consisting of acetyl, isobutyryl or propionyl; or wherein $R_1$, $R_2$, $R_3$, $R_4$, $R_5$, $R_6$, $R_7$, $R_8$, $R_9$, $R_{10}$ and $R_{11}$ are independently selected from the group consisting acetyl, isobutyryl or propionyl;

and wherein both pure anomers and mixtures of α- and β-anomers of the above mentioned structural variations are claimed.

One embodiment relates to a composition for use as a controlled release system, wherein at least 50% of the non-water soluble carbohydrates are mono- or oligosaccharides containing at least one amino sugar unit. One embodiment relates to a composition for use as a controlled release system, wherein the amino sugar has the structure:

Formulae V

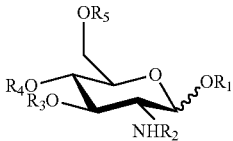

wherein $R_1$, $R_2$, $R_3$, $R_4$ and $R_5$ in formulae V are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$ and $R_5$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl, and mono-, di-, tri- or tetra-saccharide derivatives;

or wherein all groups of $R_1$, $R_2$, $R_3$, $R_4$ and $R_5$ are selected collectively from the group consisting of acetyl, isobutyryl or propionyl; or wherein $R_1$, $R_2$, $R_3$, $R_4$ and $R_5$ are independently selected from the group consisting acetyl, isobutyryl or propionyl;

and wherein both pure anomers and mixtures of anomers such as α- and β-anomer centres of the above mentioned structural variations are claimed.

One embodiment relates to a composition for use as a controlled release system, wherein the release of one or more active pharmaceutical ingredients is controlled by mixing non-water soluble carbohydrates with different hydrophobicity by alteration of the substitutions on the carbohydrate hydroxyl groups. One embodiment relates to a composition for use as a controlled release system, wherein the active pharmaceutical ingredient is selected from a protein, a peptide, a nucleoprotein, a mucoprotein, a lipoprotein, or a synthetic polypeptide. One embodiment relates to a composition for use as a controlled release system, wherein the active pharmaceutical ingredient is selected from a protein, which is a human growth hormone, fibroblast growth factor (FGF), erythropoietin (EPO), platelet derived growth factor (PDGF), granulocyte colony stimulating factor (g-CSF), bovine somatotropin (BST), tumor necrosis factor (TNF), transforming growth factor-beta (TGF-Beta), a cytokine, an interleukin, insulin, or interferon. One embodiment relates to a composition for use as a controlled release system, wherein the active pharmaceutical ingredient is selected from nucleic acids, nucleotides, nucleosides, oligonucleotides, DNA, RNA or fragments thereof. One embodiment relates to a composition for use as a controlled release system, wherein the active pharmaceutical ingredient is a small inorganic or organic drug molecule. One embodiment relates to a composition for use as a controlled release system, wherein the active pharmaceutical ingredient is a chemotherapeutic drug for treatment of cancer. One embodiment relates to a composition for use as a controlled release system, wherein the active pharmaceutical ingredients is a chemotherapeutic drug selected from the class of compounds that are anti-metabolites, anti-microtubule agents, topoisomerase inhibitors, cytotoxic antibiotics, alkylating agents, checkpoint inhibitors, or a radiosensitizer, or a photosensitizer. One embodiment relates to a composition for use as a controlled release system, wherein the active pharmaceutical ingredient is a drug that modulates an immune response. One embodiment relates to a composition for use as a controlled release system, wherein the active pharmaceutical ingredient enhances the effect of radiotherapy, photodynamic therapy (PDT), hyperthermia based treatments such as high-intensity focused ultrasound (HIFU), radiofrequency thermal ablation (RFA), laser-therapy, or laser-induced interstitial thermotherapy (LITT). One embodiment relates to a composition for use as a controlled release system, wherein the active pharmaceutical ingredient is an anesthetic.

One embodiment relates to a composition for use as a controlled release system, wherein the active pharmaceutical ingredient is formulated in a nanoparticle or microsphere that is dispersed in the composition. One embodiment relates to a composition for use as a controlled release system, wherein the composition comprises contrast agents that makes the composition visible by PET imaging, SPECT imaging, Ultrasound imaging, CT imaging, x-ray imaging, fluoroscopy imaging, fluorescence imaging, or OCT imaging. One embodiment relates to a composition for use as a controlled release system, wherein the composition comprises organic radioisotopes or inorganic radionuclides for use as internal radiotherapy such as brachytherapy or in imaging of tissue in humans or animals. One embodiment relates to a composition for use as a controlled release system, which is administered to the human or animal body through a syringe, an endoscope or a bronchoscope to the target tissue preferably wherein the composition after insertion into the human or animal body constitutes a medical or surgical implant for tissue or surgical adhesion which preferably is wound dressing, a hemostat, enhances tissue regeneration, is a void filler.

Another aspect of the present relation relates to a medical or surgical implant comprising a composition according to any of the preceding claims, wherein the composition is part of a sprayable composition.

In one embodiment the present invention relates to a composition comprising:
 a. non-water soluble carbohydrates
 b. a contrast agent for imaging, wherein at least 60% of the contrast agent remains within 10 cm from the injection site after 24 h for use in local co-administration into a human or animal body, and wherein the composition is a liquid before administration into the human or animal body and increases in viscosity by more than 1,000 centipoise (cP) after administration.

One embodiment relates to a composition for use in local co-administration into a human or animal body according to the present invention, wherein the composition is a liquid before administration into the human or animal body that increases in viscosity by more than 10,000 centipoise (cP) after administration.

In another embodiment the present invention relates to a composition for use in local co-administration into a human or animal body wherein the composition comprises an active pharmaceutical ingredient.

In another embodiment the present invention relates to a composition for use in local co-administration into a human or animal body wherein the composition comprises an active pharmaceutical ingredient, wherein the active pharmaceutical ingredient is an anti-cancer chemotherapeutics selected from the class of compounds that are anti-metabolites, anti-microtubule agents, topoisomerase inhibitors, cytotoxic antibiotics, alkylating agents, radiosensitizers, or are photosensitizers.

In another embodiment the present invention relates to a composition for use in local co-administration into a human or animal body wherein the composition is an x-ray contrast agent for imaging.

In another embodiment the present invention relates to a composition for use in local co-administration into a human or animal body, wherein the composition is an X-ray contrast agent which is an organic substance.

In another embodiment the present invention relates to a composition for use in local co-administration into a human or animal body wherein the composition is an X-ray contrast agent, which comprises one or more iodinated polymers, iodinated oligomers, iodinated lipids, iodinated saccharides, iodinated disaccharides, iodinated polysaccharides, iodinated peptides, or a derivative or a combination thereof.

In another embodiment the present invention relates to a composition for use in local co-administration into a human or animal body wherein the composition comprise an active pharmaceutical ingredient, wherein the active pharmaceutical ingredient is one or more compounds selected from the group of anti-cancer and radiosensitizer drugs, such as irinotecan hydrochloride, nogitecan hydrochloride, exatecan, lurtotecan, docetaxel hydrate, cyclophosphamide, lifosfamide, nimustine, carboquone, chlorambucil, dacarbazine, enocitabine, gemcitabine, carmofur, cytarabine, cytarabine ocphosphate, tegafur, doxifluridine, hydroxycarbamide, 5-fluorouracil, methotrexate, mercaptopurine, fludarabine phosphate, actinomycin D, aclarubicin hydrochloride, idarubicin hydrochloride, epirubicin hydrochloride, daunorubicin hydrochloride, pirarubicin hydrochloride, bleomycin hydrochloride, zinostatin stimalamer, neocarzinostatin, mytomycin C, bleomycin sulfate, peplomycin sulfate, vinorelbine tartrate, vincristine sulfate, vindesine sulfate, vinblastine sulfate, amrubicin hydrochloride, gefitinib, exemestan, capecitabine, doxorubicin, mitomycin, paclitaxel, nitrogen mustards, etoposide, camptothecin, nicotinamide, metronidazole, oxaliplatin, cisplatin, carboplatin, camptothecin, Tirapazamine, Vinblastine, Vinorelbine, Vincristine, Daunorubicin Tamoxifen, Imatinib, Dasatinib, nilotinib, Gefrtinib, ertoinib, Sorafenib, Sunitinib, Lapatinib, Bortezomib, interferon-alfa, lnterteukin-2, Thalidomide, Lenaiidomide, Temsiroiimus, Everolimus, and the like, but not limited to those. Active pharmaceuticals may be formulated in various forms and the present invention is to be seen as incorporating various forms of formulations of the active ingredient. In another embodiment the present invention relates to a composition for use in local co-administration into a human or animal body wherein the composition is a liquid before administration and has the ability to transform into a gel-like material after administration. In another embodiment the present invention relates to a composition for use in local co-administration into a human or animal body wherein the composition becomes a solid after injection such as a crystalline or amorphous solid. In another embodiment the present invention relates to a composition for use in local co-administration into a human or animal body wherein an increase in viscosity after administration into the human or animal body is due to diffusion of a molecule out of the gel-like material and into surrounding tissue. In another embodiment the present invention relates to a composition for use in local co-administration into a human or animal body wherein an increase in viscosity after administration into the human or animal body is due to diffusion of solvent-like molecules.

In another embodiment the present invention relates to a composition for use in local co-administration into a human or animal body wherein at least 50% of the non-water soluble carbohydrates are pyranose based carbohydrates selected from derivatives of lactose, maltose, trehalose, raffinose, glucosamine, galactosamine and lactoseamine, or mixtures thereof. In another embodiment the present invention relates to a composition for use in local co-administration into a human or animal body wherein at least 50% of the non-water soluble carbohydrates are disaccharides with at least two pyranose saccharide units, or mixtures thereof. In another embodiment the present invention relates to a composition for use in local co-administration into a human or animal body, wherein the non-water soluble carbohydrates are disaccharides with structures selected from:

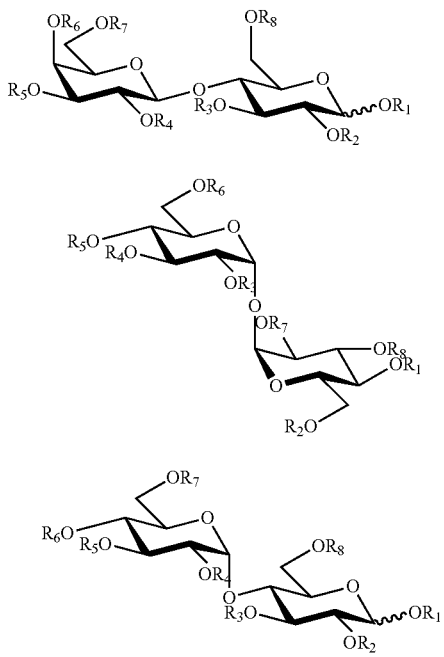

wherein $R_1$, $R_2$, $R_3$, $R_4$, $R_5$, $R_6$, $R_7$, and $R_8$ in formulae I, II or III are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, and $R_8$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

or wherein all groups of $R_1$, $R_2$, $R_3$, $R_4$, $R_5$, $R_6$, $R_7$, and $R_8$ are selected collectively from the group consisting of acetyl, isobutyryl or propionyl; or wherein $R_1$, $R_2$, $R_3$, $R_4$, $R_5$, $R_6$, $R_7$, and $R_8$ are independently selected from the group consisting acetyl, isobutyryl or propionyl;

and wherein both pure anomers and mixtures of α- and β-anomers of the preceding mentioned structural variations are claimed.

In another embodiment the present invention relates to a composition for use in local co-administration into a human or animal body wherein at least 50% of the non-water soluble carbohydrates are trisaccharides or a mixture of trisaccharides. In another embodiment the present invention relates to a composition for use in local co-administration into a human or animal body wherein the non-water soluble carbohydrates are trisaccharides with structures selected from:

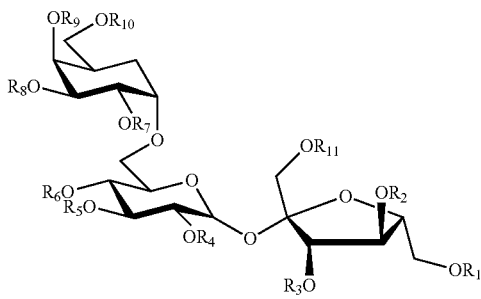

wherein $R_1$, $R_2$, $R_3$, $R_4$, $R_5$, $R_6$, $R_7$, $R_8$, $R_9$, $R_{10}$ and $R_{11}$ in formulae IV are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, $R_8$, $R_9$, $R_{10}$ and $R_{11}$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

or wherein all groups of $R_1$, $R_2$, $R_3$, $R_4$, $R_5$, $R_6$, $R_7$, $R_8$, $R_9$, $R_{10}$ and $R_{11}$ are selected collectively from the group consisting of acetyl, isobutyryl or propionyl; or wherein $R_1$, $R_2$, $R_3$, $R_4$, $R_5$, $R_6$, $R_7$, $R_8$, $R_9$, $R_{10}$ and $R_{11}$ are independently selected from the group consisting acetyl, isobutyryl or propionyl;

and wherein both pure anomers and mixtures of α- and β-anomers of the preceding mentioned structural variations are claimed.

In another embodiment the present invention relates to a composition for use in local co-administration into a human or animal body wherein at least 50% of the non-water soluble carbohydrates are oligosaccharides or a mixture of oligosaccharides with at least 4 monosaccharide units linked together In another embodiment the present invention relates to a composition for use in local co-administration into a human or animal body wherein at least 50% of the non-water soluble carbohydrates are mono- or oligosaccharides containing at least one amino sugar unit. In another embodiment the present invention relates to a composition for use in local co-administration into a human or animal body wherein the at least one amino sugar is selected from compounds with the structure:

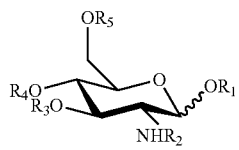

wherein $R_1$, $R_2$, $R_3$, $R_4$ and $R_5$ in formulae V are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$ and $R_5$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl, mono- di-, tri- or tetra-saccharide derivatives;

or wherein all groups of $R_1$, $R_2$, $R_3$, $R_4$ and $R_5$ are selected collectively from the group consisting of acetyl, isobutyryl or propionyl; or wherein $R_1$, $R_2$, $R_3$, $R_4$ and $R_5$ are independently selected from the group consisting acetyl, isobutyryl or propionyl;

and wherein both pure anomers and mixtures of α- and β-anomers of the preceding mentioned structural variations are claimed.

In another embodiment the present invention relates to a composition for use in local co-administration into a human or animal body wherein release of said one or more active pharmaceutical ingredients is controlled by mixing carbohydrates with different hydrophobicity by alteration of the substitutions on the carbohydrate hydroxyl groups. In another embodiment the present invention relates to a composition for use in local co-administration into a human or animal body wherein the active pharmaceutical ingredient is formulated in a nanoparticle or microsphere that is dispersed in the composition to control the release rate of the active pharmaceutical ingredient. In another embodiment the present invention relates to a composition for use in local co-administration into a human or animal body wherein the X-ray contrast agent is an inorganic acid or salt. In another embodiment the present invention relates to a composition for use in local co-administration into a human or animal body wherein the composition also comprises particles in the size range from 1-1000 nm, such as nanoparticles in the size range from 2 to 500 nm. In another embodiment the present invention relates to a composition for use in local co-administration into a human or animal body wherein the nanoparticles comprises gold (Au). In another embodiment the present invention relates to a composition for use in local co-administration into a human or animal body wherein the composition also comprises, radioactive compounds, paramagnetic compounds, fluorescent compounds or ferromagnetic compounds, or any mixture thereof. In another embodiment the present invention relates to a composition for use in local co-administration into a human or animal body wherein the composition contains an MRI, SPECT or PET contrast agent.

In one embodiment the present invention relates to a composition for use in local co-administration into a human or animal body wherein the composition also comprises a molecule that increase gel stability in the human or animal body, selected from the group interfacially active molecule, amphiphilic molecule, and/or emulsifier. In another embodiment the present invention relates to a composition for use in local co-administration into a human or animal body wherein the composition also comprises a molecule that increase gel stability in the human or animal body wherein said molecule that increase gel stability is selected from the group poly(ethylene glycol-b-caprolactone) (PEG-PCL), poly(D,L-lactic acid) (PLA), or poly(lactic-co-glycolic acid) (PGLA), or any combination thereof.

In one embodiment the present invention relates to a composition for use in local co-administration into a human or animal body wherein the composition comprises iodinated derivate of carbohydrate or iodinated derivative of poly-alcohols, such as iodinated derivatives of sucrose acetate isobutyrate (SAIB), such as iodinated derivatives of lactose, such as iodinated derivatives of trehalose, such as iodinated derivatives of arabinose, such as iodinated derivatives of maltose, such as iodinated derivatives of glucose, such as iodinated derivatives of galactose, iodinated derivatives of glucosamine, such as iodinated glucosamine, and the like.

In another embodiment the present invention relates to a composition for use in local co-administration into a human or animal body wherein the composition comprises an iodinated derivate of a carbohydrate doped into a composition of the same class of non-idoninated carbohydrate derivatives. In another embodiment the present invention relates to a composition for use in local co-administration into a human or animal body in combination with radiotherapy. In another embodiment the present invention relates to a composition for use in local co-administration into a human or animal body for use as a tissue marker.

Another aspect of the present invention relates to a method of recording an X-ray image of the body of a mammal, comprising the steps of a. providing an X-ray contrast composition comprising an organic X-ray agent in a non-water soluble carbohydrate gel-forming system;

b. administering the X-ray contrast composition to a predetermined location of the mammal, and c. recording X-ray-based images of at least a part of the body which comprises the predetermined location.

Yet another aspect of the present invention relates to a method of joint radiotherapy and X-ray imaging of a target tissue in a mammal, comprising the steps of a. providing an X-ray contrast composition comprising an organic X-ray agent in a non-water soluble carbohydrate gel-forming system;

b. administering the X-ray contrast composition to a predetermined target tissue of the mammal, c. recording X-ray-based images, of at least a part of the body which comprises the target tissue, thereby providing a definition of the target tissue, and d. using the definition of the target tissue obtained in c) to direct external beam radiotherapy to the target tissue.

Yet another aspect of the present invention relates to a method for directing local administration of a pharmaceutically active agent to a target tissue in a mammal, comprising the steps of a. providing an X-ray contrast composition comprising an organic X-ray agent in a non-water soluble carbohydrate gel-forming system;

b. administering the X-ray contrast composition to a predetermined target tissue of the mammal, c. recording X-ray-based images, of at least a part of the body which comprises the target tissue, thereby providing a definition of the target tissue, and d. using the X-ray contrast composition in b) to further comprise an active pharmaceutical agent for delivery of an active pharmaceutical agent to a predetermined target tissue of the mammal.

In another embodiment the present invention relates to a method for a composition for use in local co-administration into a human or animal body wherein at least 50% of the non-water soluble carbohydrates are pyranose based carbohydrates selected from derivatives of lactose, maltose, trehalose, raffinose, glucosamine, galactosamine and lactoseamine, or mixtures thereof. In another embodiment the present invention relates to a method for a composition for use in local co-administration into a human or animal body wherein the non-water soluble carbohydrates are disaccharides with at least two pyranose saccharide units. In another embodiment the present invention relates to a method for a composition for use in local co-administration into a human or animal body wherein the non-water soluble carbohydrates are disaccharides with structures selected from:

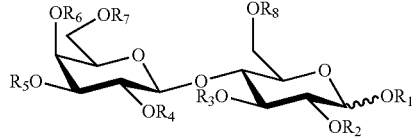

Formulae I

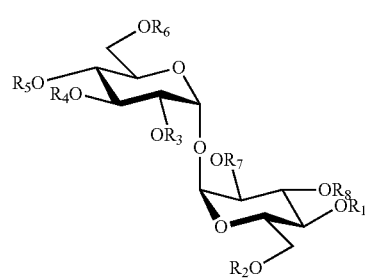

II

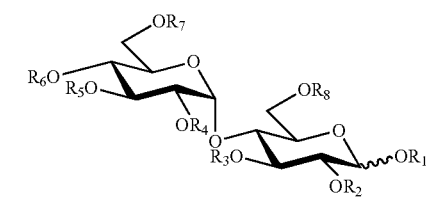

III wherein $R_1$, $R_2$, $R_3$, $R_4$, $R_5$, $R_6$, $R_7$, and $R_8$ in formulae I, II or III are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, and $R_8$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

or wherein all groups of $R_1$, $R_2$, $R_3$, $R_4$, $R_5$, $R_6$, $R_7$, and $R_8$ are selected collectively from the group consisting of acetyl, isobutyryl or propionyl; or wherein $R_1$, $R_2$, $R_3$, $R_4$, $R_5$, $R_6$, $R_7$, and $R_8$ are independently selected from the group consisting acetyl, isobutyryl or propionyl;

and wherein both pure anomers and mixtures of α- and β-anomers of the preceding mentioned structural variations are claimed.

In another embodiment the present invention relates to a method for a composition for use in local co-administration into a human or animal body wherein the non water soluble carbohydrates are trisaccharides or a mixture of trisaccharides. In another embodiment the present invention relates to a method for a composition for use in local co-administration into a human or animal body wherein the non-water soluble carbohydrates are trisaccharides with structures selected from:

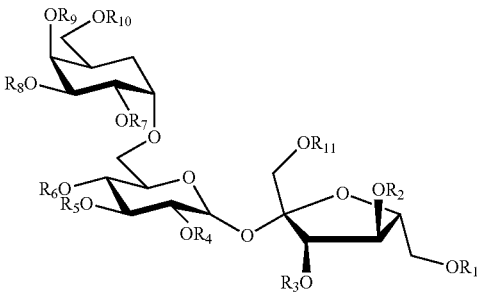

Formulae IV wherein $R_1$, $R_2$, $R_3$, $R_4$, $R_5$, $R_6$, $R_7$, $R_8$, $R_9$, $R_{10}$ and $R_{11}$ in formulae IV are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, $R_8$, $R_9$, $R_{10}$ and $R_{11}$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

or wherein all groups of $R_1$, $R_2$, $R_3$, $R_4$, $R_5$, $R_6$, $R_7$, $R_8$, $R_9$, $R_{10}$ and $R_{11}$ are selected collectively from the group consisting of acetyl, isobutyryl or propionyl; or wherein $R_1$, $R_2$, $R_3$, $R_4$, $R_5$, $R_6$, $R_7$, $R_8$, $R_9$, $R_{10}$ and $R_{11}$ are independently selected from the group consisting acetyl, isobutyryl or propionyl;

and wherein both pure anomers and mixtures of α- and β-anomers of the preceding mentioned structural variations are claimed. In another embodiment the present invention relates to a method for a composition for use in local co-administration into a human or animal body wherein the non water soluble carbohydrates are oligosaccharides with at least 4 monosaccharide units linked together. In another embodiment the present invention relates to a method for a composition for use in local co-administration into a human or animal body wherein the non water soluble carbohydrates are mono- or oligosaccharides containing at least one amino sugar unit.

In another embodiment the present invention relates to a method for a composition for use in local co-administration into a human or animal body wherein the amino sugars are selected from compounds with the structure:

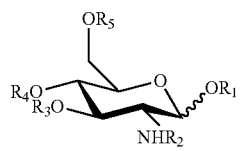

Formulae V wherein $R_1$, $R_2$, $R_3$, $R_4$ and $R_5$ in formulae V are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$ and $R_5$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl, carbohydrates and carbohydrate derivatives;

or wherein all groups of $R_1$, $R_2$, $R_3$, $R_4$ and $R_5$ are selected collectively from the group consisting of acetyl, isobutyryl or propionyl; or wherein $R_1$, $R_2$, $R_3$, $R_4$ and $R_5$ are independently selected from the group consisting acetyl, isobutyryl or propionyl;

and wherein both pure anomers and mixtures of α- and β-anomers of the preceding mentioned structural variations are claimed.

In another embodiment the present invention relates to a method for a composition for use in local co-administration into a human or animal body wherein the target tissue comprises undesirably growing cells.

In another embodiment the present invention relates to a method for a composition for use in local co-administration into a human or animal body wherein the target tissue comprises tumor cells. In another embodiment the present invention relates to a method for a composition for use in local co-administration into a human or animal body wherein steps (c) and (d) are performed simultaneously.

In another aspect, the present invention relates to a method for a composition for use in local co-administration into a human or animal body, which is administered to the human or animal body through a syringe, an endoscope or a bronchoscope to the target tissue preferably wherein the composition after insertion into the human or animal body constitutes a medical or surgical implant for tissue or surgical adhesion.

In yet another aspect, the present invention relates to a medical or surgical implant for use in local co-administration into a human or animal body wherein, wherein the composition is part of a sprayable composition.

In yet another aspect, the present invention relates a method for local administration of a composition for use in local co-administration, wherein an active pharmaceutical ingredient is released specifically into tissue in need thereof, preferably tumor tissue. In one embodiment, the present invention relates to a method for a composition for use in local co-administration with or without an active pharmaceutical ingredient into a human or animal body wherein the tissue is comprising an interorgan space such as an intraperitoneal space, a muscle, a dermis, an epidermis, a natural lumen or void, an abdominal cavity, a prostate, a rectum, a location between two or more organs such as a prostate and a rectum, a heart and lung, a lymph node and another tissue, a breast, a tissue between a radiation target and healthy tissue, and a vasculature.

In one embodiment the present invention relates to a composition for use in controlled release of at least one active pharmaceutical ingredient that modulates an immunogenic response in a human or animal body, said composition comprising non-water soluble carbohydrates and wherein the composition is a liquid before administration into the human or animal body and increases in viscosity by more than 1,000 centipoise (cP) after administration. In one embodiment the present invention relates to a composition for use in controlled release of at least one active pharmaceutical ingredient, wherein the composition is a liquid before administration into the human or animal body that increases in viscosity by more than 10,000 centipoise (cP) after administration into the human or animal body. In one embodiment the present invention relates to a composition for use in controlled release of at least one active pharmaceutical ingredient, wherein the composition is a liquid before administration and becomes a gel-like material or solid material, such as an crystalline solid or an amorphous solid, after administration. In one embodiment the present invention relates to a composition for use in controlled release of at least one active pharmaceutical ingredient, wherein an increase in viscosity after administration into the human or animal body is due to diffusion of a molecule out of the administered material and into surrounding tissue. In one embodiment the present invention relates to a composition for use in controlled release of at least one active pharmaceutical ingredient, wherein an increase in viscosity after administration into the human or animal body is due to diffusion of solvent-like molecules. In one embodiment the present invention relates to a composition for use in controlled release of at least one active pharmaceutical ingredient In one embodiment the present invention relates to a composition for use in controlled release of at least one active pharmaceutical ingredient, wherein at least 50% of the non-water soluble carbohydrates are selected from derivatives of glucose, galactose, mannose, lactose, maltose, trehalose, raffinose, glucosamine, galactosamine, and lactoseamine. In one embodiment the present invention relates to a composition for use in controlled release of at least one active pharmaceutical ingredient In one embodiment the present invention relates to a composition for use in controlled release of at least one active pharmaceutical ingredient, wherein said at least one active pharmaceutical ingredient is an immune-modulating compound which is a ligand for intracellular proteins and/or receptors; or a ligand for cell surface proteins and/or receptors. In one embodiment the present invention relates to a composition for use in controlled release of at least one active pharmaceutical ingredient, wherein said intracellular proteins and/or receptors are selected from the group consisting of NOD-like receptor (NLR) family and the subfamilies NLRA, NLRB, NLRC, NLRP, NODs, NALP, IPAF, HLA complexes, RIG-I-like receptors, cytokine receptors, interleukin receptors, CD proteins, CTLA proteins, PD1, T Cell receptor, B cell receptor, and theToll-like-receptor (TLR) family; TLR1, TLR2 TLR3, TLR4, TLR5, TLR6, TLR7, TLR8, TLR9, TLR10, TLR11, TLR12, TLR13. In one embodiment the present invention relates to a composition for use in controlled release of at least one active pharmaceutical ingredient, wherein the active pharmaceutical ingredient elicit immunogenicity that is a humoral and/or cell-mediated immune response. In one embodiment the present invention relates to a composition for use in controlled release of at least one active pharmaceutical ingredient, wherein said at least one active pharmaceutical ingredient is an immuno stimulating compound selected from the group consisting of polyinosinic:polycytidylic acid (poly I:C), Polyadenylic-polyuridylic acid (poly A:U), poly I:C-poly-L-lysine (poly-ICLC), poly-ICR, CL264, N-palmitoyl-S-[2,3-bis(palmitoyloxy)-(2R,S)-propyl]-(R)-cysteine-(S)serine-(S)lysine 4 ($Pam_3Cys$), Monophosphoryl lipid A (MPLA) and other lipopolysaccharides, alpha-galactosylceramide, Propirimine, Imiquimod (R837), resiquimod (R848), TMX-101, TMX-201, TMX-202, Gardiquimod, R850 (3M Pharma), R851 (3M Pharma), 852A (3M Pharma), S-27610, 3M-002 (CL075), 3M-003, 3M-005, 3M-006, 3M-007, 3M-012, 3M-13, 3M-031, 3M-854 (3M Pharma), CL097, CL264, IC-31, Loxoribine and other imidazoquinolines, ssPolyU, sotirimod (3M Pharma), Isatoribine (Anadys), ANA975 (Anadys/Novartis), SM360320 (Sumitomo), R1354 (Coley Pharmaceuticals) single stranded or double stranded RNA, ORN 02 (5'-UUAUUAUUAUUAUUAUUAUU-3'), ORN 06 5'-UUGUUGUUGUUGUUGUUGUU-3', CpG-ODN DSLIM (Mologen), AVE 0675 (Coley Pharmaceuticals), CpG B oligodeoxynucleotide (ODN) 1018 (Dynavax Technologies), AZD 1419 (Dynavax), ODN 1982, CpG B ODN 2006 (Coley Pharmaceuticals), IMO 2125 (Idera Pharma), CpG A ODN 2216, CpG A ODN 2336, CpG 2395, CpG ODN 7909 (Coley Pharmaceuticals), CpG 10101 (Coley Pharmaceuticals), CpG ODN AVE0675 (Coley Pharmaceuticals), CpG ODN HYB2093 (Idera Pharmaceuticals/Novartis), CpG ODN HYB2055 (Idera Pharmaceuticals), CpG-ODN IMO-2125 (Idera Pharmaceuticals), CpG C ODN M362, Tolamba (Amb a1 ragweed allergen with covalently linked CpG B class ODN 1018)(Dynavax Technologies), Heplisav (Dynavax Technologies), 10181SS (Dynavax Technologies), IM02055 (Idera Pharmaceuticals), IRS954 (Dynavax Technologies), (flagellin, muramyl dipeptide, saponins such as QS21, Leishmania elongation factor, SB-AS4, threonyl-muramyl dipeptide, L18-MDP, mifamurtid, and OM-174. In one embodiment the present invention relates to a composition for use in controlled release of at least one active pharmaceutical ingredient In one embodiment the present invention relates to a composition for use in controlled release of at least one active pharmaceutical ingredient, wherein said at least one active pharmaceutical ingredient is an immuno suppressive compound comprising a steroid selected from the group consisting of 21-Acetoxy-prefnenolone, Aalclometasone, Algestone, Amicinonide, Beclomethasone, Betamethasone, Betamethasone dipropionate, Betamethasone hemisuccinate, Budesonide, Chloroprednisone, Clobetasol, Blovetasone, Clocortolone, Cloprednol, Corticosterone, Cortisone, Cortivazol, Deflazacort, Desonide, Desoximethasone, dexamethason, Dexamethasone palmitate, Dexamethasone phosphate, Diflorasone, Diflucortolone, Difluprednate, Enoxolone, Fluazacort, Flucloronide, Flumethasone, Flunisolide, Fluocinolone Acetonide, Fludrocortisone, Fluocinonide, Fluocortin Butyl, Fluocortolone, Fluorometholone, Fluperolone, Fluprednidine, Fluprednisolone, Flurandrenolide, Formocortal, Halcinonide, Glucocorticoids, Halomethasone, Halopredone, Hydrocortamate, Hydrocortisone, Limethasone, Mazipredone, Medrysone, Meprednisone, Methyolprednisolone, Methyolprednisolone hemisuccinate, Mometasone Furoate, Paramethasone, Prednicarbate, Prednisolone, Prednisolone palmitate, Prednisolone phosphate, Prednisone, Prednival, Prednylidene, Tixocortal, and Triamcinolone. In one embodiment the present invention relates to a composition for use in controlled release of at least one active pharmaceutical ingredient, wherein said at least one active pharmaceutical ingredient is an immune-suppressive compound comprising a small molecule inhibitor acting on cellular targets selected from the group consisting of c-Fms, PDGFR⌑, Abl, PDGFR⌑, NFkB, IkB, JAK1, JAK2, JAK3, GSK3, p38 MAPK, JNK, KIT, EGFR, ERBB2, ERBB4, VEGFR1, VEGFR2, VEGFR3, FLT3, PKC☐, RAF1, CDK1, CDK2, CDK4, NLRP3, IRF3, STAT1, STAT2, STAT3, STAT4, STAT5, STAT6, JAK, Hsp90, Hsp70, PI3K, mTOR, AKT, DNA-PK, ATM, AMPK, PDK-1, S6 kinase, RIP2, TRIF, MYD88, TAK1, PTK2 (FAK), TAK1, Ras, Raf, Mek, Erk, GLUT1, GLUT2, HK1, HK2, Ca9, HIF-1, HIF-2, HIF-3, PHD1, PHD2, PHD3, ALK.

In one embodiment the present invention relates to a composition for use in controlled release of at least one active pharmaceutical ingredient, wherein said at least one active pharmaceutical ingredient is an immuno suppressive compound comprising a small molecule inhibitor acting on intracellular targets selected from the group consisting of indomethacin, CLI-095 (C15H17ClFNO4S, CAS #243984-11-4), Bay11-7082 (C10H9NO2S, CAS #19542-67-7), Triptolide (PG 490), CGP53716, SU9518, PD166326, Celastrol, Tripterin, BIRB-796 (Doramapimod), SB 203580, SB202190, VX-702, NVP-BEZ235, GDC-0980 (RG7422), Ridaforolimus (Deforolimus, AP23573), Nilotinib (Tasigna, AMN107), Sorafenib tosylate (Nexavar), Dasatinib (Sprycel, BMS-354825), MLN518 (CT53518), Vatalanib (PTK787/ZK222584), OSI-930, AZD2171, Pazopanib (Votrient), IPI-504 (retaspimycin), Deforolimus (Ridaforolimus), GDC-0980 (RG7422, $C_{23}H_{30}N_8O_3S$, CAS #1032754-93-0), Palomid 529 ($C_{24}H_{22}O_6$ CAS #914913-88-5), Imatinib mesylate (Gleevec/Glivec), Everolimus (Afinitor, RAD001), Sirolimus (Rapamune, rapamycin), Temsirolimus (Torisel, CCI-779), Bortezomib (Velcade), Gefitinib (Iressa), Canertinib (CI-1033, CAS #267243-28-7, $C_{24}H_{25}ClFN_5O_3$), Erlotinib hydrochloride (Tarceva), Pelitinib (EKB-569) ($C_{24}H_{23}ClFN_5O_2$, CAS #257933-82-7), Vandetanib (Zactima, ZD6474, $C_{22}H_{24}BrFN_4O_2$, CAS No.: 443913-73-3), Sunitinib (Sutent, SU-11248, $C_{22}H_{27}FN_4O_2 \cdot C_4H_6O_5$, CAS No.: 341031-54-7), Tandutinib (MLN518), $C_{31}H_{42}N_6O_4$, CAS No.: 387867-13-2, Roscovitine (Seliciclib), $C_{19}H_{26}N_6O$, CAS No.: 186692-46-6. In one embodiment the present invention relates to a composition for use in controlled release of at least one active pharmaceutical ingredient, wherein said at least one active pharmaceutical ingredient is an anti-infectious compound selected from the group consisting of Rifampicin, dideoxycytidine-5"-triphosphate, Clarithromycin, acyclovir, ciprofloxacin, fusidin, gentamicin, chloramphenicol, levofloxacin, oxytetracyclin, tobramycin, natriumcromoglicat, Amoxicillin, Ampicillin., Pivampicillin, Ertapenem, Meropenem, Doripenem, Cefotaxim, Ceftazidim, Ciprofloxacin, Valaciclovir, efavirenz, emtricitabin, tenofovirdisoproxil, Rilpivirine, penicillin, Trimethoprim-sulfamethoxazole, rifampicin, etambutol, isoniazid, pyrazinamide, voriconazole, amphotericin B, caspofungin, flucytosine, itraconazole, doxycyclin, sulfonamides, and sulfamethoxazole. In one embodiment the present invention relates to a composition for use in controlled release of at least one active pharmaceutical ingredient, wherein said at least one active pharmaceutical ingredient is an immunomodulating compound selected from the group consisting of thalidomide, lenalidomide and pomalidomide, sargramostim, IL-2, interferon-alfa, alemtuzumab, bevacizumab, brentuximab vedotin, cetuximab, gemtuzumab, ozogamicin, ibritumomab, tiuxetan, ipilimumab, ofatumumab, panitumumab, rituximab, tositumomab, trastuzumab, loxoribine, bropirimine, pomalidomide, sargramostim. In one embodiment the present invention relates to a composition for use in controlled release of at least one active pharmaceutical ingredient, further comprising at least one antigen. In one embodiment the present invention relates to a composition for use in controlled release of at least one active pharmaceutical ingredient, wherein at least 50% of the non-water soluble carbohydrates are disaccharides with at least two pyranose saccharide units, or mixtures thereof. In one embodiment the present invention relates to a composition for use in controlled release of at least one active pharmaceutical ingredient, wherein the non-water soluble carbohydrates are disaccharides with structures selected from:

Formulae I

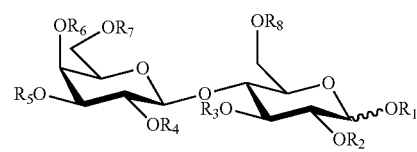

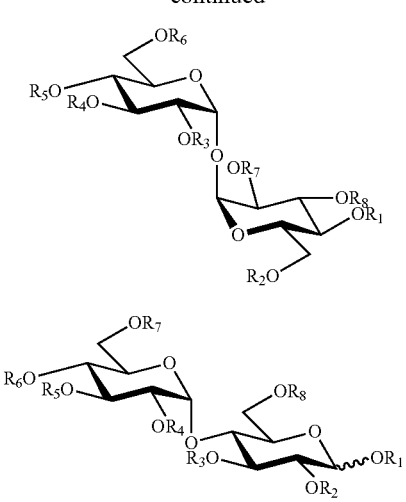

II

III wherein $R_1$, $R_2$, $R_3$, $R_4$, $R_5$, $R_6$, $R_7$, and $R_8$ in formulae I, II and III are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, and $R_8$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

or wherein all groups of $R_1$, $R_2$, $R_3$, $R_4$, $R_5$, $R_6$, $R_7$, and $R_8$ are selected collectively from the group consisting of acetyl, isobutyryl or propionyl; or wherein $R_1$, $R_2$, $R_3$, $R_4$, $R_5$, $R_6$, $R_7$, and $R_8$ are independently selected from the group consisting acetyl, isobutyryl or propionyl;

and wherein both pure anomers and mixtures of α- and β-anomers of the above mentioned structural variations are claimed.

In one embodiment the present invention relates to a composition for use in controlled release of at least one active pharmaceutical ingredient, wherein at least 50% of the non-water soluble carbohydrates are trisaccharides, or mixtures thereof. In one embodiment the present invention relates to a composition for use in controlled release of at least one active pharmaceutical ingredient, wherein the non-water soluble carbohydrates are trisaccharides with structures selected from:

Formulae IV

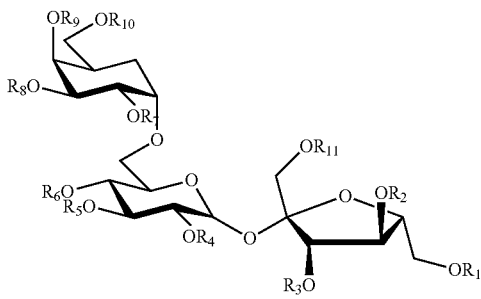

wherein $R_1$, $R_2$, $R_3$, $R_4$, $R_5$, $R_6$, $R_7$, $R_8$, $R_9$, $R_{10}$ and $R_{11}$ in formulae IV are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein $R_1$, $R_2$, $R_3$, $R_4$, $R_5$, $R_6$, $R_7$, $R_8$, $R_9$, $R_{10}$ and $R_{11}$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;

wherein all groups of $R_1$, $R_2$, $R_3$, $R_4$, $R_5$, $R_6$, $R_7$, $R_8$, $R_9$, $R_{10}$ and $R_{11}$ are selected collectively from the group consisting of acetyl, isobutyryl or propionyl; or wherein $R_1$, $R_2$, $R_3$, $R_4$, $R_5$, $R_6$, $R_7$, $R_8$, $R_9$, $R_{10}$ and $R_{11}$ are independently selected from the group consisting acetyl, isobutyryl or propionyl;

and wherein both pure anomers and mixtures of α- and β-anomers of the above mentioned structural variations are claimed.

In one embodiment the present invention relates to a composition for use in controlled release of at least one active pharmaceutical ingredient, wherein at least 50% of the non-water soluble carbohydrates are oligosaccharides or a mixture of oligosaccharides with at least 4 monosaccharide units linked together. In one embodiment the present invention relates to a composition for use in controlled release of at least one active pharmaceutical ingredient, wherein at least 50% of the non-water soluble carbohydrates are mono- or oligosaccharides containing at least one amino sugar unit. In one embodiment the present invention relates to a composition for use in controlled release of at least one active pharmaceutical ingredient, wherein the non-water soluble carbohydrates are amino sugars selected from compounds with the structure:

Formulae V

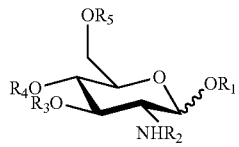

wherein $R_1$, $R_2$, $R_3$, $R_4$ and $R_5$ in formulae V are selected collectively from the group consisting of hydrogen, alkanoyl, hydroxyl-substituted alkanoyl, and acyloxy-substituted alkanyl, hydroxysubstituted alkanyl and acyloxy substituted alkanyl; or wherein $R_1$, $R_2$, $R_3$, $R_4$ and $R_5$ are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl, mono- di-, tri- or tetra-saccharide derivatives;

wherein all groups of $R_1$, $R_2$, $R_3$, $R_4$ and $R_5$ are selected collectively from the group consisting of acetyl, isobutyryl or propionyl; or wherein $R_1$, $R_2$, $R_3$, $R_4$ and $R_5$ are independently selected from the group consisting acetyl, isobutyryl or propionyl;

and wherein both pure anomers and mixtures of anomers such as α- and β-anomer centres of the above mentioned structural variations are claimed.

In one embodiment the present invention relates to a composition for use in controlled release of at least one active pharmaceutical ingredient, wherein the release of one or more active pharmaceutical ingredients is controlled by mixing carbohydrates with different hydrophobicity by alteration of the substitutions on the carbohydrate hydroxyl groups. In one embodiment the present invention relates to a composition for use in controlled release of at least one active pharmaceutical ingredient, wherein the composition also comprises a molecule that increase gel stability in the human or animal body, such as an interfacially active molecule, such as an amphiphilic molecule, such as an emulsifier. In one embodiment the present invention relates to a composition for use in controlled release of at least one active pharmaceutical ingredient, wherein the composition comprises contrast agents that makes the composition visible by PET imaging, SPECT imaging, Ultrasound imaging, CT imaging, x-ray imaging, fluoroscopy imaging, fluorescence imaging, or OCT imaging. In one embodiment the present invention relates to a composition for use in controlled release of at least one active pharmaceutical ingredient, wherein the active pharmaceutical ingredient is formulated in a nanoparticle or microsphere that is dispersed in the composition. In one embodiment the present invention relates to a composition for use in controlled release of at least one active pharmaceutical ingredient, in combination with radiotherapy, photodynamic therapy (PDT), hyperthermia based treatments such as high-intensity focused ultrasound (HIFU), radiofrequency thermal ablation (RFA), laser-therapy, or laser-induced interstitial thermotherapy (LITT). In one embodiment the present invention relates to a composition for use in controlled release of at least one active pharmaceutical ingredient, which is administered to the human or animal body through a syringe, an endoscope or a bronchoscope to the target tissue preferably wherein the composition after insertion into the human or animal body constitutes a medical or surgical implant for tissue or surgical adhesion which preferably is wound dressing, a hemostat, enhances tissue regeneration, or is a void filler. In one embodiment the present invention relates to a composition for use in controlled release of at least one active pharmaceutical ingredient, wherein the composition comprises organic radioisotopes or inorganic radionuclides for use as internal radiotherapy such as brachytherapy or in imaging of tissue in humans or animals.

Another aspect of the present invention relates to a medical or surgical implant comprising the composition according to any of the preceding claims, wherein the composition is part of a sprayable composition.

Another aspect of the present invention relates to use of a composition according to the present invention, for injecting into tumor tissue. In one embodiment the present invention relates to use of a composition for use in controlled release of at least one active pharmaceutical ingredient, in combination with external beam radiotherapy.

Yet another aspect of the present invention relates to a method for local administration of composition for use in controlled release of at least one active pharmaceutical ingredient, wherein the active pharmaceutical ingredient is released specifically into tissue in need thereof, preferably tumor tissue.

In one embodiment the present invention relates to a composition for use in controlled release of at least one active pharmaceutical ingredient in tissue, said tissue comprising an intraperitoneal space, a muscle, a dermis, an epidermis, a natural lumen or void, an abdominal cavity, a prostate, a rectum, a location between a prostate and a rectum, a breast, a tissue between a radiation target and healthy tissue, and a vasculature.

In one embodiment, the present invention relates to a method for a composition for use in local co-administration with or without an active pharmaceutical ingredient into a human or animal body wherein the tissue is comprising an interorgan space such as an intraperitoneal space, a muscle, a dermis, an epidermis, a natural lumen or void, an abdominal cavity, a prostate, a rectum, a location between two or more organs such as a prostate and a rectum, a heart and lung, a lymph node and another tissue, a breast, a tissue between a radiation target and healthy tissue, and a vasculature.

Example I

Synthesis

General experimental conditions: All reactions were carried out under inert atmosphere ($N_2$). Water sensitive liquids and solutions were transferred via syringe. Water used for washing of the syntheses was in all cases pure MiliQ water. Organic solutions were concentrated by rotary evaporation at 30-60° C. under 200-0 millibar. Thin layer chromatography (TLC) was carried out using aluminium sheets pre-coated with silica 60F (Merck 5554). The TLC plates were inspected under UV light or developed using a cerium ammonium sulphate solution (1% cerium(IV)sulphate and 2.5% hexa-ammonium molybdate in a 10% sulfuric acid solution).

Reagents: Chemicals were all purchased from Sigma Aldrich and were used as received. Dry pyridine was obtained by drying over sieves (4 Å) for 2-3 days prior to use.

Instrumentation: Nuclear Magnetic Resonance (NMR) was conducted on a Bruker Ascend™ 400 MHz—operating at 401.3 MHz for $^1$H and 100.62 MHz for $^{13}$C— with a 5 mm H-Broadband Dual Channel z-gradient Prodigy cryo-probe. All NMR spectra were acquired at 298 K. The FID files were processed in Mnova Suite version 8.1.4. All NMR spectra were recorded in CDCl$_3$, the signal at 7.26 ppm (singlet) and 77.16 ppm (triplet) were used for referencing in $^1$H-NMR and $^{13}$C-NMR spectra, respectively. In $^1$H-NMR spectra of α,β anomeric mixtures, the integral of H-1 of the most abundant anomer was always set to 1.0, and the percentage of each anomeric species was calculated from the integral ratio of H-1 α and H-1 β. MALDI-TOF MS was conducted on a Bruker Autoflex Speed™ instrument. The matrix used for MALDI-TOF was a mixture of 2,5 dihydroxy benzoic acid (DHB), trifluoroacetic acid and Na$^+$ in ethanol.

D-Glucosamine Esters:

α-D Glucosamine Pentaacetate:

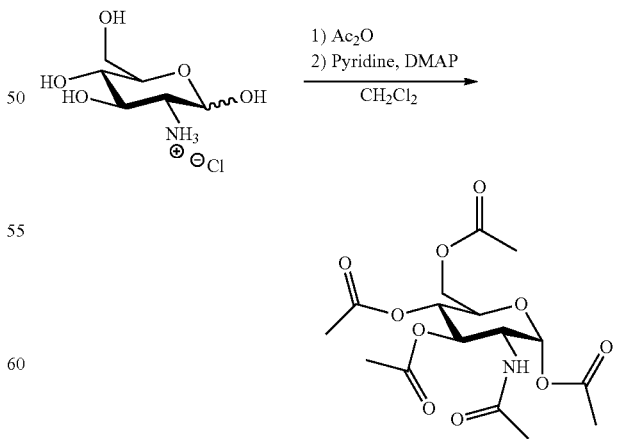

D-Glucosamine HCl (2 g, 9.3 mmol) was suspended in 10 mL dry $CH_2Cl_2$ under inert atmosphere ($N_2$) and cooled to 0° C. Hereafter, acetic anhydride (10 mL, 106 mmol, ~2.3 eq pr. OH) was carefully added followed by addition of dry pyridine (10 mL) and a catalytic amount of DMAP (117 mg, 0.96 mmol, ~0.1 eq). The reaction slowly returned to r.t. and was continued at this temperature for 30 h, whereafter the temperature was elevated to 40° C. and continued for another 32 h. Then TLC (acetone: toluene 1:1, Rf product ~0.6) showed that the reaction was completed. The reaction mixture was concentrated in vacuuo and co-evaporated with toluene. The concentrate was re-dissolved in CHCl$_3$ (100 mL) and washed with NaHCO$_3$ (aq) (4×100 mL) and water (2×100 mL). The pure α-anomer was isolated by re-crystallization from isopropanol-hexane. Yield: 2.2 g (61%). $^1$H NMR (400 MHz, CDCl$_3$) δ 6.15 (d, J=3.6 Hz, 1H), 5.63 (d, J=9.0 Hz, 1H), 5.26-5.15 (m, 2H), 4.52-4.41 (m, 1H), 4.23 (dd, J=12.5, 4.1 Hz, 1H), 4.04 (dd, J=12.5, 2.4 Hz, 1H), 3.98 (ddd, J=9.8, 4.1, 2.4 Hz, 1H), 2.17 (s, 3H), 2.07 (s, 3H), 2.03 (s, 3H), 2.02 (s, 3H), 1.92 (s, 3H).$^{13}$C NMR (101 MHz, CDCl$_3$) δ 171.8, 170.8, 170.1, 169.2, 168.7, 90.8, 70.8, 69.8, 67.6, 61.6, 51.1, 51.04, 23.1, 21.0, 20.8 (2C), 20.7. MALDI TOF-MS: Calc [M+Na]$^+$: 412.35. Found: 412.33.

α-D Glucosamine Pentapropionate:

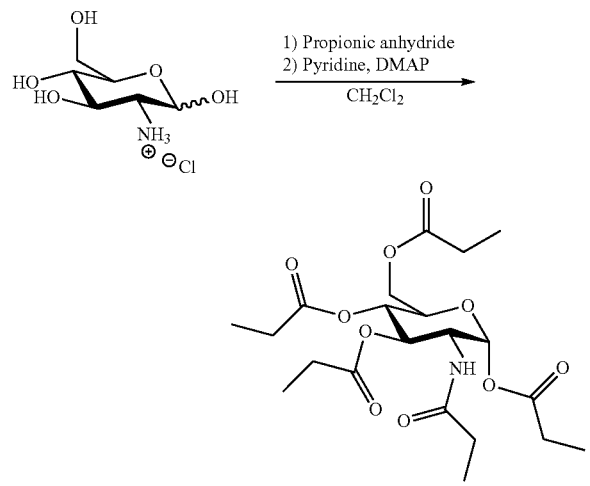

D-Glucosamine HCl (2 g, 9.3 mmol) was suspended in 10 mL dry CH$_2$Cl$_2$ under inert atmosphere (N$_2$) and cooled to 0° C. Hereafter, propionic anhydride (13 mL, 101.4 mmol, ~2.2 eq pr. OH) was carefully added followed by dry pyridine (11.5 mL) and a catalytic amount of DMAP (113 mg, 0.93 mmol, ~0.1 eq). The reaction slowly returned to r.t. and remained at this temp. for 2 h, whereafter the reaction was heated to 40° C. and continued at this temperature for 56 h. Then TLC (acetone: toluene 1:2, Rf product ~0.5) showed that the reaction was completed. The reaction was then concentrated in vacuuo and co-evaporated with toluene. The concentrate was dissolved in CHCl$_3$ (100 mL) and washed with NaHCO$_3$ (aq) (3×100 mL) and water (2×100 mL). The organic phase was then dried with MgSO$_4$(s), filtered and concentrated under reduced pressure. The pure α-anomer was isolated by re-crystallization from isopropanol. Yield: 2.6 g (61%). $^1$H NMR (400 MHz, CDCl$_3$) δ 6.18 (d, J=3.6 Hz, 1H, H-1 α), 5.50 (d, J=8.9 Hz, 1H), 5.30-5.17 (m, 2H), 4.52-4.44 (m, 1H), 4.23 (dd, J=12.5, 4.4 Hz, 1H), 4.06 (dd, J=12.5, 2.2 Hz, 1H), 3.98 (ddd, J=9.7, 4.4, 2.2 Hz, 1H), 2.44 (q, J=7.5 Hz, 2H), 2.40-2.21 (m, 6H), 2.12 (2xq, J=7.5 Hz, 2H), 1.24-1.02 (m, ~15H). $^{13}$C NMR (101 MHz, CDCl$_3$) δ 175.3, 174.2, 173.7, 172.7, 172.2, 90.7, 70.7, 70.0, 67.4, 61.6, 51.2, 51.08, 29.6, 27.7, 27.6, 27.5, 27.4, 9.7, 9.2 (2C), 9.1 (2C). MALDI TOF-MS: Calc [M+Na]$^+$: 482.49. Found: 482.50.

α,β-D Glucosamine Pentapropionate:

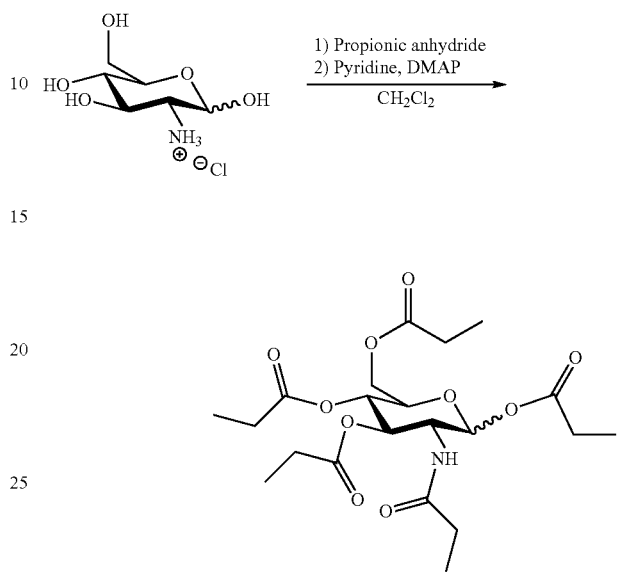

D-Glucosamine HCl (2 g, 9.3 mmol) was suspended in 10 mL dry CH$_2$Cl$_2$ under inert atmosphere (N$_2$) and cooled to 0° C. Hereafter, propionic anhydride (13 mL, 101.4 mmol, ~2.2 eq pr. OH) was carefully added followed by dry pyridine (11.5 mL) and a catalytic amount of DMAP (114.5 mg, 0.94 mmol, ~0.1 eq). The reaction slowly returned to r.t. and remained at this temp. for 1 h, whereafter the reaction was heated to 40° C. and continued at this temperature for 36 h. Then TLC (acetone: toluene 1:2, Rf products ~0.45) showed that the reaction was completed. The reaction was then concentrated in vacuuo and co-evaporated with toluene. The concentrate was dissolved in CHCl$_3$ (100 mL) and washed with NaHCO$_3$ (aq) (3×100 mL) and water (2×100 mL). The organic phase was then dried with MgSO$_4$(s), filtered and concentrated under reduced pressure, and an amorphous glass was obtained. Yield: 3.1 g (73%) (mixture of anomers: ~91% α and ~9% β). $^1$H NMR (400 MHz, Chloroform-d) δ 6.18 (d, J=3.6 Hz, 1H, H-1 α), 5.69 (d, J=8.8 Hz, 0.1H, H-1 β), 5.51 (d, J=9.0 Hz, 1H), 5.30-5.07 (m, 2H), 4.52-4.43 (m, 1H), 4.39-4.26 (m, 0.2H), 4.23 (dd, J=12.4, 4.4 Hz, 1H), 4.12 (dd, J=12.6, 2.3 Hz, 0.1H), 4.06 (dd, J=12.5, 2.2 Hz, 1H), 3.98 (ddd, J=9.6, 4.3, 2.2 Hz, 1H, H-5 α), 3.79 (ddd, J=9.4, 4.6, 2.1 Hz, 0.1H, H-5 β), 2.50-2.05 (m, ~11H), 1.23-1.01 (m, ~17H).MALDI TOF-MS: Calc [M+Na]$^+$: 482.49. Found: 482.50.

α-D Glucosamine Pentaisobutyrate:

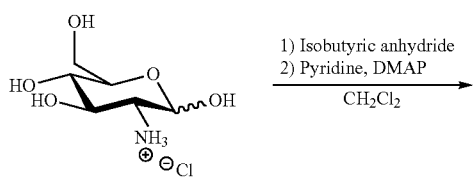

-continued

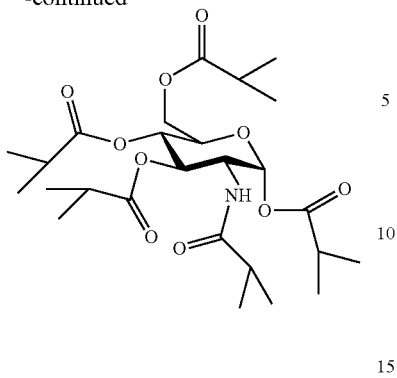

-continued

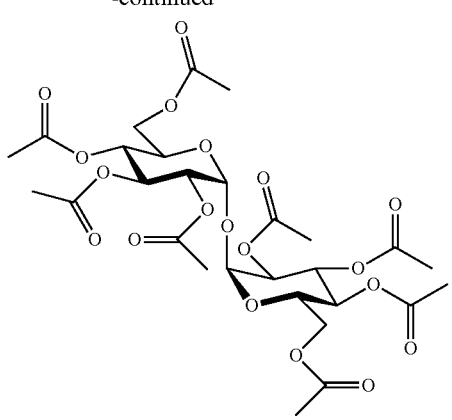

D-Glucosamine HCl (2 g, 9.3 mmol) was suspended in 10 mL dry CH$_2$Cl$_2$ under inert atmosphere (N$_2$) and cooled to 0° C. Hereafter, isobutyric anhydride (17 mL, 102.5 mmol, ~2.2 eq pr. OH) was carefully added followed by addition of dry pyridine (11.5 mL) and a catalytic amount of DMAP (113 mg, 0.93 mmol, ~0.1 eq). The reaction slowly returned to r.t. and remained at this temp. for 2 h, whereafter the reaction was heated to 40° C. and continued at this temperature for 58 h. Then TLC (acetone: toluene 1:2, Rf product ~0.6) showed that the reaction was completed. The reaction was concentrated in vacuuo and co-evaporated with toluene. Then, the concentrate was dissolved in CHCl$_3$ (100 mL) and washed with NaHCO$_3$ (aq) (3×100 mL) and water (2×100 mL). The organic phase was then dried with MgSO$_4$(s), filtered and concentrated under reduced pressure. The pure α-anomer was isolated by recrystallization from isopropanol. Yield: 2.95 g (60%). $^1$H NMR (400 MHz, CDCl$_3$) δ 6.19 (d, J=3.6 Hz, 1H), 5.52 (d, J=8.7 Hz, 1H), 5.34-5.13 (m, 2H), 4.55-4.35 (m, 1H), 4.15 (dd, J=12.4, 4.7 Hz, 1H), 4.09 (dd, J=12.4, 2.2 Hz, 1H), 3.99 (ddd, J=9.6, 4.7, 2.2 Hz, 1H), 2.72-2.44 (m, 4H), 2.25 (hept, J=7.2 Hz, 1H), 1.24 (d, J=1.5 Hz, 3H), 1.22 (d, J=1.5 Hz, 3H), 1.18-1.03 (m, ~24H). $^{13}$C NMR (101 MHz, CDCl$_3$) δ 178.1, 176.8, 176.6, 175.2, 174.7, 90.5, 70.4, 70.2, 67.0, 61.6, 51.5, 35.6, 34.2, 34.1, 34.0 (2C), 19.5, 19.4, 19.1 (2C), 19.0 (2C), 18.9 (4C). MALDI TOF-MS: Calc [M+Na]$^+$: 552.62. Found: 552.64.

Trehalose Esters:
Trehalose Octaacetate:

D-Trehalose dihydrate (2 g, 5.3 mmol) was suspended in 20 mL dry pyridine under inert atmosphere (N$_2$) followed by addition of acetic anhydride (9 mL, 95.4 mmol, ~2.3 eq pr. OH) and a catalytic amount of DMAP (70.9 mg, 0.6 mmol, ~0.1 eq). The reaction was conducted at r.t. overnight. After 15 h, the reaction temperature was re-adjusted to 48° C., and the reaction continued at this temperature for an additional 28 h after which TLC (20% acetone, toluene, rf product ~0.4) showed, that the reaction was done. Then followed concentration in-vacuuo and co-evaporation with toluene. The concentrate was re-dissolved in CHCl$_3$ (100 mL) and washed with NaHCO$_3$ (aq) (3×100 mL) and water (2×100 mL). The organic phase was dried with MgSO$_4$ (s), filtered, concentrated under reduced pressure and dried in vacuuo. Yield: 3.1 g (86%). $^1$H NMR (400 MHz, CDCl$_3$) δ 5.49 (dd, J=10.3, 9.3 Hz, 2H), 5.28 (d, J=3.9 Hz, 2H), 5.09-4.99 (m, 4H), 4.23 (dd, J=12.0, 5.5 Hz, 2H), 4.05 (ddd, J=10.3, 5.5, 2.0, 2H), 4.05-3.96 (m, 2H), 2.08 (s, 6H), 2.07 (s, 6H), 2.05 (s, 6H), 2.03 (s, 6H). $^{13}$C NMR (101 MHz, CDCl$_3$) δ 170.7 (2C), 170.1 (2C), 169.7 (4C), 92.4 (2C), 70.1 (2C), 70.0 (2C), 68.6 (2C), 68.3 (2C), 61.9 (2C), 20.8 (2C), 20.7 (6C).MALDI-TOF-MS: Calc. [M+Na]$^+$: 701.59. Found: 701.55.

Trehalose Octapropionate:

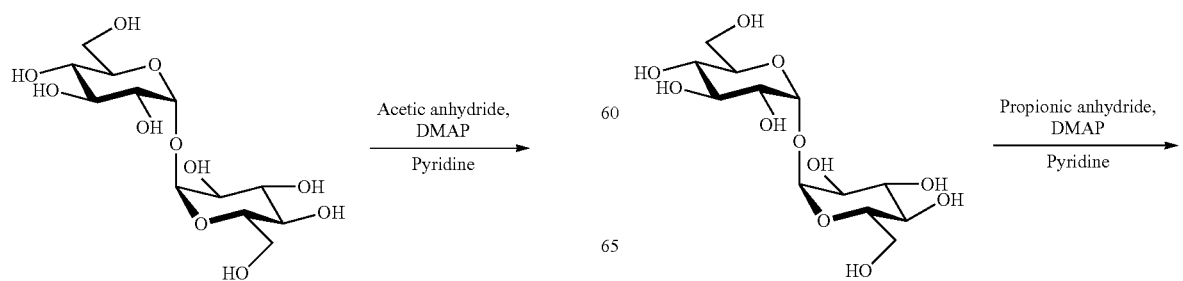

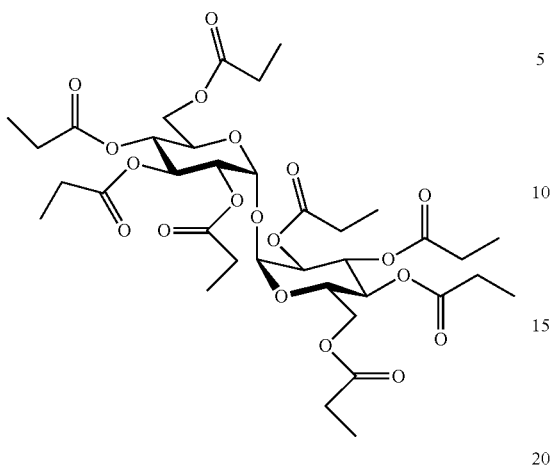

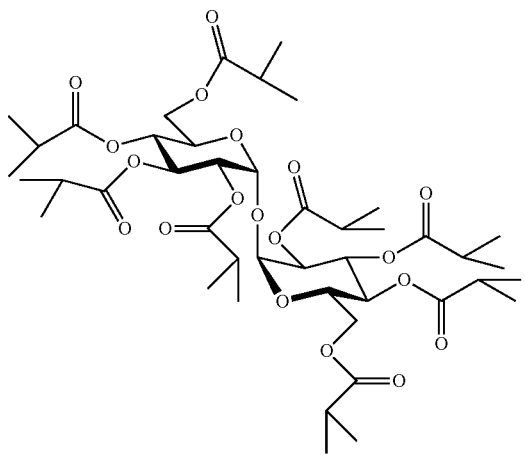

D-Trehalose dihydrate (2 g, 5.3 mmol) was suspended in 20 mL dry pyridine under inert atmosphere (N$_2$) followed by addition of propionic anhydride (12 mL, 93.6 mmol, ~2.2 eq pr. OH) and a catalytic amount of DMAP (73.1 mg, 0.6 mmol, ~0.1 eq). The reaction was conducted at 48° C. for 39 h, whereafter TLC (10% acetone, toluene, Rf product ~0.4) showed that the reaction was completed. Then followed concentration in vacuuo and co-evaporation with toluene. The crude concentrate was dissolved in CHCl$_3$ (100 mL) and and washed with NaHCO$_3$ (aq) (3×100 mL) and water (2×100 mL). The organic phase was dried with MgSO$_4$ (s), filtered, concentrated under reduced pressure and dried in vacuuo. Yield: 3.5 g (84.2%). $^1$H NMR (400 MHz, CDCl$_3$) δ 5.51 (dd, J=10.2, 9.3 Hz, 2H), 5.30 (d, J=3.8 Hz, 2H), 5.11-5.02 (m, 4H), 4.21 (dd, J=12.3, 5.6 Hz, 2H), 4.03-3.96 (m, 4H), 2.40-2.21 (m, 16H), 1.17-1.04 (m, 24H). $^{13}$C NMR (101 MHz, CDCl$_3$) δ 174.2 (2C), 173.4 (2C), 173.3 (2C), 173.1 (2C), 91.9 (2C), 70.0 (4C), 68.5 (2C), 68.3 (2C), 61.7 (2C), 27.6 (2C), 27.5 (6C), 9.3 (2C), 9.1 (6C). MALDI TOF-MS: Calc [M+Na]$^+$: 813.80. Found: 813.80.

Trehalose Octaisobutyrate:

D-Trehalose dihydrate (2 g, 5.3 mmol) was suspended in 20 mL dry pyridine under inert atmosphere (N$_2$) followed by addition of isobutyric anhydride (15.5 mL, 93.5 mmol, ~2.2 eq pr. OH) and a catalytic amount of DMAP (73.1 mg, 0.6 mmol, ~0.1 eq). The reaction was conducted at 49° C. for 47 h, whereafter TLC (10% acetone, toluene, Rf product ~0.6) showed that the reaction was only close to completion. Additional isobutyric anhydride (1.93 mL, 11.6 mmol) was added, and the reaction was continued for an additional 14 h at 58° C., whereafter the reaction was completed. Then followed concentration in vacuuo and co-evaporation of toluene. The crude concentrate was dissolved in CHCl$_3$ (100 mL) and washed with NaHCO$_3$ (aq) (3×100 mL) and water (2×100 mL). The organic phase was dried with MgSO$_4$ (s), filtered, concentrated under reduced pressure and dried in vacuuo. Yield: 4.3 g (91%). $^1$H NMR (400 MHz, CDCl$_3$) δ 5.55 (t, J=9.8 Hz, 2H), 5.36 (d, J=3.8 Hz, 2H), 5.10 (t, J=9.9 Hz, 2H), 5.03 (dd, J=10.1, 3.8 Hz, 2H), 4.08 (m, 4H), 3.91 (ddd, J=10.4, 5.5, 2.1 Hz, 2H), 2.63-2.52 (m, 4H), 2.48 (m, 4H), 1.17 (m, 24H), 1.13-1.07 (m, 24H). $^{13}$C NMR (101 MHz, CDCl$_3$) δ 176.7 (2C), 175.9 (2C), 175.7 (2C), 175.4 (2C), 90.5 (2C), 70.2 (2C), 69.8 (2C), 68.6 (2C), 68.0 (2C), 61.6 (2C), 34.1 (2C), 34.0 (4C), 33.9 (2C), 19.1 (2C), 19.0 (8C), 18.9 (4C), 18.8 (2C).MALDI TOF-MS: Calc [M+Na]$^+$: 926.02. Found: 925.97.

Maltose Esters:

β-Maltose Octaacetate:

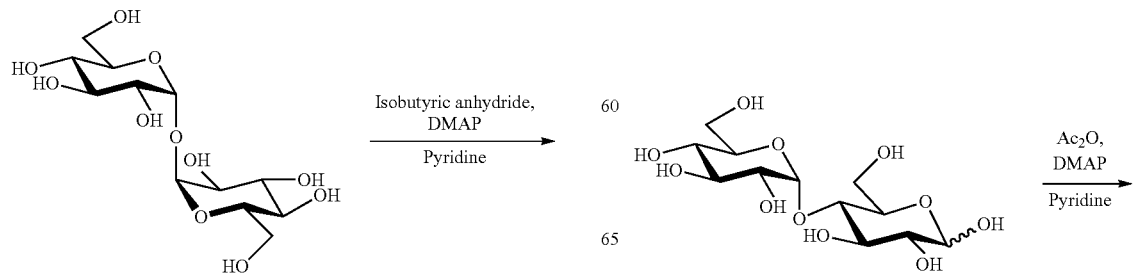

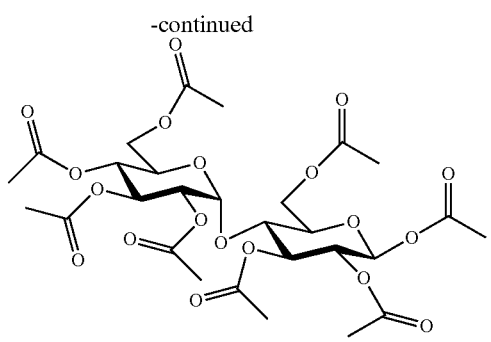

D-Maltose monohydrate (2 g, 5.6 mmol) was suspended in 20 mL dry pyridine under inert atmosphere ($N_2$) followed shortly hereafter by addition of acetic anhydride (9.5 mL, 100.5 mmol, ~2.3 eq pr. OH) and a catalytic amount of DMAP (73.1 mg, 0.6 mmol, ~0.1 eq). The reaction was conducted at 49° C. for 47 h whereafter TLC (20% acetone, toluene, Rf product ~0.4) showed that the reaction was completed. Then followed concentration in vacuuo and co-evaporation with toluene. The crude concentrate was dissolved in $CHCl_3$ (100 mL) and washed with $NaHCO_3$ (aq) (3×100 mL) and water (2×100 mL). The organic phase was then dried with $MgSO_4$ (s), filtered and concentrated under reduced pressure. The pure β-anomer was isolated by rechrystallization from isopropanol. Yield: 3.1 g (82%). $^1$H NMR (400 MHz, $CDCl_3$) δ 5.74 (d, J=8.1 Hz, 1H), 5.40 (d, J=4.0 Hz, 1H), 5.35 (dd, J=10.5, 9.5 Hz, 1H), 5.29 (t, J=8.9 Hz, 1H), 5.05 (t, J=9.9 Hz, 1H), 4.97 (dd, J=9.2, 8.1 Hz, 1H), 4.85 (dd, J=10.5, 4.0 Hz, 1H), 4.45 (dd, J=12.3, 2.5 Hz, 1H), 4.24 (t, J=3.9 Hz, 1H), 4.21 (t, J=3.8 Hz, 1H), 4.07-4.00 (m, 2H), 3.93 (ddd, J=10.3, 3.8, 2.3 Hz, 1H), 3.83 (ddd, J=9.6, 4.4, 2.5 Hz, 1H), 2.13 (s, 3H), 2.10 (s, 6H), 2.04 (s, 3H), 2.02 (s, 3H), 2.01 (2×s, 6H), 2.00 (s, 3H). $^{13}$C NMR (101 MHz, $CDCl_3$) δ 170.7, 170.6 (2C), 170.2, 170.0, 169.7, 169.6, 168.9, 95.8, 91.4, 75.4, 73.1, 72.5, 71.1, 70.1, 69.4, 68.7, 68.1, 62.6, 61.6, 21.00, 20.9, 20.8 (2C), 20.7 (4C). MALDI-TOF-MS: Calc [M+Na]$^+$: 701.59. Found: 701.38.

β-Maltose Octapropionate:

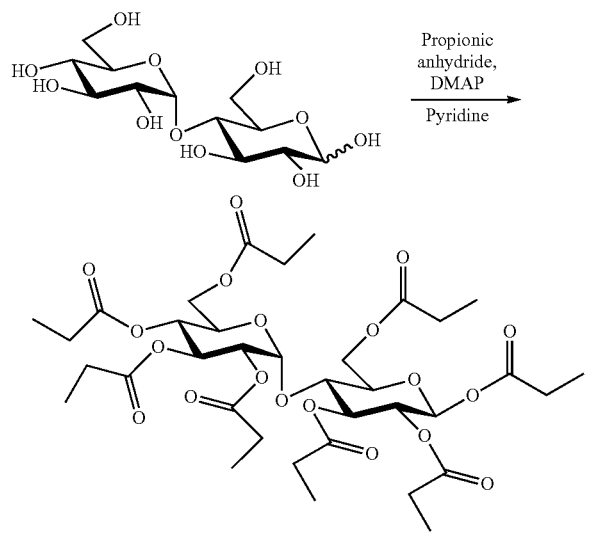

D-Maltose monohydrate (2 g, 5.6 mmol) was suspended in 20 mL dry pyridine under inert atmosphere ($N_2$) followed shortly hereafter by addition of propionic anhydride (12.5 mL, 97.5 mmol, ~2.2 eq pr. OH) and a catalytic amount of DMAP (68.9 mg, 0.56 mmol, ~0.1 eq). The reaction was conducted for 24 h at 48° C. and for an additional 16 h at 40° C., whereafter TLC (10% acetone, toluene, Rf product ~0.4) showed that the reaction was completed. Then followed concentration in vacuuo and co-evaporation with toluene. The concentrate was dissolved in $CHCl_3$ (100 mL) and washed with $NaHCO_3$ (aq) (3×100 mL) and water (2×100 mL). The organic phase was dried with $MgSO_4$ (s), filtered and concentrated under reduced pressure. The pure β-anomer was isolated by rechrystallization from isopropanol. Yield: 3.6 g (82%). $^1$H NMR (400 MHz, $CDCl_3$) δ 5.75 (d, J=8.2 Hz, 1H), 5.41-5.33 (m, 2H), 5.30 (t, J=9.0 Hz, 1H), 5.08 (t, J=9.9 Hz, 1H), 4.98 (dd, J=9.3, 8.2 Hz, 1H), 4.87 (dd, J=10.5, 4.0 Hz, 1H), 4.45 (dd, J=12.3, 2.6 Hz, 1H), 4.25 (t, J=4.5 Hz, 1H), 4.22 (t, J=4.6 Hz, 1H), 4.09-3.97 (m, 2H), 3.93 (ddd, J=10.3, 3.7, 2.1 Hz, 1H), 3.84 (ddd, J=9.7, 4.4, 2.6 Hz, 1H), 2.43-2.20 (m, 16H), 1.17-1.03 (m, 24H). $^{13}$C NMR (101 MHz, $CDCl_3$) δ 174.1, 174.0 (2C), 173.4 (2C), 173.1, 173.0, 172.4, 95.8, 91.4, 76.8, 75.3, 73.2, 72.2, 71.0, 69.9, 69.4, 68.8, 67.8, 62.5, 61.4, 27.6 (2C), 27.5 (3C), 27.4 (2C), 27.3, 9.3, 9.1 (4C), 8.9, 8.8 (2C). MALDI-TOF-MS: Calc [M+Na]$^+$: 813.80. Found: 813.70.

α,β-Maltose Octapropionate:

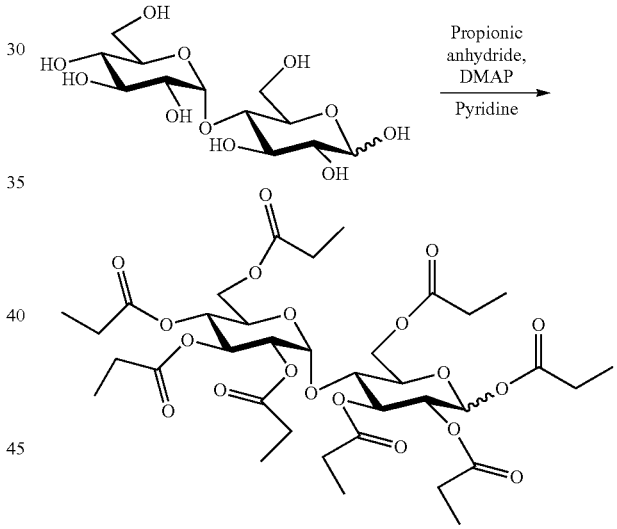

D-Maltose monohydrate (2 g, 5.6 mmol) was suspended in 20 mL dry pyridine under inert atmosphere ($N_2$) followed shortly hereafter by addition of propionic anhydride (12.5 mL, 97.5 mmol, ~2.2 eq pr. OH) and a catalytic amount of DMAP (70 mg, 0.57 mmol, ~0.1 eq). The reaction was conducted for 43 h at 48° C. and, whereafter TLC (10% acetone, toluene, Rf products ~0.35) showed that the reaction was completed. Then followed concentration in vacuuo and co-evaporation with toluene. The concentrate was dissolved in $CHCl_3$ (100 mL) and washed with $NaHCO_3$ (aq) (3×100 mL) and water (2:100 mL). The organic phase was dried with $MgSO_4$ (s), filtered and concentrated under reduced pressure to give a white solid. Yield: 3.3 g (76%) (mixture of anomers, ~4% alpha and ~96% beta). $^1$H NMR (400 MHz, Chloroform-d) δ 6.25 (d, J=3.7 Hz, 0.04H, H-1 α), 5.75 (d, J=8.2 Hz, 1H, H-1β), 5.53 (dd, J=10.1, 8.5 Hz, 0.04H), 5.40-5.33 (m, 2H), 5.30 (t, J=9.0 Hz, 1H), 5.08 (t, J=9.9 Hz, 1H), 4.98 (dd, J=9.3, 8.2 Hz, 1H), 4.87 (dd, J=10.5, 4.1 Hz, 1H), 4.45 (dd, J=12.2, 2.6 Hz, 1H), 4.25 (t, J=4.5 Hz, 1H), 4.22 (t, J=4.6 Hz, 1H), 4.12 (m, 0.04H), 4.09-3.98 (m, 2H), 3.93 (ddd, J=10.1, 3.7, 2.1 Hz, 1H), 3.84 (ddd, J=9.6, 4.4, 2.6 Hz, 1H), 2.47-2.18 (m, ~17H), 1.19-1.02 (m, ~25H). MALDI-TOF-MS: Calc [M+Na]$^+$: 813.80. Found: 813.70.

β-Maltose Octaisobutyrate:

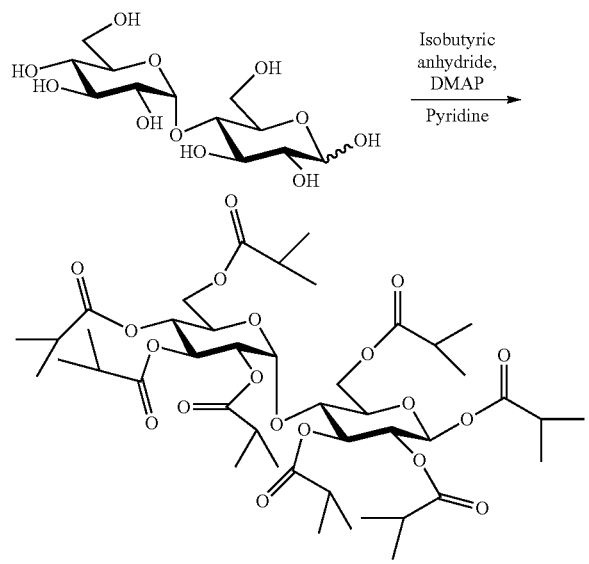

D-Maltose monohydrate (2 g, 5.6 mmol) was suspended in 20 mL dry pyridine under inert atmosphere (N$_2$) followed by addition of isobutyric anhydride (16.2 mL, 97.7 mmol, ~2.2 eq pr. OH) and a catalytic amount of DMAP (68 mg, 0.56 mmol, 0.1 eq). The reaction was conducted under inert atmosphere at 48° C. for 24 h, and for an additional 17 h at 40° C., whereafter TLC (10% acetone, toluene, Rf product ~0.5) showed that the reaction was completed. Then followed concentration in vacuuo and co-evaporation with toluene. The concentrate was dissolved in CHCl$_3$ (100 mL) and washed with NaHCO$_3$ (aq) (3×100 mL) and water (2×100 mL). The organic phase was then dried with MgSO$_4$ (s), filtered and concentrated under reduced pressure. The pure β-anomer was isolated by rechrystallization from isopropanol. Yield: 4.5 g (89%). $^1$H NMR (400 MHz, CDCl$_3$) δ 5.74 (d, J=8.0 Hz, 1H), 5.40 (t, J=9.9 Hz, 1H), 5.36-5.26 (m, 2H), 5.12 (t, J=9.8 Hz, 1H), 5.01 (dd, J=9.1, 8.0 Hz, 1H), 4.89 (dd, J=10.4, 4.0 Hz, 1H), 4.49 (dd, J=12.0, 2.7 Hz, 1H), 4.27 (dd, J=12.1, 4.7 Hz, 1H), 4.20 (dd, J=12.5, 4.0 Hz, 1H), 4.11-3.99 (m, 2H), 3.96 (ddd, J=10.4, 3.9, 2.0 Hz, 1H), 3.85 (ddd, J=9.6, 4.7, 2.7 Hz, 1H), 2.66-2.38 (m, 8H), 1.21-1.06 (m, 48H). $^{13}$C NMR (101 MHz, CDCl$_3$) δ 176.8, 176.6, 176.2, 175.8, 175.5, 175.4, 175.3, 175.0, 100.1, 95.2, 91.4, 75.0, 73.3, 71.6, 70.7, 69.9, 69.3, 68.9, 67.6, 62.3, 61.5, 34.1, 34.0 (3C), 33.9 (3C), 33.8, 19.3, 19.2, 19.1 (2C), 19.0 (4C), 18.9 (4C), 18.7, 18.5 (2C), 18.4. MALDI TOF-MS: Calc [M+Na]$^+$: 926.02. Found: 925.96.

Lactose Esters:
α,β-Lactose Octaacetate:

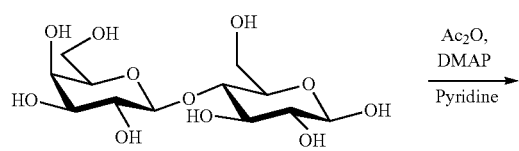

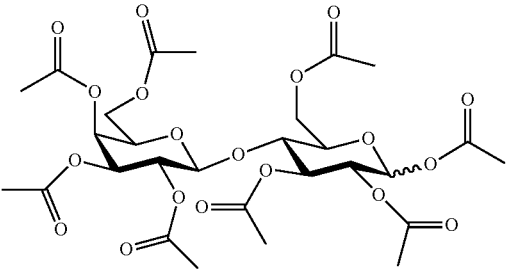

β-Lactose (10 g, 29.2 mmol) was suspended in dry pyridine (100 mL) under inert atmosphere (N$_2$). Hereafter, Ac$_2$O (48.5 mL, 514 mmol, ~2.2 eq pr. OH) was carefully added, followed by a catalytic amount of DMAP (357 mg, 2.9 mmol, 0.1 eq). The reaction was heated to 48° C. and continued for 24 h, then the reaction was cooled down to r.t. and continued for another 24 h, whereafter TLC (25% acetone, toluene, Rf α anomer: ~0.3, Rf β anomer: ~0.35) showed that the reaction was completed. The reaction was then concentrated in vacuuo and co-evaporated with toluene. The concentrate was dissolved in CHCl$_3$ (150 mL) and washed with NaHCO$_3$ (aq) (3×150 mL) and water (2×150 mL). The organic phase was dried with MgSO$_4$ (s), filtered, concentrated under reduced pressure and dried in vacuuo resulting in an amorphous glass. Yield: 18.6 g (93.7% yield) (mixture of anomers: ~30% α and ~70% β).$^1$H-NMR: (400 MHz, Chloroform-d) δ 6.24 (d, J=3.7 Hz, 0.4H, H-1 α), 5.66 (d, J=8.3 Hz, 1H, H-1 β), 5.44 (dd, 10.28, 9.53 Hz, 0.4H), 5.37-5.31 (m, 2H), 5.23 (t, J=9.1 Hz, 1H), 5.15-5.00 (m, 3H), 4.99-4.91 (m, 2H), 4.50-4.41 (m, 3H), 4.17-4.05 (m, 4H), 3.99 (ddd, J=10.2, 4.3, 2.1 Hz, 0.4H, H5 α), 3.91-3.78 (m, 3H), 3.75 (ddd, J=9.9, 4.8, 2.0 Hz, 1H, H5 β), 2.19-1.93 (singlets, ~32H, CH$_3$acetyls). MALDI TOF-MS: Calc [M+Na]$^+$: 701.59. Found: 701.51.

α,β-Lactose Octapropionate:

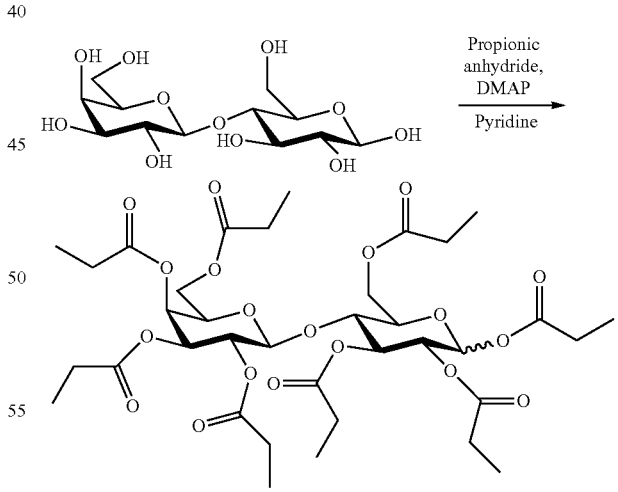

β-Lactose (5 g, 14.6 mmol) was suspended in dry pyridine (50 mL) under inert atmosphere (N$_2$). Hereafter, propionic anhydride (33.5 mL, 257.4 mmol, 2.2 eq pr. OH) was carefully added, followed by a catalytic amount of DMAP (181.3 mg, 1.48 mmol, 0.1 eq). The reaction was heated to 60° C. and continued for 32 h, whereafter TLC (10% acetone, toluene, Rf α anomer: ~0.35, Rf β anomer: ~0.4) showed that the reaction was completed. The reaction was then concentrated in vacuuo and co-evaporated with toluene. The concentrate was dissolved in $CH_2Cl_2$ (150 mL) and washed with 10% HCl (aq) (2×150 mL), then $NaHCO_3$ (aq) (2×100 mL) and water (2×200 mL). The organic phase was dried with $MgSO_4$ (s), filtered, concentrated under reduced pressure and dried in vacuuo resulting in an amorphous glass. Yield: 9.7 g (84%) (mixture of anomers: ~30% α and ~70% β). $^1$H-NMR (400 MHz, Chloroform-d) δ 6.26 (d, J=3.7 Hz, 0.4H, H1-α), 5.68 (d, J=8.3 Hz, 1H, H-1 β), 5.47 (dd, 10.3, 9.2 Hz, 0.4H), 5.38-5.33 (m, 2H), 5.26 (t, J=9.2 Hz, 1H), 5.15-5.00 (m, 3H), 5.02-4.91 (m, 2H), 4.49-4.41 (m, 3H), 4.15-4.03 (m, 4H), 3.98 (ddd, J=10.1, 3.9, 1.8 Hz, 0.4H, H5 α), 3.91-3.77 (m, 3H), 3.73 (ddd, J=9.9, 4.6, 2.0 Hz, 1H, H5 β), 2.47-2.15 (m, ~23H), 1.19-0.99 (m, ~34H). MALDI TOF-MS: Calc [M+Na]$^+$: 813.80. Found: 813.42.

α,β-Lactose Octaisobutyrate:

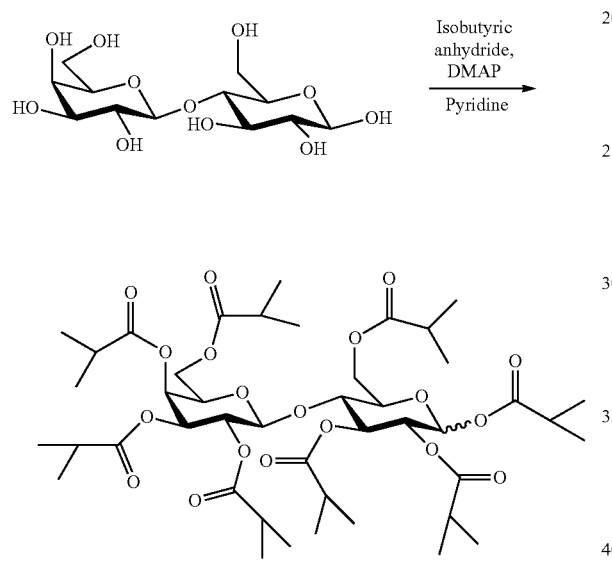

β-Lactose (10 g, 29.2 mmol) was suspended in dry pyridine (100 mL) under inert atmosphere ($N_2$). Hereafter, isobutyric anhydride (85 mL, 512.6 mmol, 2.2 eq. pr. OH) was carefully added, followed by a catalytic amount of DMAP (357 mg, 2.9 mmol, 0.1 eq). The reaction was heated to 55° C. and continued for 36 h, whereafter the reaction was cooled down to r.t. and continued for another 24 h, whereafter TLC (10% acetone, toluene, Rf α anomer: ~0.6, Rf β anomer: ~0.65) showed that the reaction was completed. The reaction was then concentrated in vacuuo and co-evaporated with toluene. The concentrate was dissolved in $CHCl_3$ (150 mL) and washed with $NaHCO_3$ (aq) (3×150 mL) and water (2×150 mL). The organic phase was dried with $MgSO_4$ (s), filtered, concentrated under reduced pressure and dried in vacuuo resulting in an amorphous glass. Yield: 23.6 g (89.5%) (mixture of anomers: ~30% α and ~70% β). $^1$H NMR (400 MHz, Chloroform-d) δ 6.26 (d, J=3.8 Hz, 0.4H, H-1β), 5.68 (d, J=8.3 Hz, 1H, H-1β), 5.48 (dd, J=10.3, 9.3 Hz, 0.4H), 5.40-5.34 (m, 2H), 5.27 (t, J=9.5 Hz, 1H), 5.18-5.00 (m, 3H), 5.03-4.91 (m, 2H), 4.50-4.41 (m, 3H), 4.24-4.02 (m, ~4H), 3.95 (ddd, J=10.1, 3.8, 1.7 Hz, 0.4H, H5 α), 3.91-3.80 (m, 3H), 3.70 (ddd, J=9.9, 4.5, 2.0 Hz, 1H, H5 β), 2.70-2.32 (m, ~11H), 1.26-1.01 (m, ~68H). MALDI TOF-MS: Calc [M+Na]$^+$: 926.02. Found: 925.70.

Raffinose Esters:

Raffionse Undecaacetate:

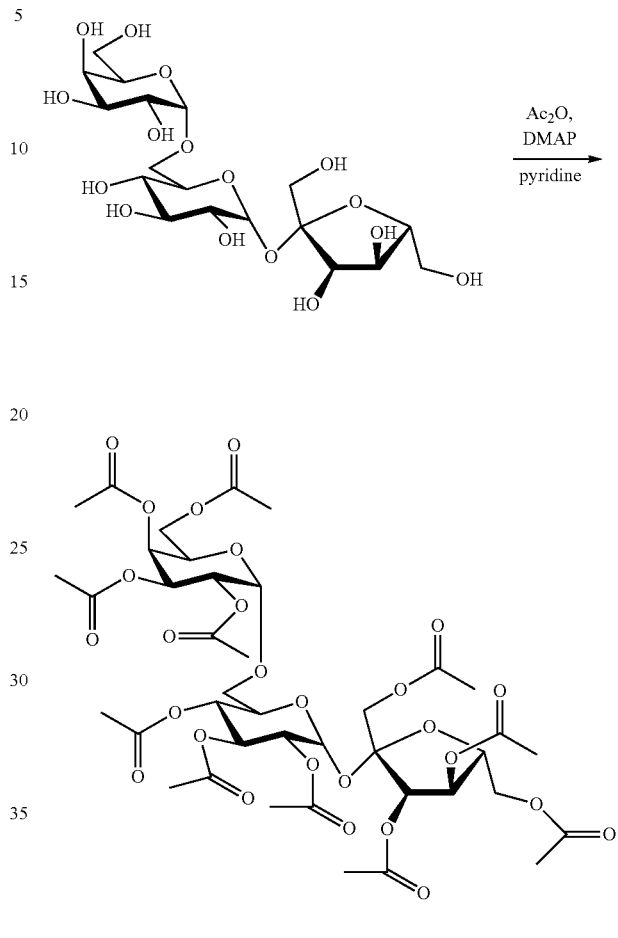

D-Raffinose pentahydrate (2 g, 3.4 mmol) was suspended in dry pyridine (20 mL) under inert atmosphere ($N_2$). Hereafter, acetic anhydride (6 mL, 63.5 mmol, ~1.7 eq pr. OH) was added followed by a catalytic amount of DMAP (41 mg, 0.3 mmol, ~0.1 eq). The reaction was heated to 48° C. and continued for 46 h where TLC (20% acetone, toluene, Rf product ~0.3) showed that the reaction was completed. The reaction was concentrated in vacuuo and co-evaporated with toluene. The concentrate was dissolved in $CHCl_3$ (100 mL) and washed with $NaHCO_3$ (aq) (3×100 mL) and water (2×100 mL). The organic phase was dried with $MgSO_4$ (s), filtered, concentrated under reduced pressure and dried in vacuuo. Yield: 2.9 g (88.7%). $^1$H NMR (400 MHz, $CDCl_3$) δ 5.65 (d, J=3.6 Hz, 1H), 5.50-5.43 (m, 3H), 5.36-5.31 (m, 1H), 5.30 (d, J=3.4 Hz, 1H), 5.13-5.08 (m, 2H), 5.07 (d, J=3.7 Hz, 1H), 5.00 (dd, J=10.4, 9.4 Hz, 1H), 4.76 (dd, J=10.4, 3.6 Hz, 1H), 4.41-4.22 (m, 6H), 4.22-4.10 (m, 2H), 4.03 (dd, J=11.3, 7.0 Hz, 1H), 3.72 (dd, J=11.1, 6.1 Hz, 1H), 3.52 (dd, J=11.0, 2.0 Hz, 1H), 2.17 (s, 3H), 2.14 (s, 3H), 2.12 (s, 3H), 2.11 (s, 3H), 2.11 (s, 3H), 2.10 (s, 6H), 2.05 (s, 6H), 2.01 (s, 3H), 1.95 (s, 3H). $^{13}$C NMR (101 MHz, $CDCl_3$) δ 170.7 (2C), 170.6, 170.4, 170.3 (2C), 170.2 (2C), 169.8, 169.7, 169.6, 105.0, 96.0, 90.2, 80.1, 76.5, 76.0, 70.7, 69.6, 69.4, 68.9, 68.4 (2C), 67.5, 66.5, 66.1, 63.8, 62.0 (2C), 20.9 (4C), 20.8 (5C), 20.7 (2C). MALDI TOF-MS: Calc [M+Na]$^+$: 989.84. Found: 989.91.

Raffinose Undecapropionate:

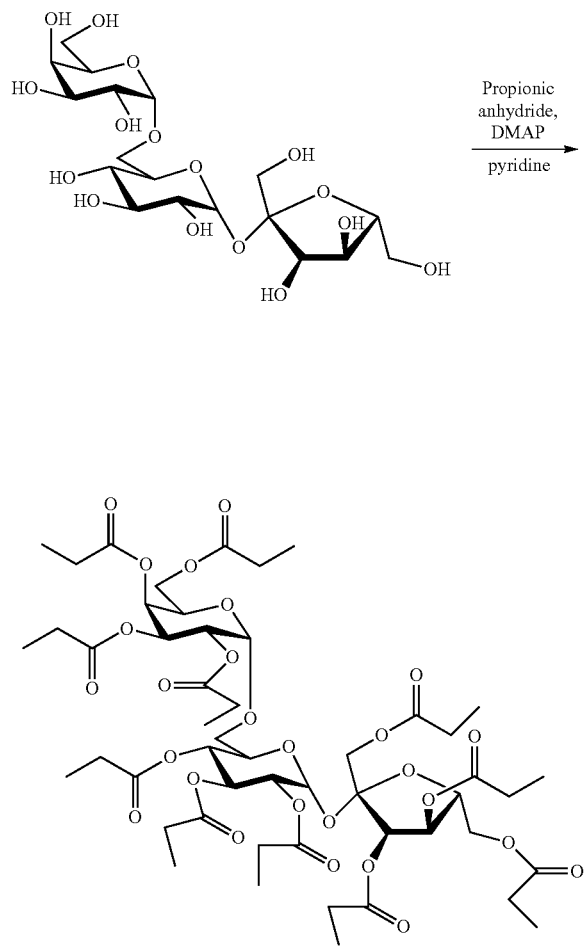

D-Raffinose pentahydrate (2 g, 3.4 mmol) was suspended in dry pyridine (20 mL) under inert atmosphere ($N_2$). Hereafter, propionic anhydride (8 mL, 62.4 mmol, ~1.7 eq pr. OH) was carefully added followed by a catalytic amount of DMAP (46 mg, 0.4 mmol, ~0.1 eq). The reaction was heated to 48° C. and continued for 42 h where TLC (10% acetone, toluene, Rf product ~0.4) showed that the reaction was completed. The reaction was concentrated in vacuuo and co-evaporated with toluene. The concentrate was dissolved in $CHCl_3$ (100 mL) and washed with $NaHCO_3$ (aq) (3×100 mL) and water (2×100 mL). The organic phase was dried with $MgSO_4$ (s), filtered, concentrated under reduced pressure and dried in vacuuo. Yield: 3.3 g (86.7%). $^1H$ NMR (400 MHz, $CDCl_3$) δ 5.61 (d, J=3.6 Hz, 1H), 5.52-5.41 (m, 3H), 5.39-5.30 (m, 2H), 5.15-5.04 (m, 3H), 4.82 (dd, J=10.4, 3.7 Hz, 1H), 4.43-4.22 (m, 6H), 4.21-4.01 (m, 3H), 3.73 (dd, J=11.3, 5.2 Hz, 1H), 3.54 (dd, J=11.3, 1.9 Hz, 1H), 2.50-2.17 (m, 22H), 1.18-1.03 (m, ~33H). $^{13}C$ NMR (101 MHz, $CDCl_3$) δ 174.2, 174.1, 174.0, 173.8, 173.6 (4C), 173.2, 173.1, 173.0, 104.6, 96.4, 90.3, 79.7, 76.0, 75.5, 70.3, 69.7 (2C), 68.5, 68.2 (2C), 67.7, 66.5, 66.0, 63.8, 62.4, 61.7, 27.6 (2C), 27.5 (5C), 27.4 (2C), 27.3, 27.2, 9.4, 9.3, 9.2 (2C), 9.1 (2C), 9.0 (5C). MALDI TOF-MS: Calc [M+Na]⁺: 1144.13. Found: 1144.18.

Raffinose Undecaisobutyrate:

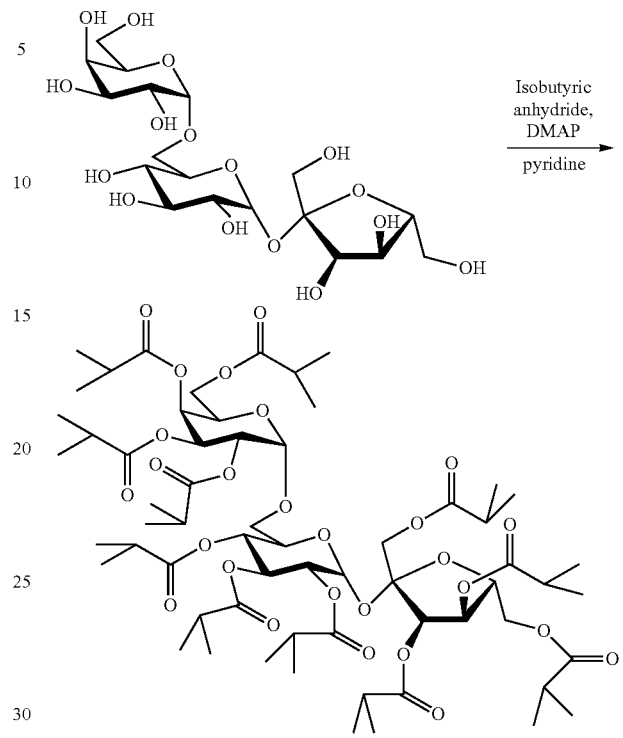

D-Raffinose pentahydrate (2 g, 3.4 mmol) was suspended in dry pyridine (20 mL) under inert atmosphere ($N_2$). Hereafter, isobutyric anhydride (10 mL, 60.3 mmol, ~1.6 eq pr. OH) was carefully added followed by a catalytic amount of DMAP (47 mg, 0.4 mmol, ~0.1 eq). The reaction was heated to 48° C. and continued for 43 h where TLC (10% acetone, toluene, Rf product ~0.6) showed that the reaction was completed. The reaction was then concentrated in vacuuo and co-evaporated with toluene. The concentrate was dissolved in $CHCl_3$ (100 mL) and washed with $NaHCO_3$ (aq) (3×100 mL) and water (2×100 mL). The organic phase was dried with $MgSO_4$ (s), filtered, concentrated under reduced pressure and dried in vacuuo. Yield: 3.6 g (84.3%). $^1H$ NMR (400 MHz, $CDCl_3$) δ 5.58-5.44 (m, 4H), 5.49-5.38 (m, 1H), 5.42-5.29 (m, 1H), 5.28 (t, J=9.8 Hz, 1H), 5.18-5.07 (m, 2H), 4.89 (dd, J=10.4, 3.6 Hz, 1H), 4.41-4.30 (m, 1H), 4.31-4.14 (m, 4H), 4.11-3.99 (m, 4H), 3.75 (dd, J=11.7, 3.4 Hz, 1H), 3.58 (dd, J=11.8, 1.9 Hz, 1H), 2.71-2.34 (m, 11H), 1.24-1.08 (m, ~66H). $^{13}C$ NMR (101 MHz, $CDCl_3$) δ 176.6 (2C), 176.5, 176.1 (3C), 176.0, 175.9, 175.8, 175.5, 175.1, 103.6, 97.0, 90.0, 78.7, 75.3, 74.6, 70.1, 69.8, 69.6, 68.1, 67.8 (2C), 67.7, 66.6, 65.9, 64.2, 62.9, 61.4, 34.2, 34.0 (5C), 33.9 (4C), 33.8, 19.3 (2C), 19.1 (3C), 19.0 (7C), 18.9 (6C), 18.8, 18.7, 18.5, 18.4. MALDI TOF-MS: Calc [M+Na]⁺: 1298.43. Found: 1298.46.

Synthesis of α,β Lactose Acetate:Propionate 1:1 Regioisomers

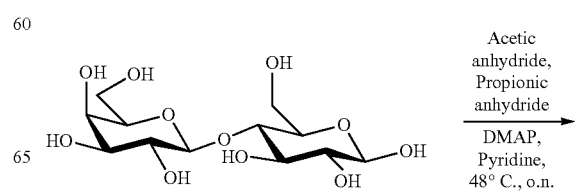

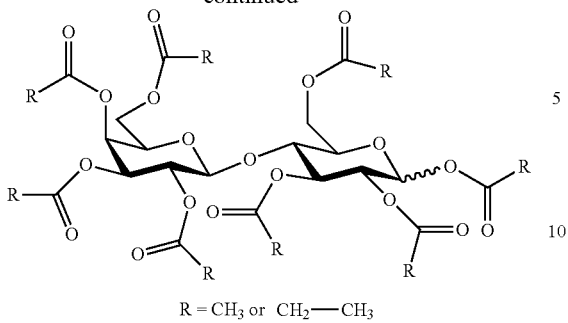

R = CH₃ or CH₂—CH₃

Lactose (10 g, 29.2 mmol) was suspended under inert atmosphere in ~120 mL dry pyridine and cooled to 0° C. Hereafter, a mixture of of acetic anhydride (16.5 mL, 175.3 mmol, ~6 eq.) and propionic anhydride (22.5 mL, 175.2 mmol, ~6 eq.) was added dropwise through a separatory funnel under vigorous stirring. Hereafter, the reaction was allowed to slowly re-heat to r.t. over ~30 min. Then, a catalytic amount of DMAP (~357 mg, 2.9 mmol, ~0.1 eq) was added, and the reaction was continued at 48° C. overnight under inert atmosphere. Then MALDI TOF-MS confirmed that the reaction was done. Hereafter followed evaporation of the solvent and anhydride with co-evaporation of toluene (2×20 mL) to remove the residual anhydride. The final purification consisted of dissolution in CHCl₃ (100 mL) and washing with NaHCO₃ (aq) (4×100 mL), water (1×100 mL) and brine (1×100 mL). The organic phase was then dried with MgSO₄ (s), filtered, concentrated under reduced pressure and dried in vacuo. Yield: 15.2 g (71%) (calculated after the expected weight of overall ~1:1 acetate:propionate mixture in the resulting product (confirmed by ¹H-NMR)), ~75% β and ~25% α (from ¹H-NMR). ¹H-NMR (400 MHz, Chloroform-d): δ 6.28-6.23 (m, 2H, H-1α), 5.71-5.63 (m, 6H, H-1β), 5.52-5.41 (m, 2H), 5.40-5.31 (m, 12H), 5.31-5.19 (m, 6H), 5.16-4.88 (m, ~15H), 4.52-4.40 (m, ~16H), 4.19-4.03 (m, ~28H), 4.03-3.94 (m, 2H), 3.91-3.79 (m, ~18H), 3.80-3.70 (m, 6H), 2.50-2.18 (m, ~48H, CH₂ propionate), 2.15-1.92 (m, ~72H, CH₃ acetate), 1.27-0.93 (m, ~72H, CH₃ propionate). MALDI TOF-MS: Compound with 7 acetyl and 1 propyl [M+Na]⁺: Calc.: 715.62. Found: 715.7. Compound with 6 acetyl+2 propyl [M+Na]⁺: Calc.: 729.65. Found: 729.81. Compound with 5 acetyl+3 propyl [M+Na]⁺: Calc.: 743.67. Found: 743.85. Compound with 4 acetyl+4 propyl [M+Na]⁺: Calc.: 757.70. Found: 757.88. Compound with 3 acetyl+5 propionyl [M+Na]⁺: Calc: 771.73. Found: 771.9. Compound with 6 propionyl+2 acetyl [M+Na]⁺. Calc. 785.76. Found: 785.93.

Regioisomer Trehalose Synthesis
Synthesis of Trehalose Acetate:Propionate 3:1 and 2:1 Regioisomers

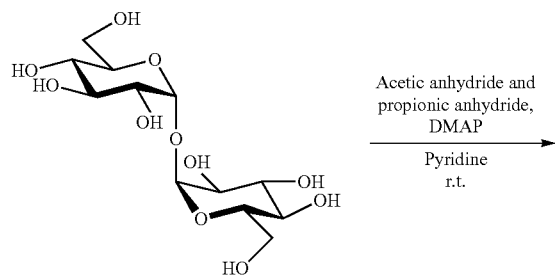

Acetic anhydride and propionic anhydride, DMAP
⟶
Pyridine
r.t.

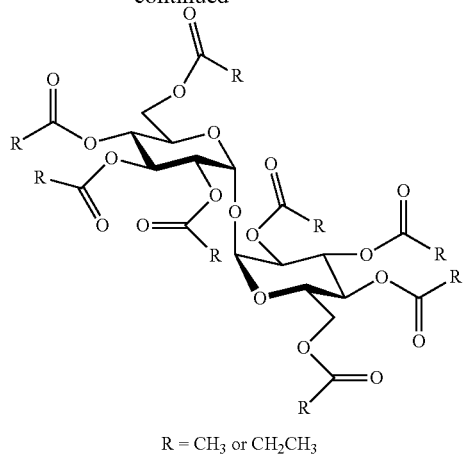

R = CH₃ or CH₂CH₃

Synthesis a): D-Trehalose dihydrate (5 g, 13.2 mmol) was suspended under inert atmosphere in 50 mL dry pyridine followed shortly hereafter by addition of acetic anhydride (15 mL, 159 mmol, ~12 eq.) and propionic anhydride (10 mL, 78 mmol, ~6 eq.) roughly in a 2:1 relationship (acetic anhydride was added first, shortly hereafter, propionic anhydride was added). Hereafter a catalytic amount of DMAP (~166 mg, 1.4 mmol, ~0.1 eq) was added. The reaction was conducted under inert atmosphere at r.t. for 1.5 days. Then TLC (20% acetone, toluene) showed that the reaction was done (approximately 5 spots from rf ~0.3-0.5). Then followed evaporation of the solvent and anhydride, with co-evaporation of toluene (2×20 mL) to remove the residual anhydride. The final purification consisted of dissolution in CHCl₃ (100 mL) and washing with NaHCO₃ (aq) (4×100 mL), water (2×100 mL) and brine (1×100 mL). The organic phase was then dried with MgSO₄ (s), filtered, concentrated under reduced pressure and dried in vacuuo. Yield: 6.4 g (~69%, calculated after the expected weight of overall ~3:1 acetate:propionate mixture in the resulting product (confirmed by ¹H-NMR)). ¹H-NMR (400 MHz, Chloroform-d): δ 5.54-5.44 (m, 10H, H-1 and H-1'), 5.32-5.25 (m, 10H), 5.10-4.99 (m, 20H), 4.23 (m, 10H), 4.08-3.95 (m, 20H), 2.41-2.21 (m, ~20H, CH₂ propionate), 2.11-1.97 (m, ~90H, CH₃ Acetate), 1.19-1.05 (m, ~30H, CH₃ propionate). MALDI TOF-MS: Uniformly acetylated compound [M+Na]⁺: Calc.: 701.59. Found: 701.61. Compound with 7 acetyl groups and one propionyl group [M+Na]⁺: Calc.: 715.62. Found: 715.66. Compound with 6 acetyl groups and two propionyl groups [M+Na]⁺: Calc.: 729.65. Found: 729.70. Compound with 5 acetyl groups and three propionyl groups: [M+]⁺: Calc.: 743.67. Found: 743.74. Compound with 4 acetyl groups and 4 propionyl groups: [M+Na]⁺: Calc.: 757.70. Found: 757.75.

Synthesis b): D-Trehalose dihydrate (5 g, 13.2 mmol) was suspended under inert atmosphere in 50 mL dry pyridine followed shortly hereafter by addition of acetic anhydride (11 mL, 116.6 mmol, 8.8 eq) and propionic anhydride (15 mL, 116.9 mmol, ~8.9 eq) in a ~1:1 relationship (acetic anhydride was added first, shortly after propionic anhydride was added). Hereafter a catalytic amount of DMAP (~165 mg, 1.4 mmol, ~0.1 eq) was added. The reaction was conducted under inert atmosphere at r.t. for 1.5 days. Then TLC (20% acetone, toluene) showed that the reaction was done (approximately ~6 spots from rf ~0.3-0.6). Then followed evaporation of the solvent and anhydride with co-evaporation of toluene (2×20 mL) to remove the residual anhydride. The final purification consisted of dissolution in CHCl$_3$ (100 mL) and washing with NaHCO$_3$ (aq) (4×100 mL), water (2×100 mL) and brine (1×100 mL). The organic phase was then dried with MgSO$_4$ (s), filtered, concentrated under reduced pressure and dried in vacuuo. Yield: 6.9 g (~73% yield, calculated after overall ~2:1 Acetate:propionate mixture in the resulting product (confirmed by $^1$H-NMR)). $^1$H-NMR (400 MHz, Chloroform-d): δ 5.54-5.45 (m, 12H. H-1 and H-1'), 5.32-5.25 (m, 12H), 5.10-4.99 (m, 24H), 4.27-4.17 (m, 12H), 4.09-3.95 (m, 24H), 2.40-2.21 (m, 32H, CH$_2$ propionate), 2.11-1.97 (m, 96H, CH$_3$ acetate), 1.18-1.04 (m, 48H, CH$_3$ propionate). MALDI TOF-MS: Uniformly acetylated compound [M+Na]$^+$: Calc.: 701.59. Found: 701.61. Compound with 7 acetyl groups and one propionyl group [M+Na]$^+$: Calc.: 715.62. Found: 715.68. Compound with 6 acetyl groups and two propionyl groups [M+Na]$^+$: Calc.: 729.65. Found: 729.73. Compound with 5 acetyl groups and three propionyl groups: [M+Na]$^+$: Calc.: 743.67. Found: 743.77. Compound with 4 acetyl groups and 4 propionyl groups: [M+Na]$^+$: Calc.: 757.70. Found: 757.79. Compound with 3 acetyl groups and 5 propionyl groups: [M+Na]$^+$: Calc.: 771.73. Found: 771.81.

Example II

Gel Formation

The gel-forming properties of the synthesized esters containing only small percentages of organic solvents and/or triglycerides were inspected in the following experiments
Gels Formulated with EtOH:
~210 mg of the following sugar ester formulations: α,β Lactose octaacetate: α,β Lactose octaisobutyrate 5:1, α,β Lactose octaacetate: α,β Lactose octaisobutyrate 2:1, α,β Lactose octaacetate: α,β Lactose octaisobutyrate 1:1, α,β Lactose octaacetate: α,β Lactose octapropionate 1:1, α,β Lactose octaacetate: α,β Lactose octapropionate 1:5, α,β Lactose octaacetate: α,β Lactose octapropionate 1:3, α,β Lactose octapropionate: α,β Lactose octaisobutyrate 1:1, α,β Lactose octaacetate: α,β Lactose octaisobutyrate 1:5, α,β Lactose octapropionate, α,β Lactose octaisobutyrate: α,β Lactose octaacetate 0.5:0.5:5, α,β Lactose octaisobutyrate: α,β Lactose octaacetate 3:1, Trehalose octaacetate: Trehalose octapropionate 1:1, Trehalose octapropionate, Trehalose octaisobutyrate, Raffinose undecaacetate: Raffinose undecapropionate 1:1, Raffinose undecaisobutyrate, β-maltose octaisobutyrate and α,β-D-glucosamine pentapropionate were mixed with 20 wt % EtOH by heating to ~37° C., vortexing and ultrasonication. ~50-80 uL of the resulting formulations were then injected into 2 mL of PBS buffer using 25 G needles. All of the solutions formed gels upon injection (examples shown in FIG. 1).
Gels Rormulated with DMSO, NMP or Propylene Carbonate:
~210 mg of the following sugar ester formulations: α,β Lactose octaacetate, α,β lactose octapropionate, α,β Lactose octaacetate: α,β lactose octapropionate 1:1, α,β lactose octaisobutyrate, α,β maltose octapropionate, β maltose octapropionate, α-D-glucosamine pentapropionate, α, β-D-glucosamine pentapropionate, β maltose octapropionate: α-D-glucosamine pentapropionate 1:1 and α-D-glucosamine pentaisobutyrate were mixed with 20 wt % NMP or DMSO by heating to ~37° C., vortexing and ultrasonication. ~50-60 uL of the resulting formulations were injected into PBS. With maltose octapropionate, glucosamine pentapropionate and lactose octaacetate alternative wt % of solvents were also tried (i.e. 25-40 wt % of the before mentioned solvents). In all cases, formation of an amorphous solid (gel) was seen.

In case of α,β-maltose propionate and α,β-D-glucosamine pentapropionate, injection into PBS and gel-formation are also successful when formulated with 35% and 20% propylene carbonate, respectively (examples shown in FIG. 1). Pure α-D-Glucosamine esters and hydrophilic maltose ester analogues have a tendency to form hard amorphous solids with some crystallinity after injection into PBS—so although ~20 wt % solvent is possible to inject with difficulty, gels of this type containing ~25-35 wt % solvent are easier to handle. Although, pure acetylated esters such as lactose octaacetate are injectable in 20 wt % DMSO or 20 wt % propylene carbonate, this occurs with difficulty due to high viscosity of the resulting formulation—~30-40 wt % solvent (EtOH, DMSO/NMP or propylene carbonate) is more appropriate for forming injectable gels of pure acetyl esters.
Gels Formulated with Triglyceride:
~210 mg of α,β Lactose octaacetate: α,β Lactose octapropionate 1:1 or α,β Lactose octaisobutyrate were mixed with 2, 5 or 10 wt % glycerol trioctanoate, 5% DMSO and EtOH was added to give 20 wt % solvent in total for all formulations. In case of lactose octaisobutyrate, formulations containing 15 wt % glycerol trioctanoate and 5% DMSO, 30 wt % glycerol trioctanoate and 5% NMP/DMSO or 40 wt % glycerol trioctanoate alone were also made. The solutions were mixed by heating to ~37° C., vortexing and ultrasonication. ~40-60 uL of the resulting formulations were injected into PBS. In all cases, formation of an amorphous solid (gel) was seen. In case of pure triglyceride used as "solvent", the injected solid was very soft, transparent and could easily be manipulated in shape by shaking the vial, even 24 h after injection (example shown in FIG. 1).

Example III

In Vitro Release of Fluorophores

The different carbohydrate esters synthesized as described in Example I, were used hereafter in the release experiments. All other chemicals used in the experiments were purchased from CCS Healthcare (absolute ethanol) and Sigma Aldrich (other chemicals) and were used as received from the manufacturer.

Figure 2:
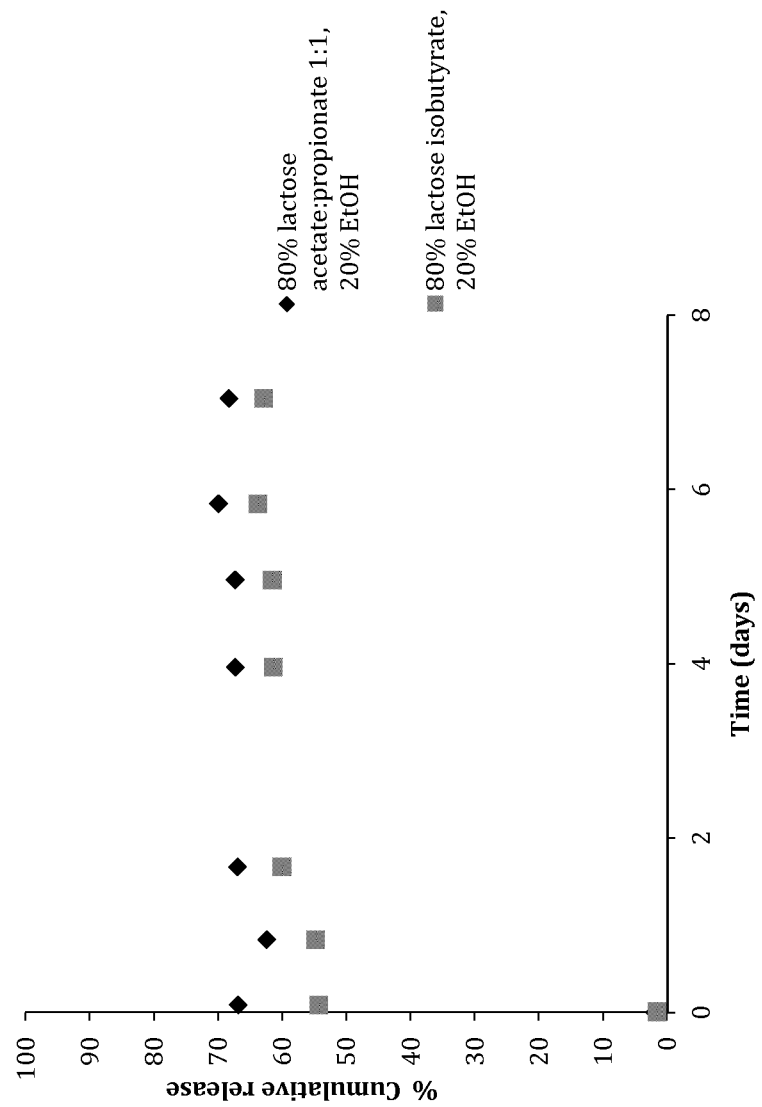
FIG. 2: In vitro release of isoniazide from 80% gel-compositions with different hydrophobicities.
Figure 3:
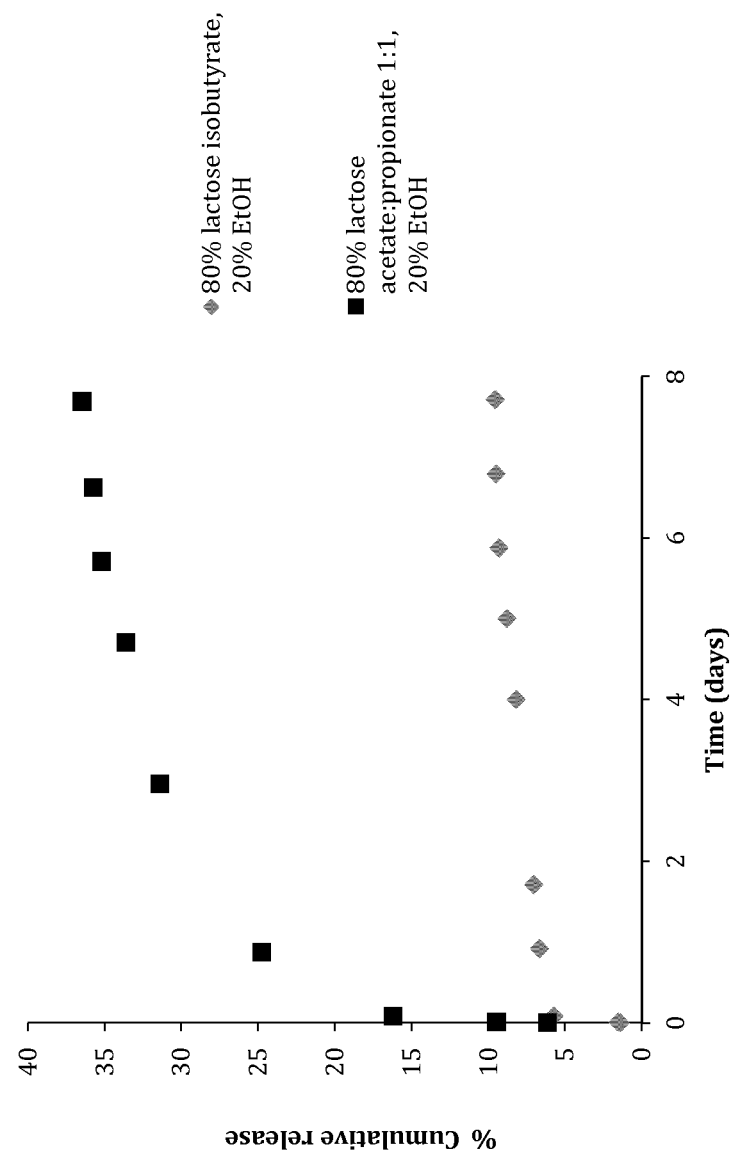
FIG. 3: In vitro release of fluorescein from 80% gel-compositions with different hydrophobicities.

General experimental conditions: In vitro release kinetics of different compounds from carbohydrate ester formulations were examined after injection of small droplets of 75-80% gel forming carbohydrate, and 20% non-toxic water miscible solvent through 21-25 G hyperdermic needles into PBS buffer (2 mL). The experiments were kept at 37° C. and small aliquots of PBS (10 μL) were removed at specific time intervals and replaced with fresh buffer. The amount of released fluorophore was determined by UV-vis spectroscopy on a Thermo Scientific Nano Drop 2000 C spectrophotometer using standard curves with known concentrations.
Fluorophore: Isoniazide
~204 mg of lactose isobutyrate or lactose acetate:lactose propionate (1:1) (80%) were mixed with 20% absolute EtOH and isoniazide (Log P ~-0.8) to give concentrations of ~5 μg/μL in the gel. 50 and 80 μL of the lactose acetate: lactose propionate 1:1 gel and the lactose isobutyrate gel respectively were injected into PBS. Cumulative release was measured by UV-vis at 263 nm (see FIG. 2).
Fluorophore: Fluorescein Free Acid
~204 mg of lactose isobutyrate or ~231 mg of lactose acetate:lactose propionate (1:1) (80%) were mixed with 20% absolute EtOH and fluorescein free acid (Log P-~1.8) to give concentrations of ~1.7 μg/μL in the gel. 70 μL of each solution was injected into PBS. Cumulative release was measured by UV-vis at 490 nm (see FIG. 3).

Fluorophore: Eosin Y

Figure 4:
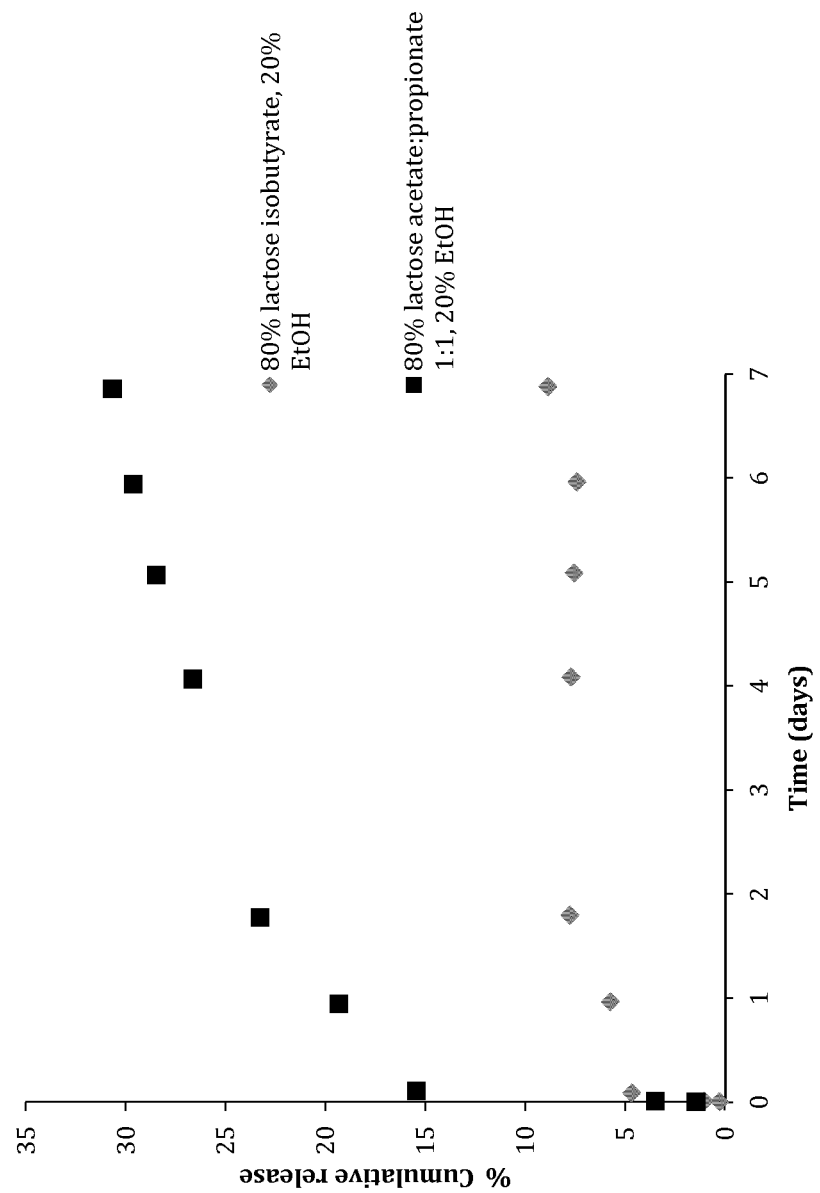
FIG. 4: In vitro release of Eosin Y from 80% gel-compositions with different hydrophobicities.

~204 mg of lactose isobutyrate or lactose acetate:lactose propionate (1:1) (80%) were mixed with 20% absolute EtOH and Eosin Y (Log P ~6.4) to give concentrations of ~2.4 μg/μL in the gel. 50 and 80 μL of the lactose acetate:lactose propionate 1:1 gel and the lactose isobutyrate gel respectively were injected into PBS. Cumulative release was measured by UV-vis at 515 nm (see FIG. 4).

Example IV

In Vitro Release of Chemotherapeutics

The different carbohydrate esters synthesized as described in Example I, were synthesized and used hereafter in the release experiments. All other chemicals used in the experiments were purchased from CCS Healthcare (absolute ethanol) and Sigma Aldrich (other chemicals) and were used as received from the manufacturer.

General experimental conditions: In vitro release kinetics of different compounds from carbohydrate ester formulations were examined after injection of small droplets of 49-80% gel forming carbohydrate, 0-50% additive (PLA/PLGA/cellulose acetate butyrate (CAB)/glycerol ester) and 20-30% non-toxic water miscible solvent through 21-25 G hyperdermic needles into PBS buffer (2 mL). The experiments were kept at 37° C. and small aliquots of PBS (10 μL unless otherwise noted) were removed at specific time intervals and replaced with fresh buffer. All percentages given in gel-compositions are weight % (% w/w). The amount of released chemotherapeutics was determined by UV-vis spectroscopy on a Thermo Scientific Nano Drop 2000 C spectrophotometer using standard curves with known concentrations.

Chemotherapeutic: 5-fluorouracil

Figure 5:
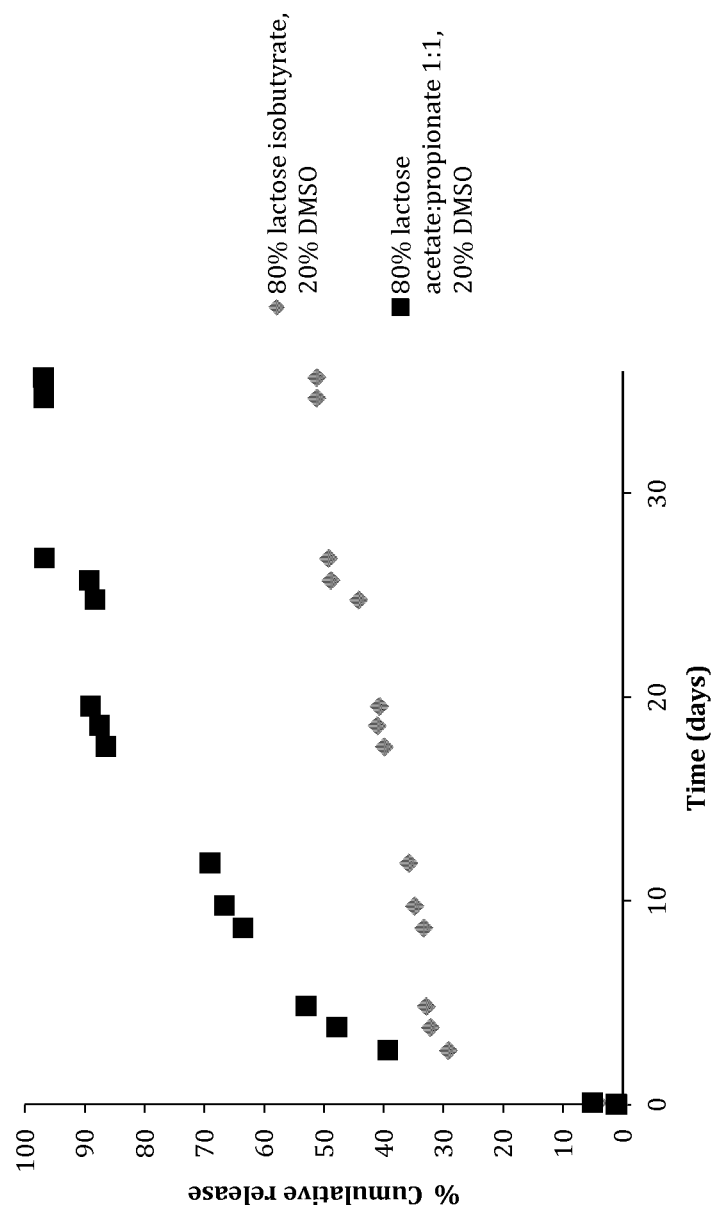
FIG. 5: In vitro release of 5-fluorouracil (5-FU) from 80% gel-compositions with different hydrophobicity.

~220 mg of lactose isobutyrate or lactose acetate:lactose propionate (1:1) (80%) were mixed with 20% DMSO containing 5-fluorouracil (5-FU) to give concentrations of ~5 μg/μL in the gel. 50 μL of each solution was injected into PBS. Cumulative release was measured by UV-vis at 265 nm (see FIG. 5).

Figure 6:
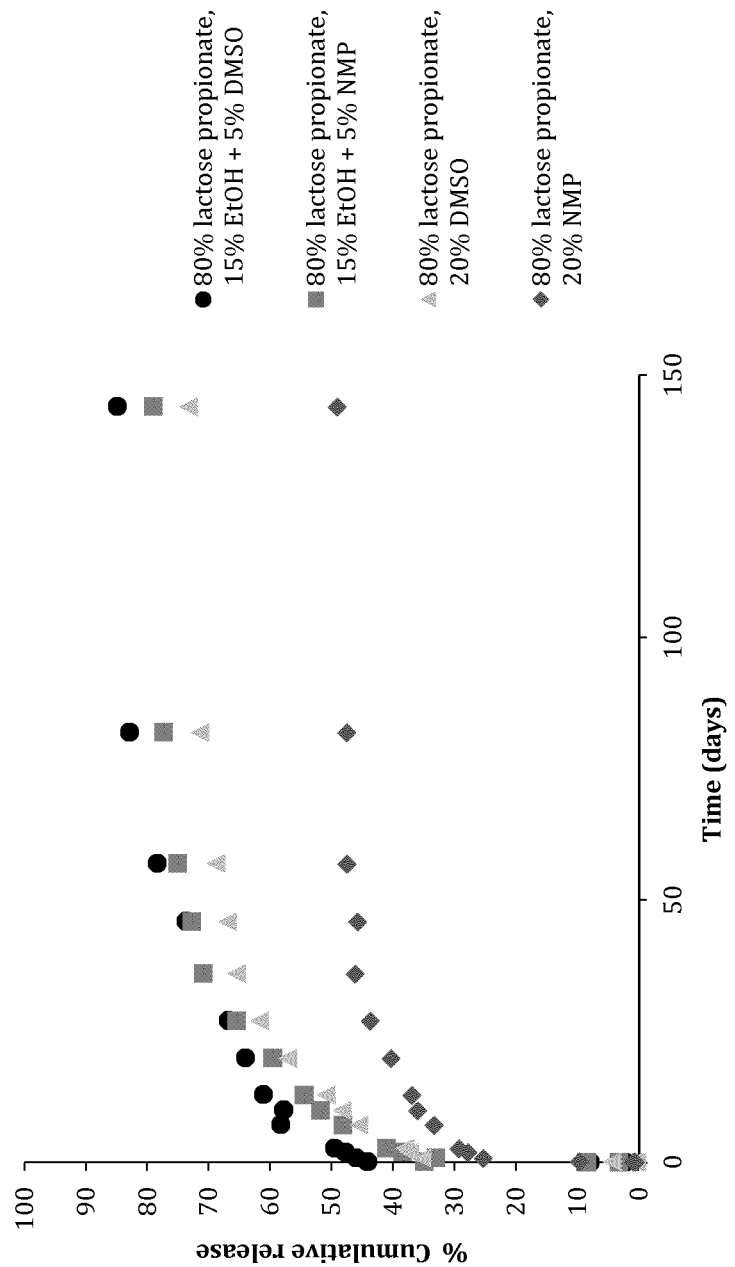
FIG. 6: In vitro release of 5-fluorouracil (5-FU) from 80% gel-compositions of lactose propionate formulations.

~210 mg of lactose propionate (80%) were mixed with different solvents (20% DMSO, 20% NMP, 5% DMSO and 15% absolute EtOH or 5% NMP and 15% absolute EtOH) containing 5-FU to give an average concentration of ~5 μg/μL in the gels. ~40-70 μL of each solution was injected into PBS. Cumulative release was measured by UV-vis at 265 nm (see FIG. 6).

Figure 7:
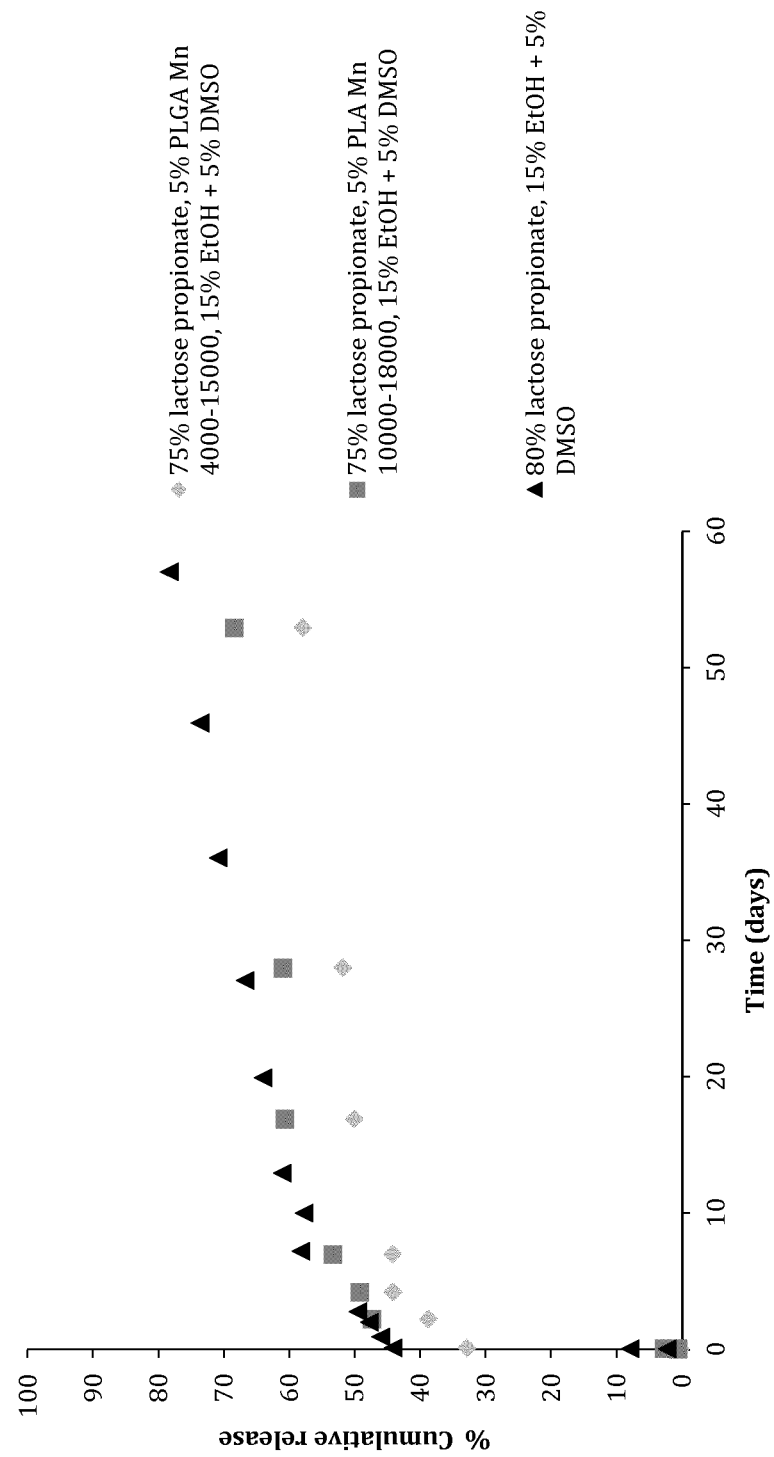
FIG. 7: In vitro release of 5-fluorouracil (5-FU) from 75% lactose propionate+5% additive and 80% lactose propionate formulations.

~224 mg of lactose propionate (75%) and 5% of different additives (PLGA Mn 4000-15,000 or PLA Mn 10,000-18,000) were mixed with 5% DMSO and 15% EtOH containing 5-FU to give average concentrations of ~5 μg/μL in the gels. 80 μL of both gels were injected into PBS. The gel-formulation containing no PLA was formulated according to FIG. 6 for 80% lactose propionate containing 15% EtOH and 5% DMSO, and 40 μL of the gel was injected into PBS. Cumulative release was measured by UV-vis at 265 nm (see FIG. 7).

Figure 8:
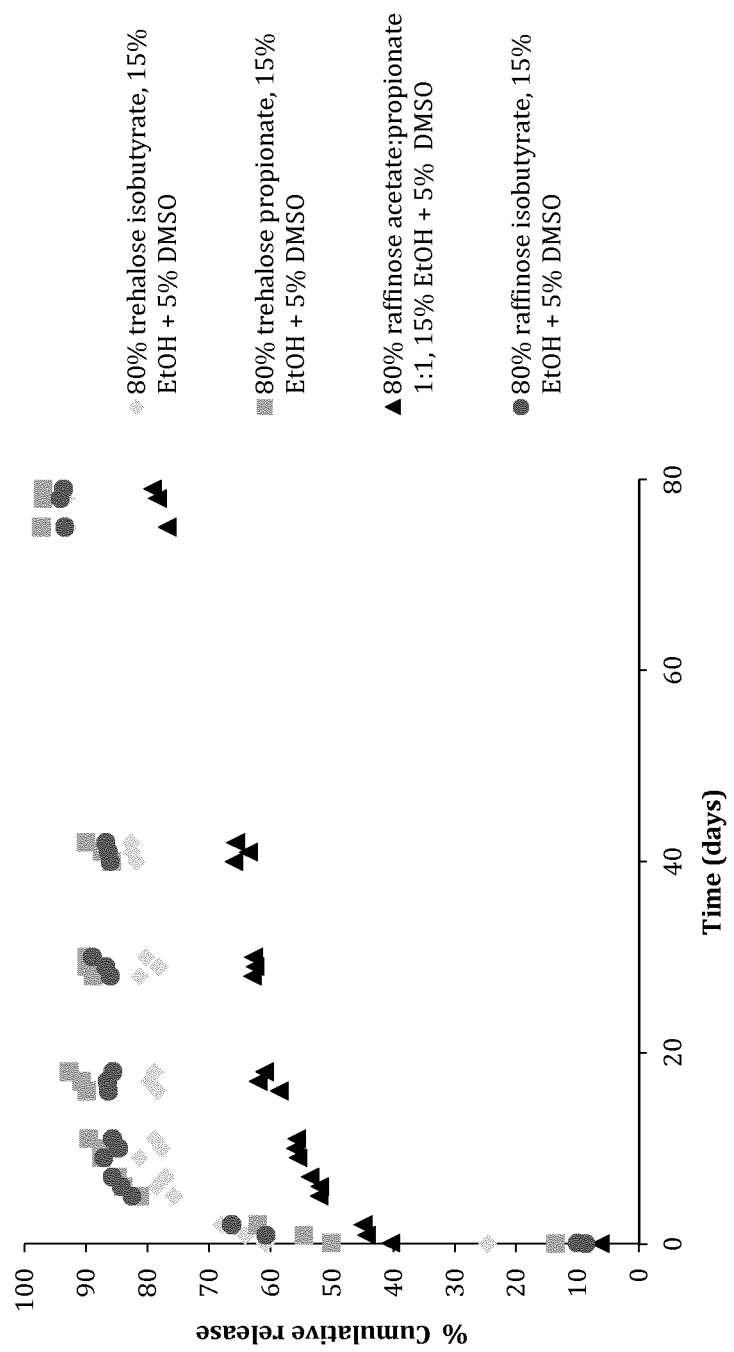
FIG. 8: In vitro release of 5-fluorouracil (5-FU) from raffinose and trehalose ester formulations consisting of 80% gel-forming carbohydrate material and 20% solvent.

~210 mg of trehalose isobutyrate, trehalose acetate:propionate 1:1, Raffinose isobutyrate and raffinose acetate:propionate 1:1 were mixed with 15% EtOH and 5% DMSO containing 5-FU to give average concentrations of ~3 μg/μL in the gels. ~70 μL of the formulations were injected into PBS. Cumulative release was measured by UV-vis at 265 nm (FIG. 8).

Figure 9:
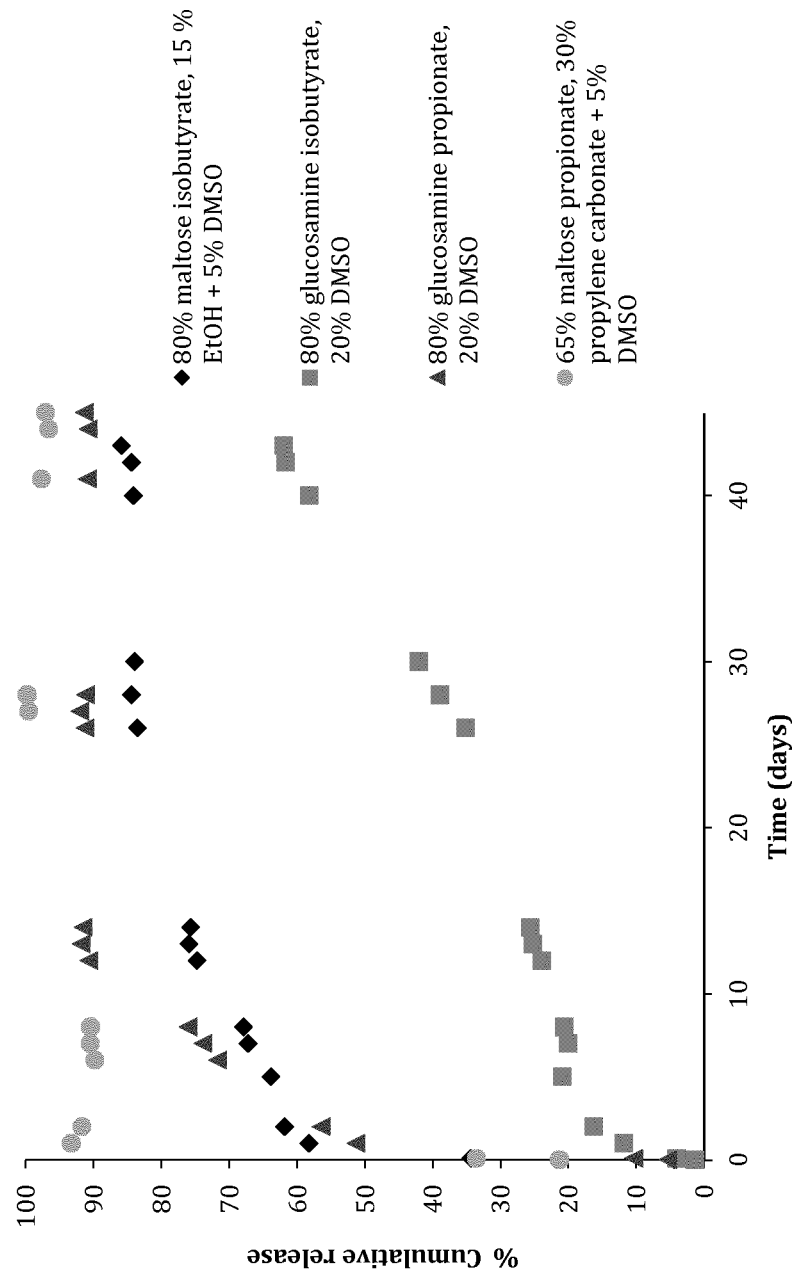
FIG. 9: In vitro release of 5-fluorouracil (5-FU) from glucosamine and maltose ester formulations consisting of 80-65% gel-forming carbohydrate material and 20-35% solvent.

~170-210 mg of glucosamine isobutyrate, glucosamine propionate, maltose isobutyrate and maltose propionate were mixed with different solvents containing 5-FU. In case of the glucosamine esters, 20% DMSO was used, while maltose isobutyrate and maltose propionate were mixed with 15% EtOH and 30% propylene carbonate respectively with 5% DMSO containing 5-FU to give average concentrations of ~3 μg/μL in the gels. ~20-70 μL of the formulations were injected into PBS. Cumulative release was measured by UV-vis at 265 nm (see FIG. 9).

Figure 10:
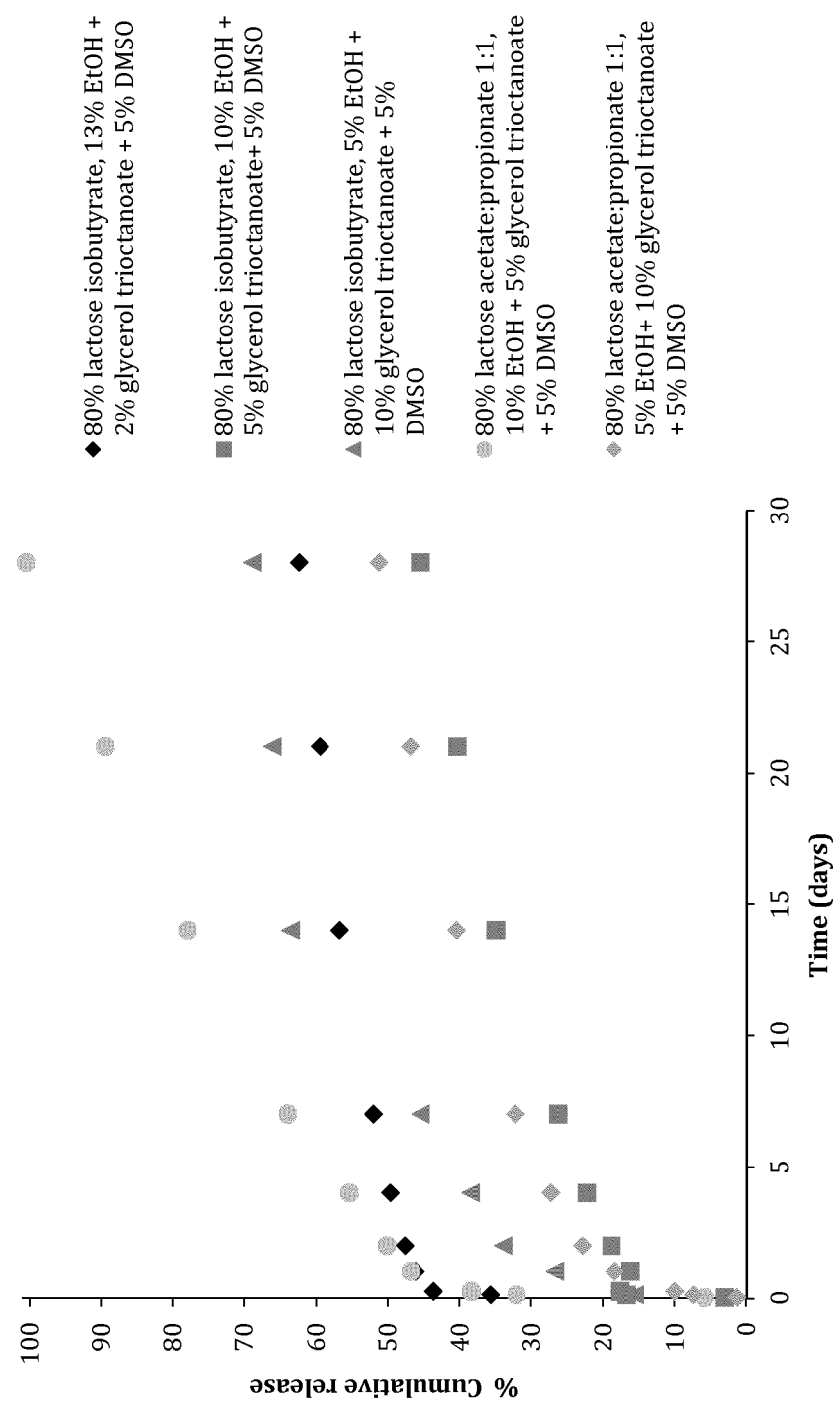
FIG. 10: In vitro release of 5-fluorouracil (5-FU) from lactose esters formulations.

~300 mg of lactose isobutyrate (80%) or lactose acetate:propionate 1:1 was mixed with 2, 5 or 10% glycerol trioctanoate, 5% DMSO (containing 5-FU) and EtOH to give a total of 20% solvent. This resulted in an average concentration of ~10 μg/μL 5-FU in the gels. ~40-50 μL of the formulations were injected into PBS. Aliquots of 1 mL buffer were removed at specific time intervals and replaced with clean buffer. Cumulative release was measured by UV-vis at 265 nm (see FIG. 10).

Figure 11:
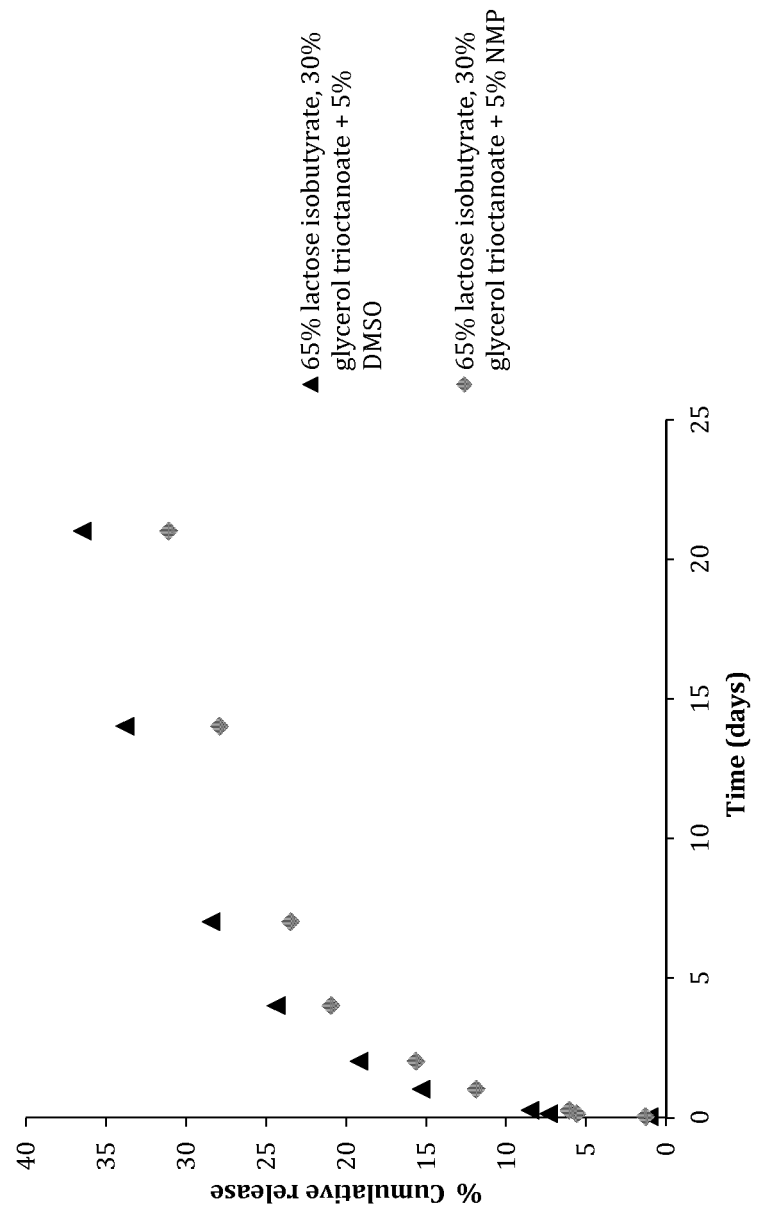
FIG. 11: In vitro release of 5-fluorouracil (5-FU) from lactose isobutyrate formulations.

~300 mg of lactose isobutyrate (65%) was mixed with 30% glycerol trioctanoate and 5% DMSO or 5% NMP containing 5-FU. This resulted in average concentrations of ~11 μg/μL 5-FU in the gels. ~50 μL of the formulations were injected into PBS. Aliquots of 1 mL buffer were removed at specific time intervals and replaced with clean buffer. Cumulative release was measured by UV-vis at 265 nm (see FIG. 11).

Chemotherapeutic: Gemcitabine HCl

Figure 12:
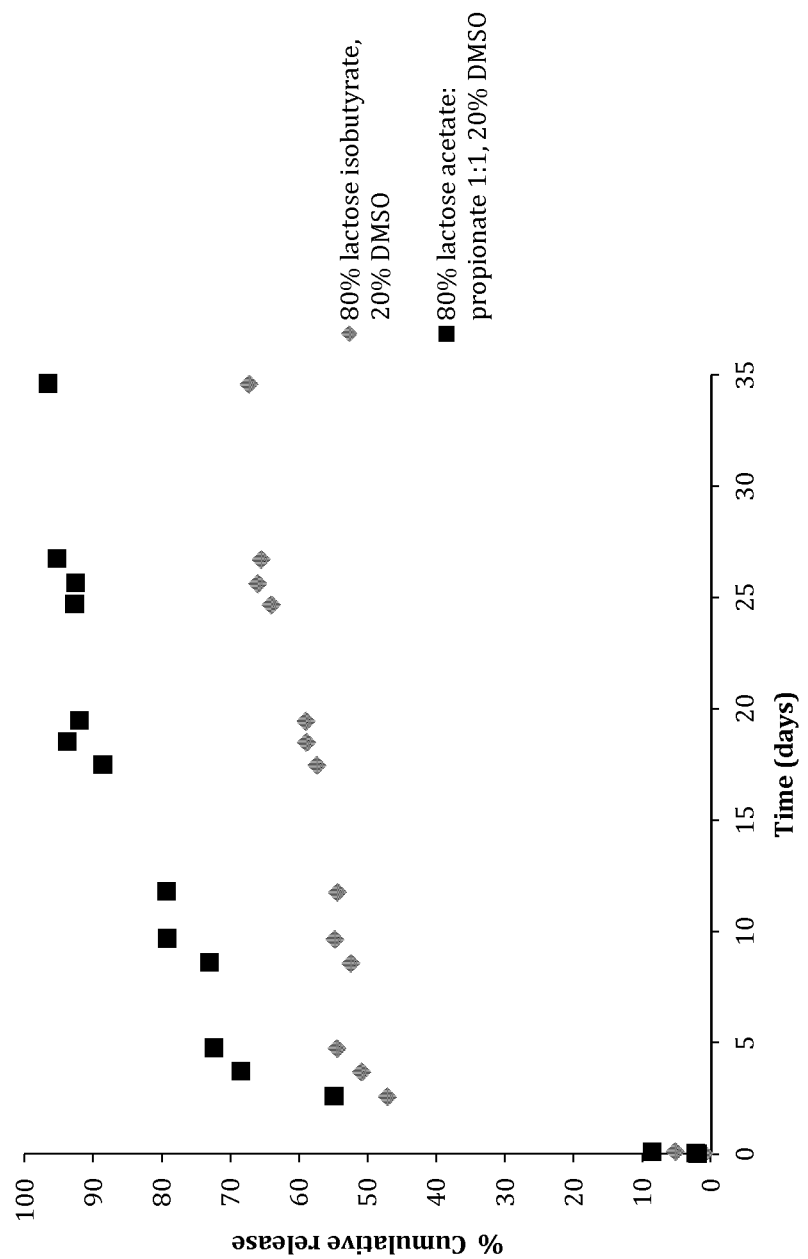
FIG. 12: In vitro release of gemcitabine HCl from 80% lactose ester formulations with different hydrophobicity.

~210 mg of lactose isobutyrate and ~230 mg of lactose acetate:lactose propionate (1:1) (80%) were mixed with 20% DMSO containing Gemcitabine HCl to give concentrations of ~5.5 μg/μL in the gels. 50 and 80 μL of the lactose acetate:lactose propionate 1:1 gel and the lactose isobutyrate gel respectively were injected into PBS. Cumulative release was measured by UV-vis at 268 nm (see FIG. 12).

Figure 13:
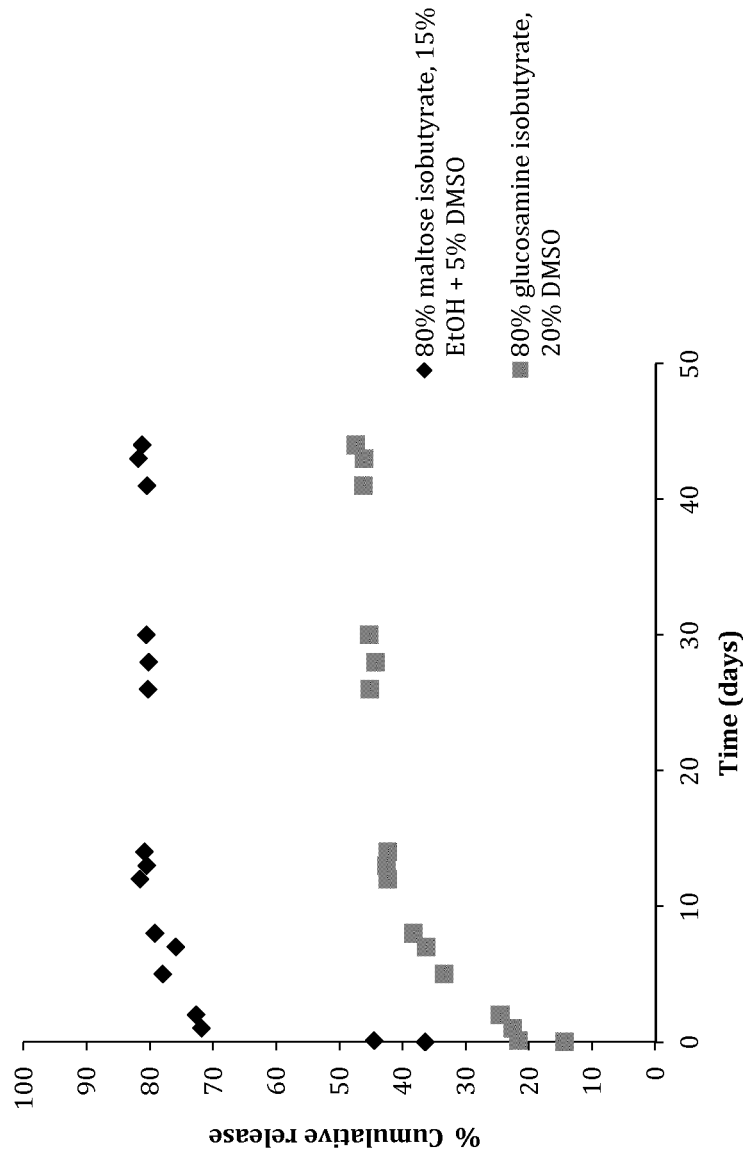
FIG. 13: In vitro release of gemcitabine HCl from 80% maltose and glucosamine ester formulations.

~210 mg of maltose isobutyrate and glucosamine isobutyrate (80%) were mixed with 15% EtOH and 15% DMSO respectively, then 5% DMSO containing Gemcitabine HCl was added to both to give concentrations of ~1.4 μg/μL in the gels. ~70 μL of each gel was injected into PBS. Cumulative release was measured by UV-vis at 268 nm (see FIG. 13).

Figure 14:
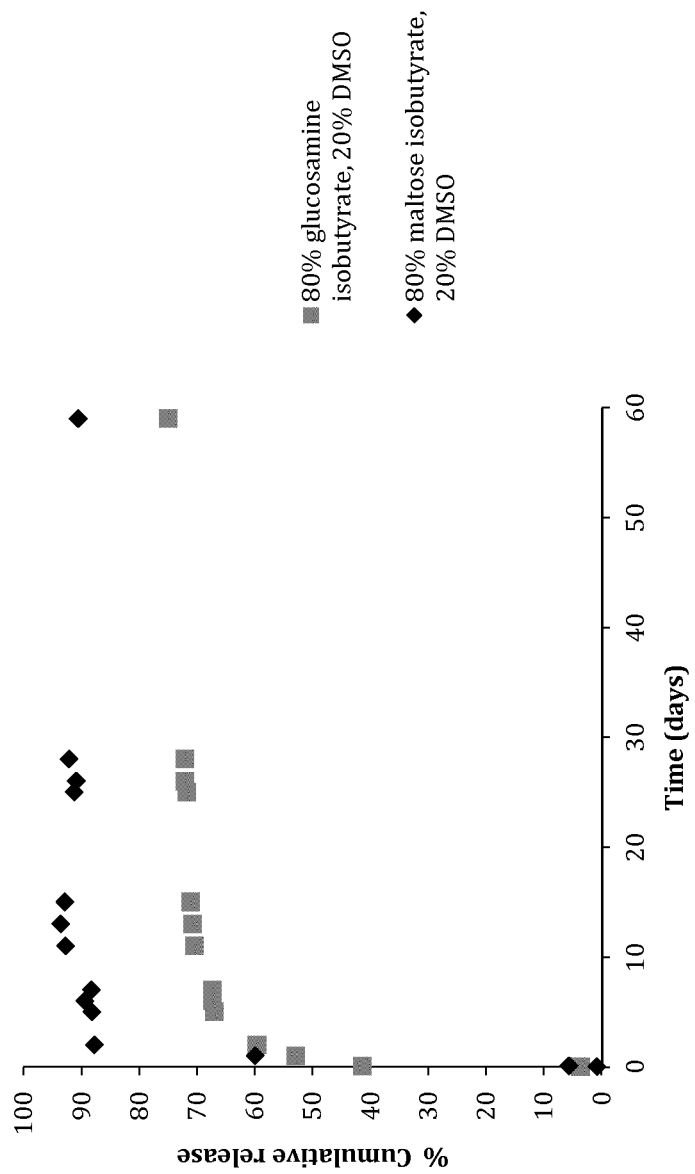
FIG. 14: In vitro release of gemcitabine HCl from 80% maltose and glucosamine ester formulations.
Figure 15:
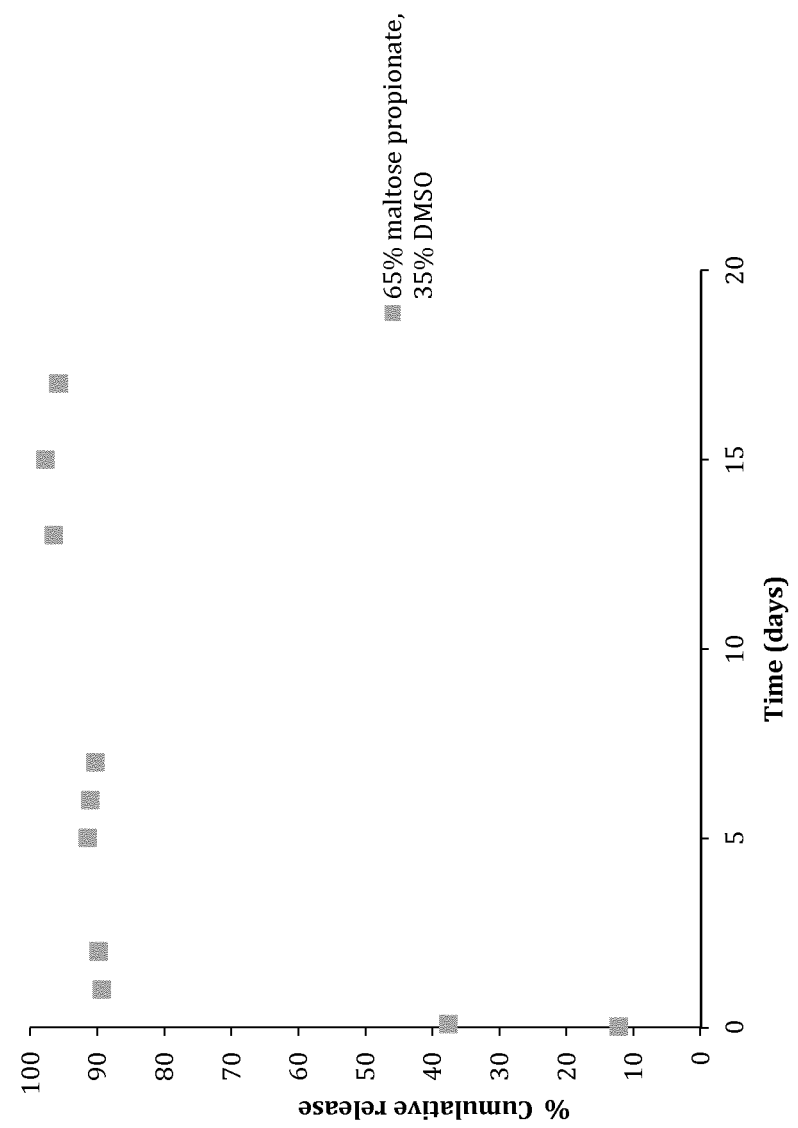
FIG. 15. In vitro release of gemcitabine HCl from maltose propionate formulation.

~210 mg of maltose isobutyrate and glucosamine isobutyrate were mixed with 20% DMSO, whereas ~210 mg of maltose propionate was mixed with 35% DMSO containing Gemcitabine HCl to give average concentrations of ~2-3 μg/μL in the gels. 50-60 μL of the formulations were injected into PBS. Cumulative release was measured by UV-vis at 268 nm (see FIGS. 14 and 15).

Chemotherapeutic: Tirapazamine

Figure 16:
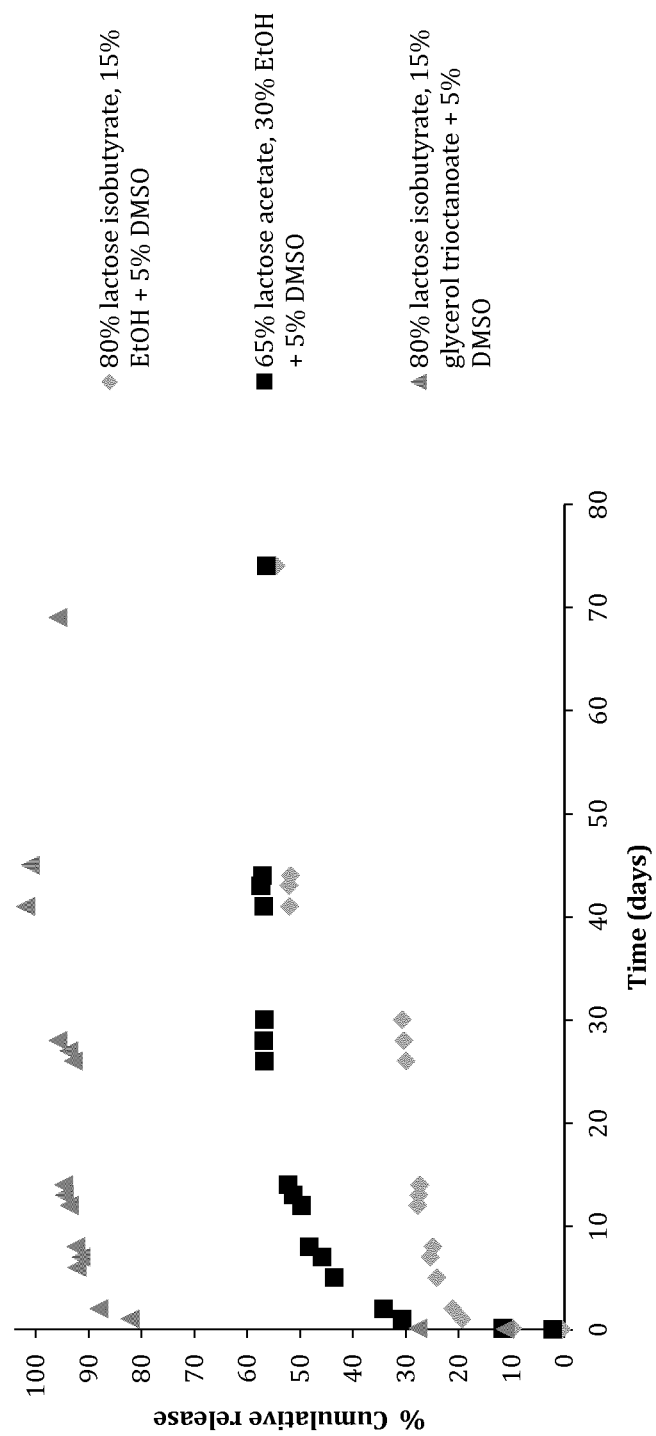
FIG. 16: In vitro release of tirapazamine from 80% lactose ester formulations.

~210 mg of lactose isobutyrate and of lactose acetate were formulated as follows: Lactose isobutyrate was mixed with either 15% EtOH or 15% glycerol trioctanoate, while lactose acetate was mixed with 30% EtOH to form an injectable gel. All gels were mixed with an additional ~5% DMSO containing tirapazamine (Log P ~−0.06) to give concentrations of ~1 μg/μL in the gels. ~20-70 μL of the gels were injected into PBS. Cumulative release was measured by UV-vis at 266 nm (see FIG. 16).

Immunotherapeutic: Resiquimod

Figure 17:
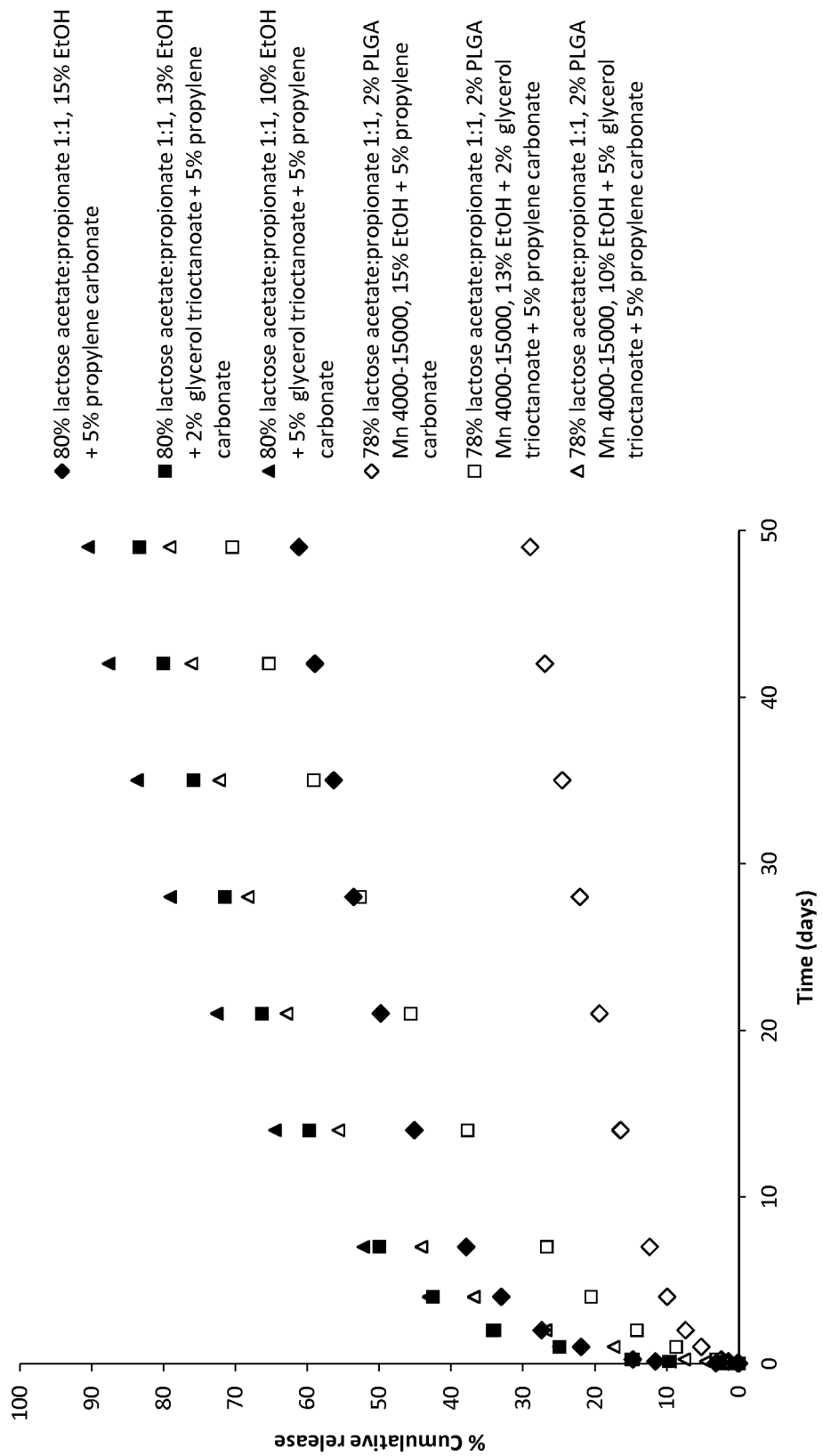
FIG. 17: In vitro release of resiquimod from 80% lactose acetate:proprionate (1:1) formulations.

~300 mg of lactose acetate:propionate (1:1) was mixed with Resiquimod in tBuOH and freeze-dried overnight (or until dry). Secondly, the carbohydrate-drug matrix was mixed with 0, 2, 5, 10, or 15% glycerol trioctanoate, 10% propylene carbonate and 5, 8 or 10% EtOH to give a total of 20-30% solvent. This resulted in an average concentration of ~1.78 μg/μL Resiquimod in the gels. ~50 μL of the formulations was injected into 2 mL PBS. Aliquots of 1 mL buffer were removed at specific time intervals and replaced with clean buffer. Cumulative release was measured by fluorescence spectroscopy (excitation: 330 nm, emission: 355 nm) (see FIG. 17a).

~300 mg of lactose acetate:propionate (1:1) was mixed with Resiquimod in tBuOH and freeze-dried overnight (or until dry). Secondly, the carbohydrate-drug matrix was mixed 2% PLGA 75:25 (Mw: 4.000-15.000 kDa) and with 0, 2, 5, 10, or 15% glycerol trioctanoate, 10% propylene carbonate and 5, 8, or 10% EtOH to give a total of 20-30% solvent. This resulted in an average concentration of ~1.78 µg/µL Resiquimod in the gels. ~50 µL of the formulations was injected into 2 mL PBS. Aliquots of 1 mL buffer were removed at specific time intervals and replaced with clean buffer. Cumulative release was measured by fluorescence spectroscopy (excitation: 330 nm, emission: 355 nm) (see FIG. 17b).

Immunotherapeutic: Imiquimod

~300 mg of lactose acetate:propionate (1:1) was mixed with Imiquimod in tBuOH and freeze-dried overnight (or until dry). Secondly, the carbohydrate-drug matrix was mixed with 0, 2, or 5% glycerol trioctanoate, 10% propylene carbonate and 5, 8 or 10% EtOH to give a total of 20% solvent. This resulted in an average concentration of ~2.6 µg/µL Imiquimod in the gels. ~50 µL of the formulations was injected into 2 mL PBS. Aliquots of 1 mL buffer were removed at specific time intervals and replaced with clean buffer. Cumulative release was measured by fluorescence spectroscopy (excitation: 330 nm, emission: 355 nm) (see FIG. 17c).

~300 mg of lactose acetate:propionate (1:1) was mixed with Imiquimod in tBuOH and freeze-dried overnight (or until dry). Secondly, the carbohydrate-drug matrix was mixed 2% PLGA 75:25 (Mw 4.000-15.000 kDa) and with 0, 2, or 5% glycerol trioctanoate, 10% propylene carbonate and 5, 8 or 10% EtOH to give a total of 20-30% solvent. This resulted in an average concentration of ~2.6 µg/µL Imiquimod in the gels. ~50 µL of the formulations was injected into 2 mL PBS. Aliquots of 1 mL buffer were removed at specific time intervals and replaced with clean buffer. Cumulative release was measured by fluorescence spectroscopy (excitation: 330 nm, emission: 355 nm) (see FIG. 17d).

Chemotherapeutic: Gemcitabine

Figure 20:
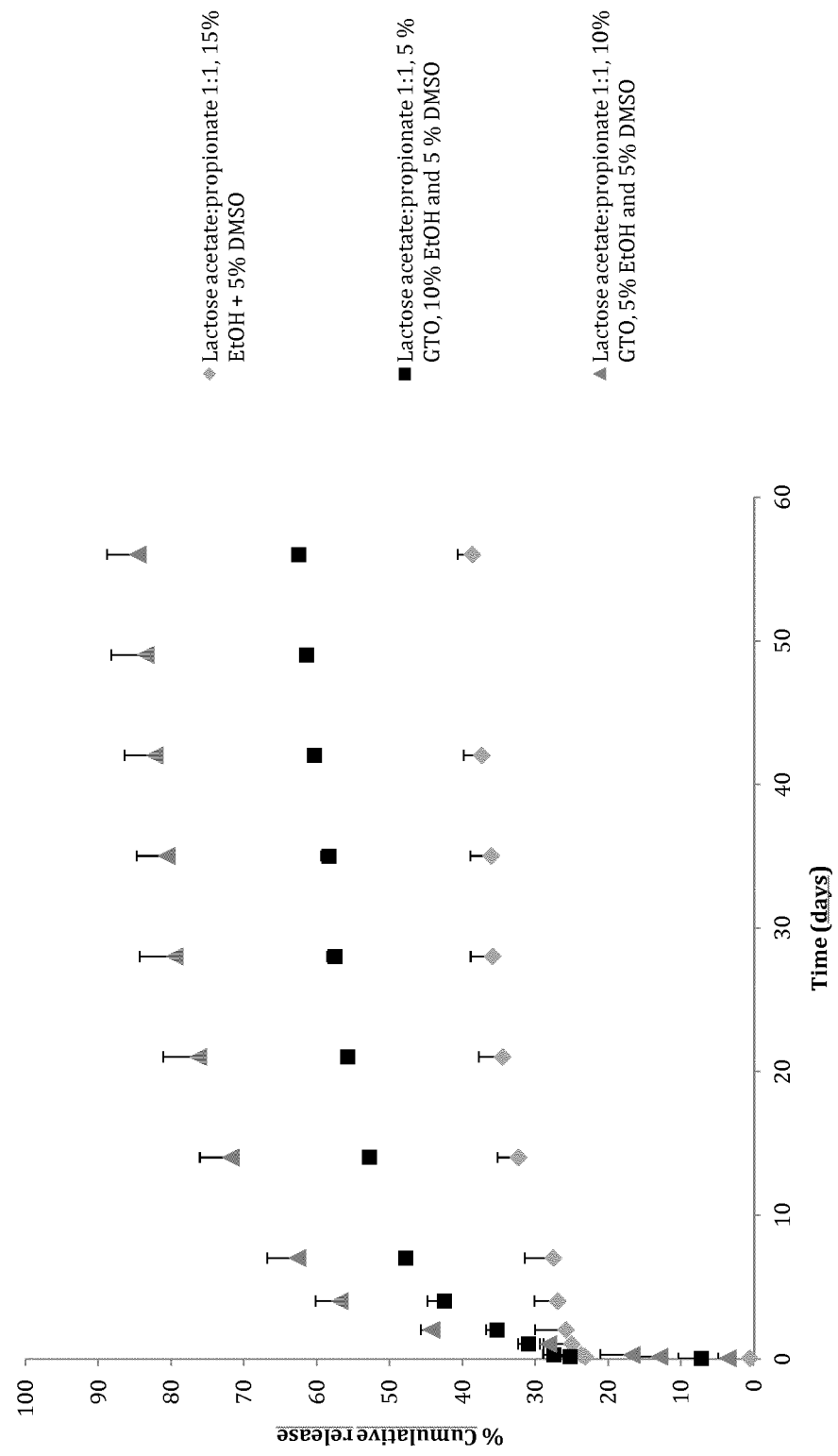
FIG. 20. In vitro release of gemcitabine HCl from lactose acetate:propionate 1:1-triglyceride formulations.

~300 mg of lactose acetate:propionate 1:1 was mixed with 2, 5 or 10% glycerol trioctanoate, 5% DMSO (containing Gemcitabine HCl) and EtOH to give a total of 20% solvent. This resulted in an average concentration of ~9 µg/µL gemcitabine in the gels. ~50 µL of the formulations were injected into PBS. Aliquots of 1 mL buffer were removed at specific time intervals and replaced with clean buffer. Cumulative release was measured by UV-vis at 268 nm (see FIG. 20)

Chemotherapeutic: Lomeguatrib

Figure 21:
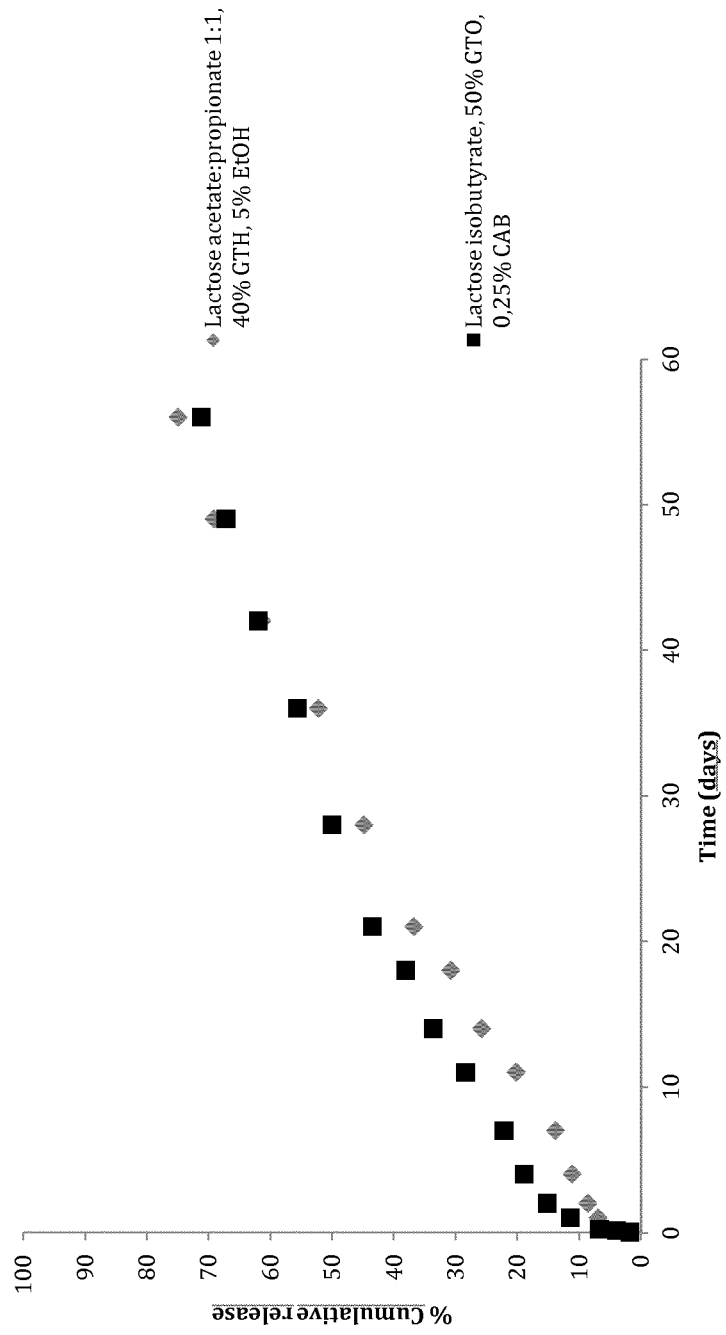
FIG. 21. Release of lomeguatrib from lactose acetate:propionate 1:1 or lactose isobutyrate-triglyceride formulations.

~300 mg of lactose isobutyrate or lactose acetate:propionate 1:1 was mixed with a lomeguatrib solution (in tBuOH/water) and freeze-dried overnight. The resultant carbohydrate-drug matrix was mixed with 40-50% triglyceride (glycerol trioctanoate (GTO) or glycerol trihexanoate (GTH)) along with either 5% EtOH or 0.25% cellulose acetate butyrate (CAB, Mn~12000). This resulted in an average concentration of ~72 µg/µL lomeguatrib in the gels. ~50 µL of the formulations were injected into PBS. Aliquots of 1 mL buffer were removed at specific time intervals and replaced with clean buffer. Cumulative release was measured by UV-vis at 249 nm (see FIG. 21).

Chemotherapeutic: Tirapazamine

Figure 22:
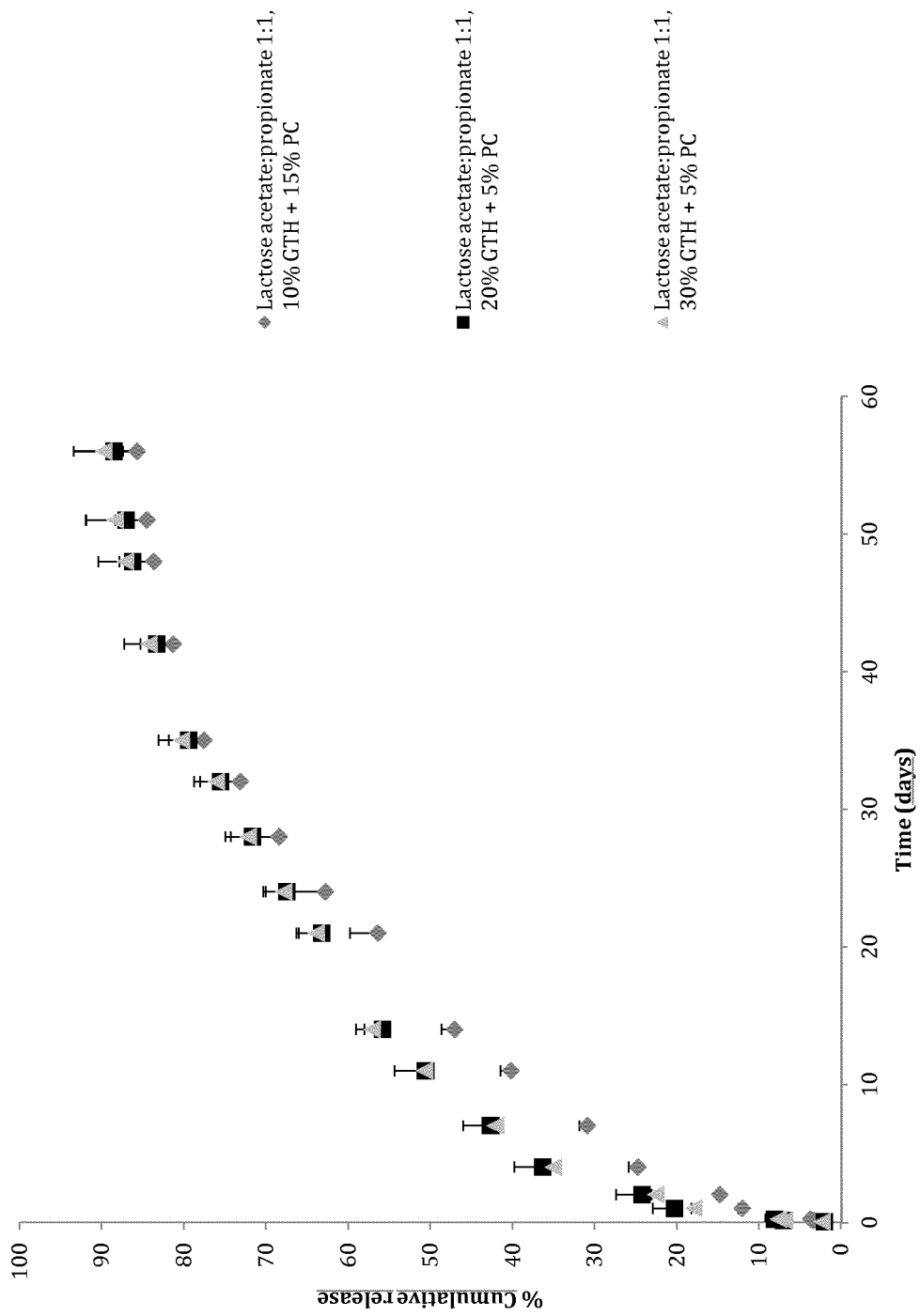
FIG. 22 a): Release of Tirapazamine from lactose acetate:propionate 1:1 and lactose isobutyrate-triglyceride formulations with and without 5-15% propylene carbonate or 1-0.25% cellulose acetate butyrate (Mn~12.000).

~300 mg of lactose isobutyrate or lactose acetate:propionate 1:1 was mixed with a tirapazamine solution (in tBuOH/water) and freeze-dried overnight. The resultant carbohydrate-drug matrix was mixed with 10-50% triglyceride (glycerol trioctanoate (GTO) or glycerol trihexanoate (GTH)) tuning the formulations with 5-15% propylene carbonate or 1-0.25% cellulose acetate butyrate (Mn ~12000). This resulted in an average concentration of ~35 µg/µL tirapazamine in the gels. ~50 µL of the formulations were injected into PBS. Aliquots of 1 mL buffer were removed at specific time intervals and replaced with clean buffer. Cumulative release was measured by UV-vis at 266 nm (see FIG. 22 a and b).

Chemotherapeutic: Temozolomide

Figure 23:
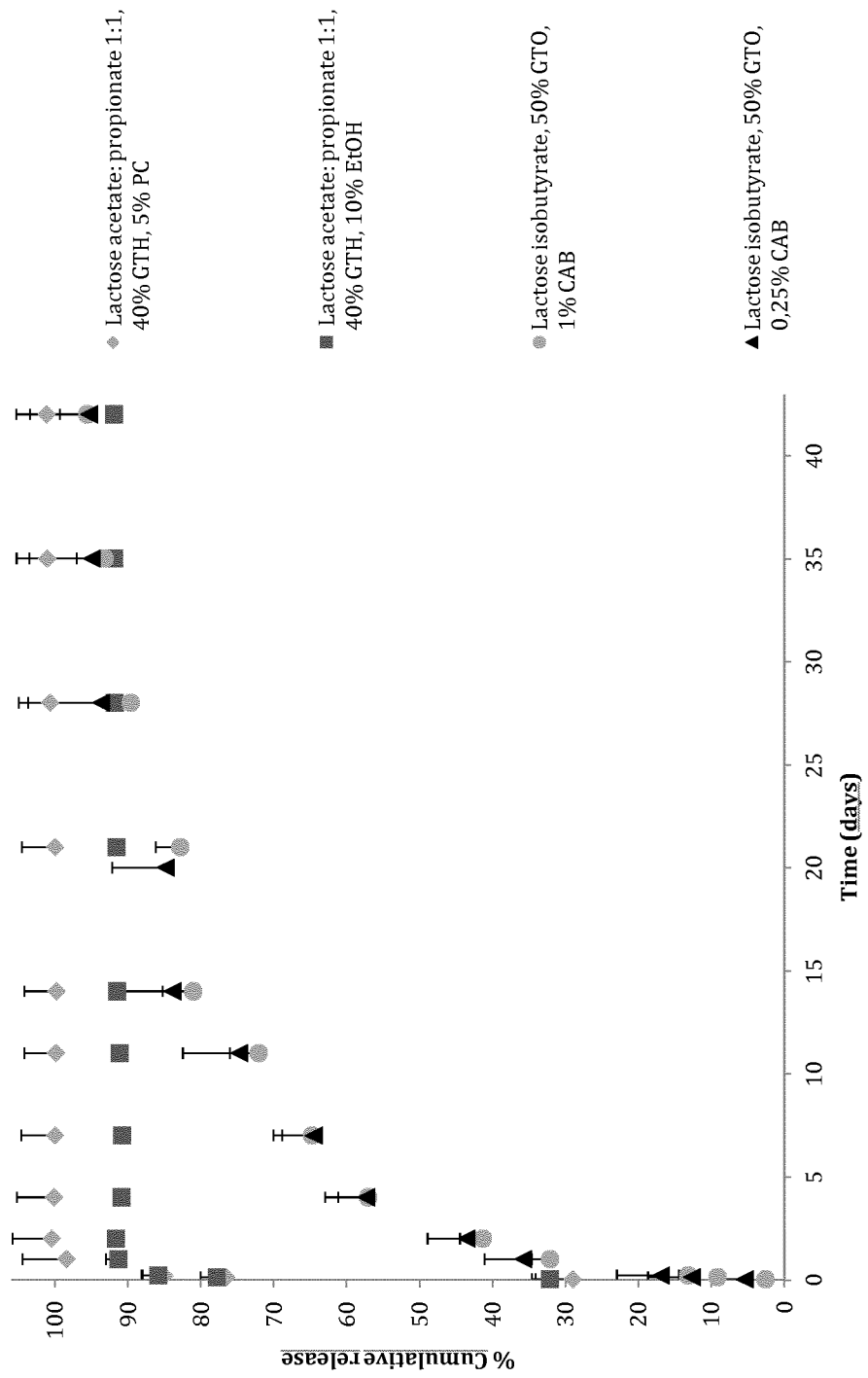
FIG. 23: Release of temozolomide from lactose acetate:propionate 1:1 or lactose isobutyrate-triglyceride formulations with or without 5-10% organic solvent or 1-0.25% Cellulose acetate isobutyrate (CAB).

~300 mg of lactose isobutyrate or lactose acetate:propionate 1:1 was mixed with a temozolomide solution (in tBuOH/water) and freeze-dried overnight. The resultant carbohydrate-drug matrix was mixed with 40-50% triglyceride (glycerol trioctanoate (GTO) or glycerol trihexanoate (GTH)) tuning the formulations with 5-10% propylene carbonate/ethanol or 1-0.25% cellulose acetate butyrate (Mn ~12.000). This resulted in an average concentration of ~15 µg/µL temozolomide in the gels. ~50 µL of the formulations were injected into NaOAc/AcOH buffer. Aliquots of 1 mL buffer were removed at specific time intervals and replaced with clean buffer. Cumulative release was measured by UV-vis at 330 nm (see FIG. 23).

Chemotherapeutic: Methotrexate

Figure 24:
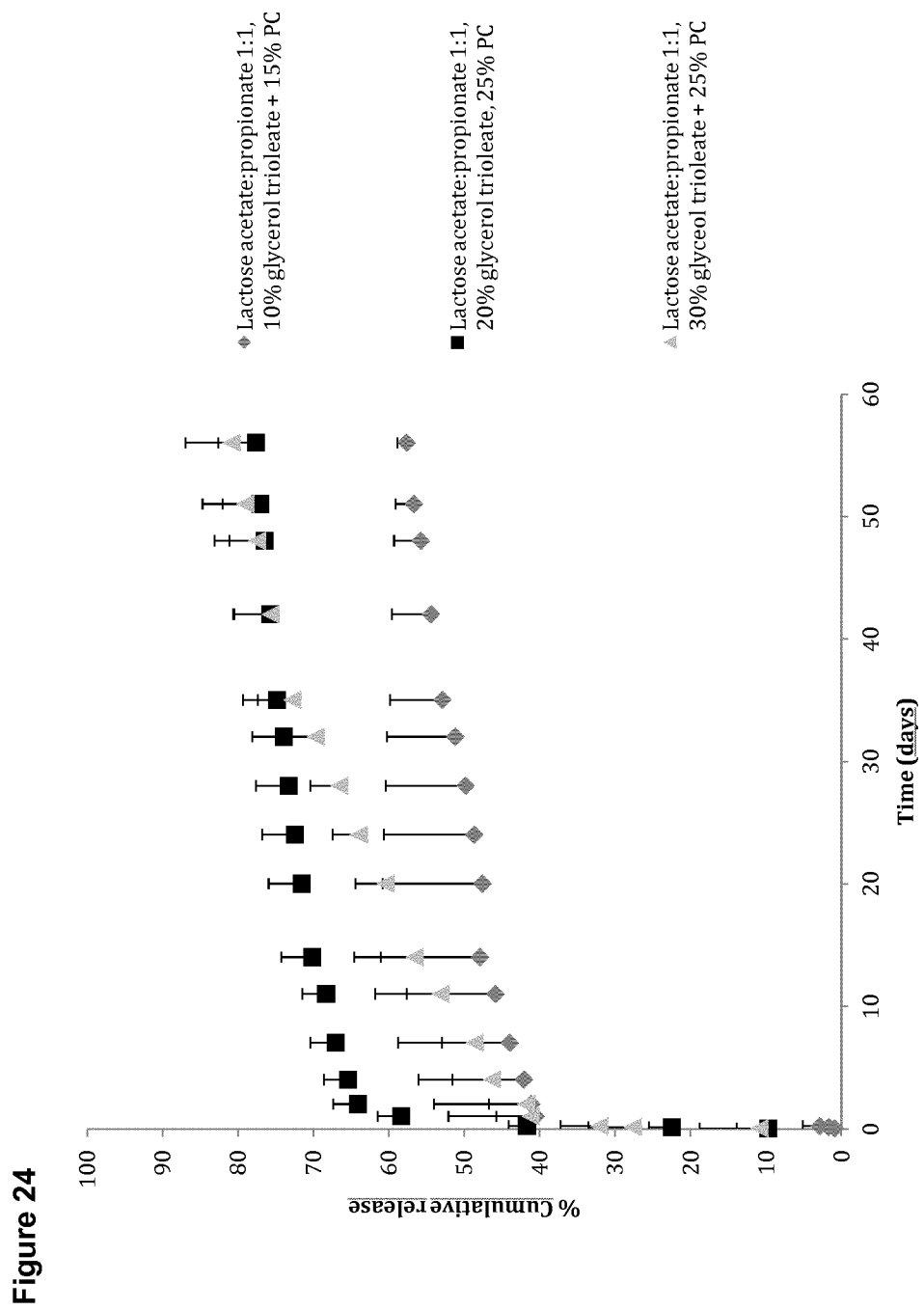
FIG. 24: Release of methotrexate from lactose acetate:propionate 1:1-triglyceride formulations with 15-25% propylene carbonate.

~300 mg of lactose isobutyrate or lactose acetate:propionate 1:1 was mixed with a methotrexate solution (in tBuOH/water) and freeze-dried overnight. The resultant carbohydrate-drug matrix was mixed with 10-30% triglyceride (glycerol trioleate) tuning the formulations with 15-25% propylene carbonate in order to obtain the right viscosity for injectability. This resulted in an average concentration of ~32 µg/µL methotrexate in the gels. ~50 µL of the formulations were injected into PBS. Aliquots of 1 mL buffer were removed at specific time intervals and replaced with clean buffer. Cumulative release was measured by UV-vis at 372 nm (see FIG. 24).

Chemotherapeutic: 5-FU

Figure 25:
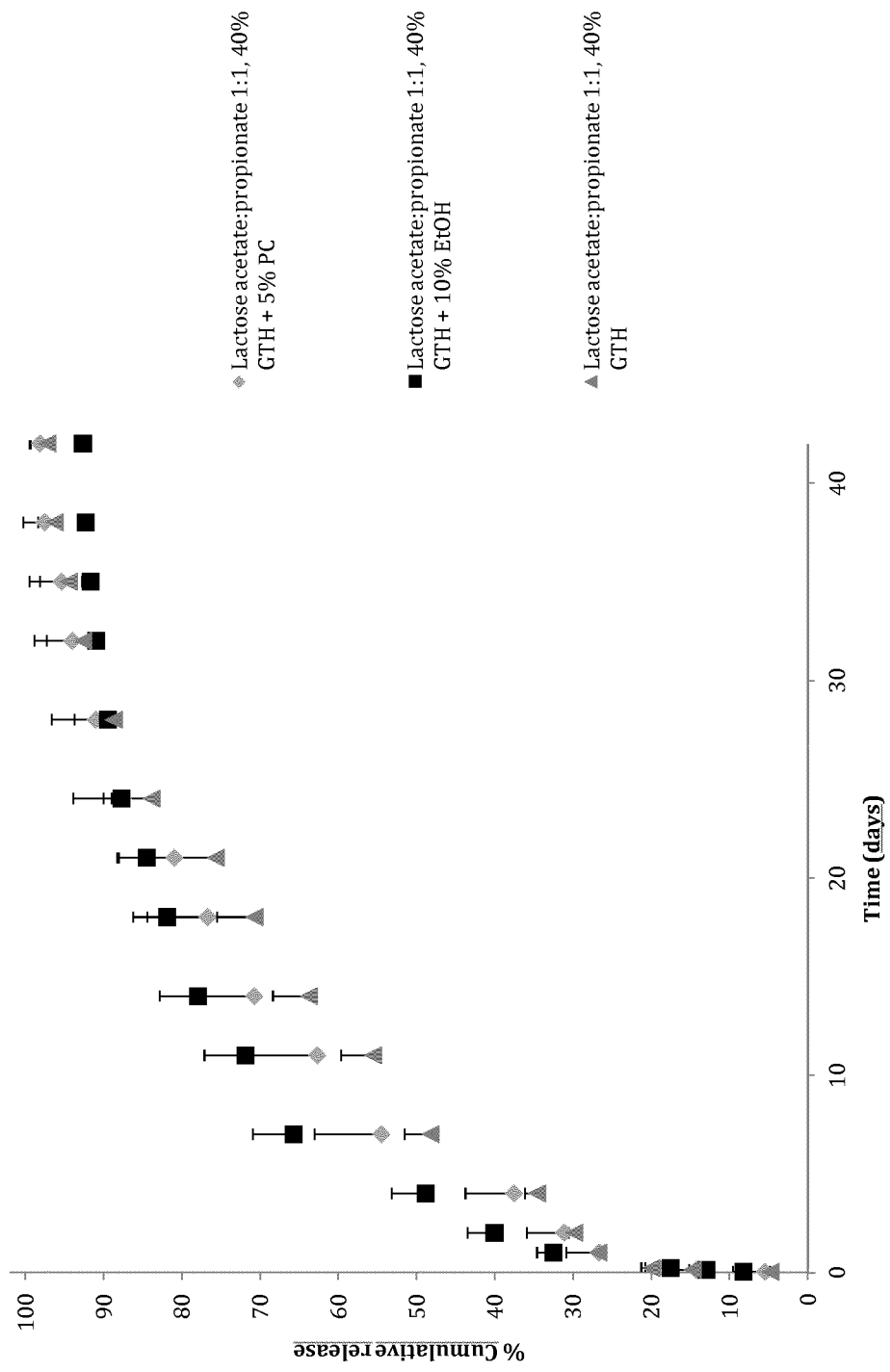
FIG. 25 a): Release of 5-FU from lactose acetate:propionate 1:1 or lactose isobutyrate-triglyceride formulations.

~400 mg of lactose isobutyrate or lactose acetate:propionate 1:1 was mixed with a 5-FU solution (in tBuOH/water) and freeze-dried overnight. The resultant carbohydrate-drug matrix was mixed with 40-50% triglyceride (glycerol trioctanoate (GTO) or glycerol trihexanoate (GTH)) tuning the formulations with 5-10% propylene carbonate/ethanol or 1-0.25% cellulose acetate butyrate (Mn ~12.000). This resulted in an average 5-FU concentration of ~30 µg/µL 5-FU in the gels. ~50 µL of the formulations were injected into PBS. Aliquots of 1 mL buffer were removed at specific time intervals and replaced with clean buffer. Cumulative release was measured by UV-vis at 265 nm (see FIG. 25 a and b).

Figure 26:
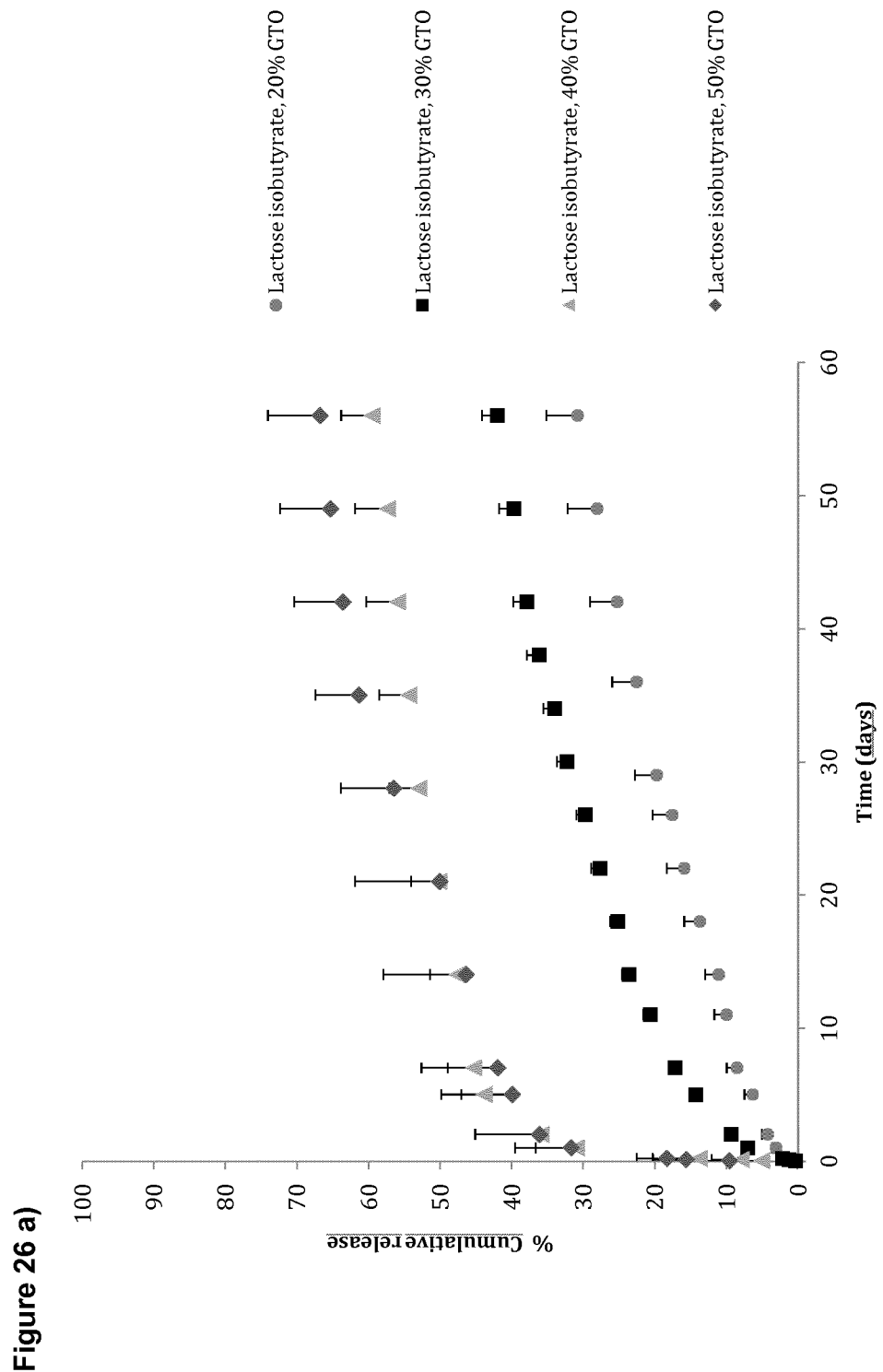
FIG. 26 a): Release from high concentration 5-FU lactose isobutyrate gel formulations.
Figure 26:
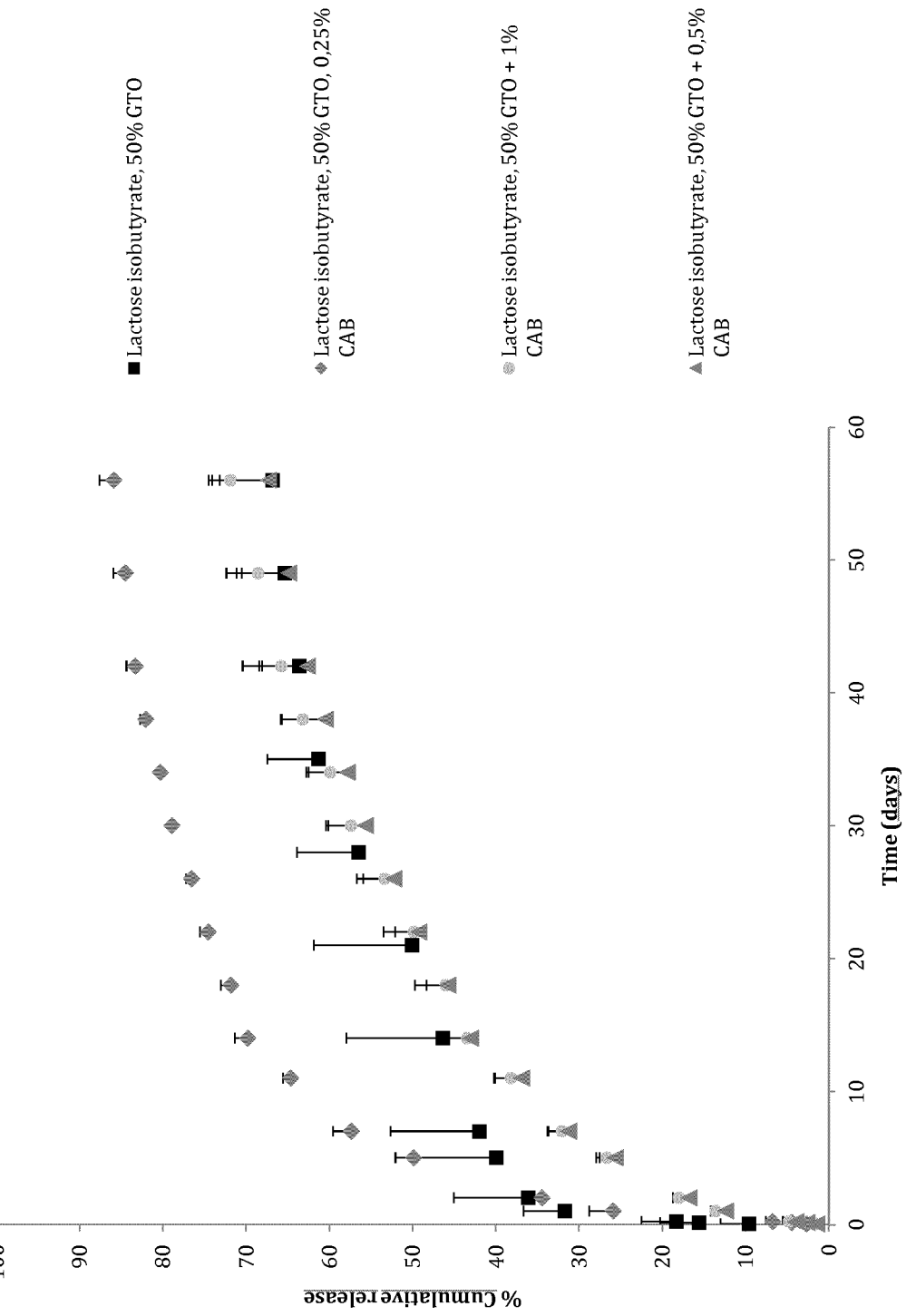
Figure 26:
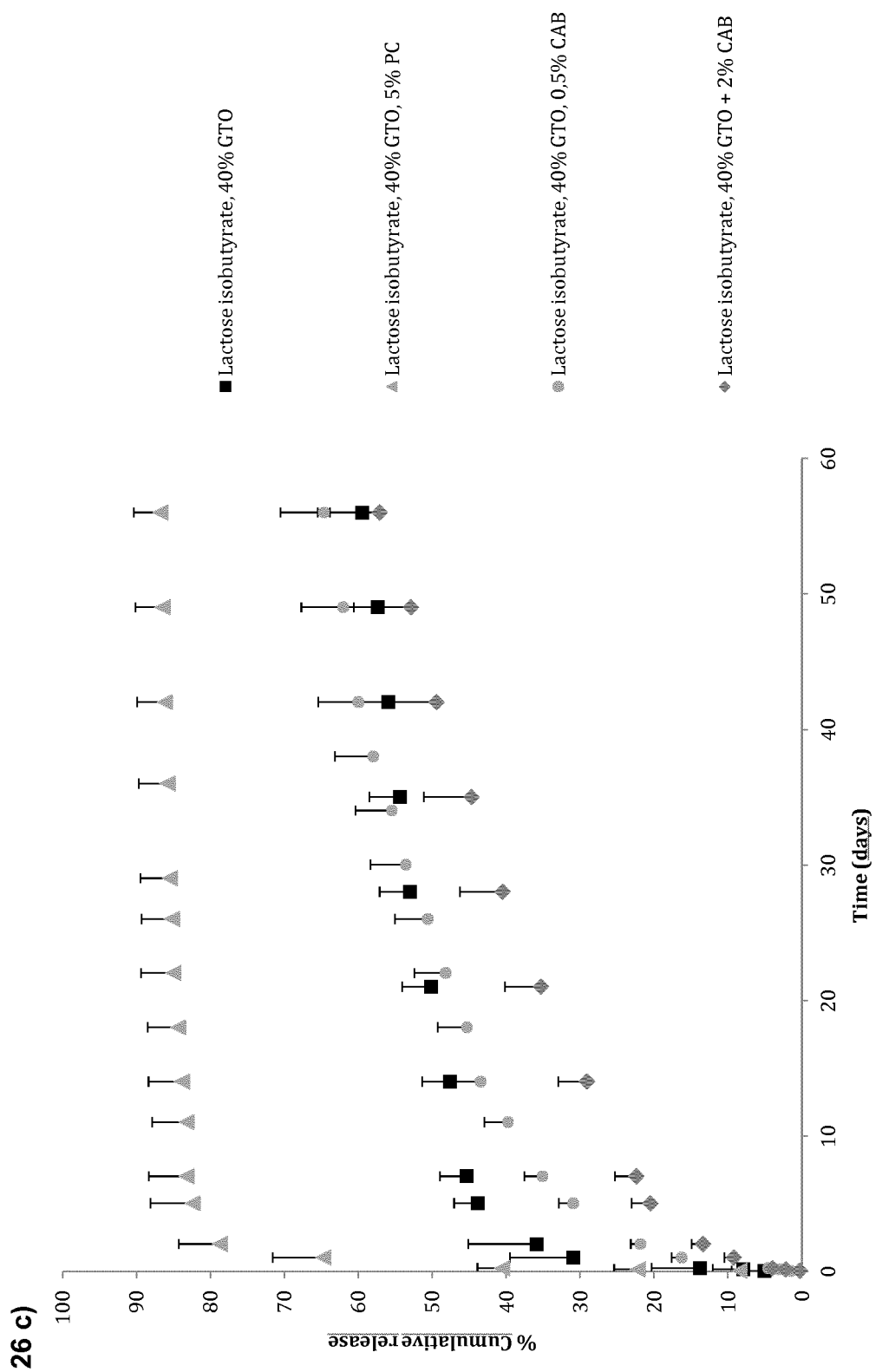
Figure 26:
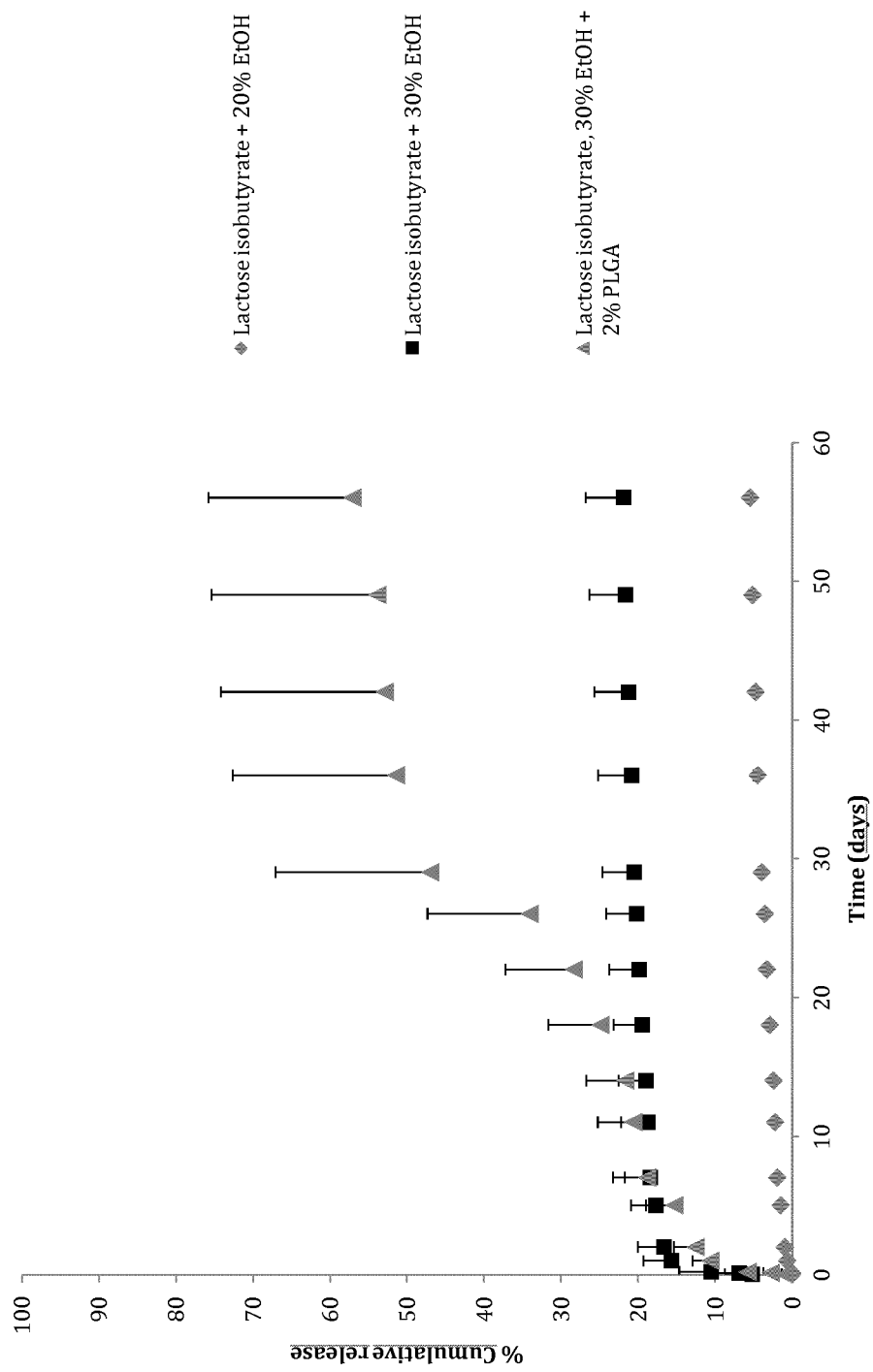
Figure 27:
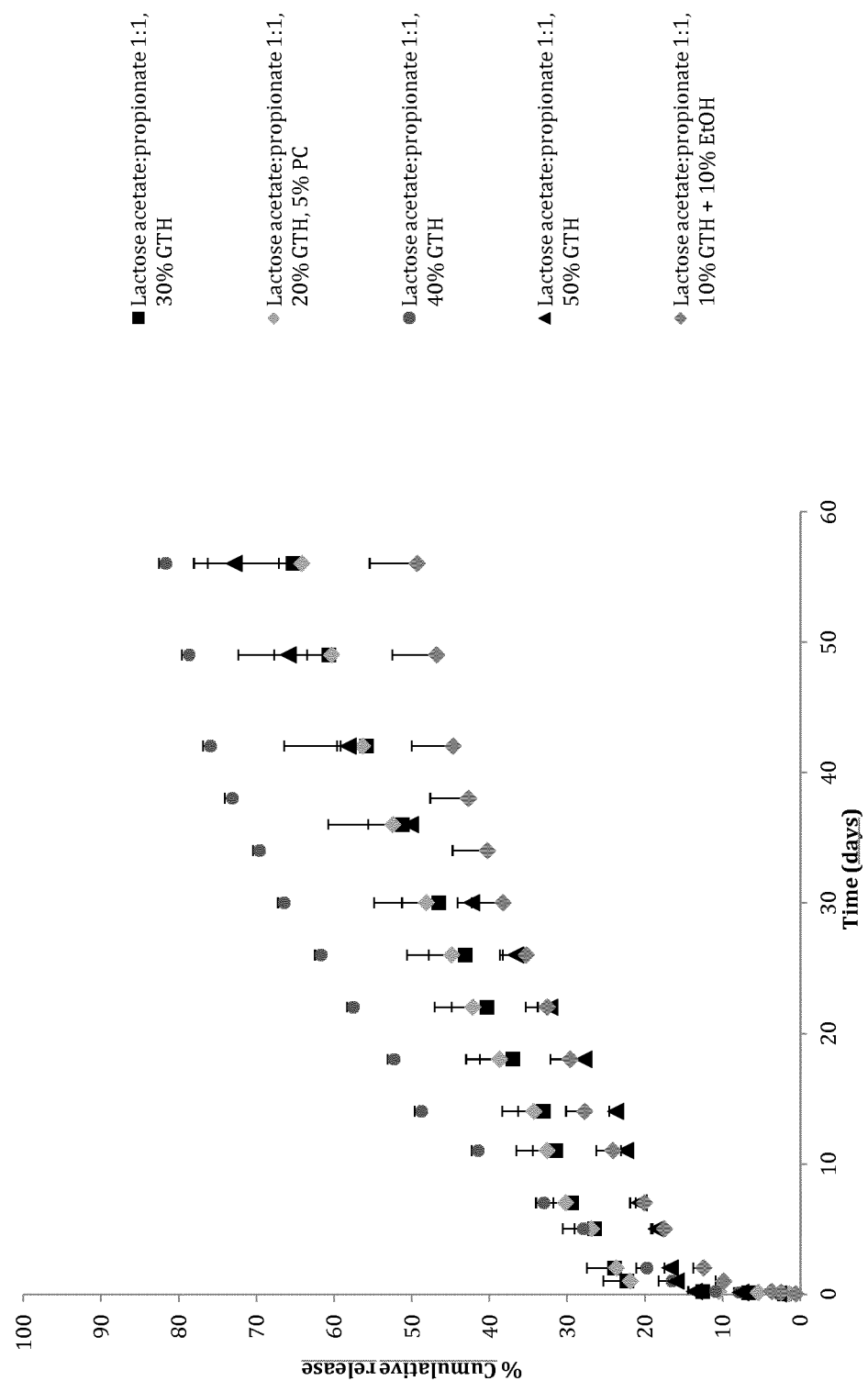
FIG. 27 a): Figure b+zoom are named b1) and b2). Text for all 4 figures: Release from high concentration 5-FU lactose acetate:propionate 1:1 gel formulations.
Figure 27:
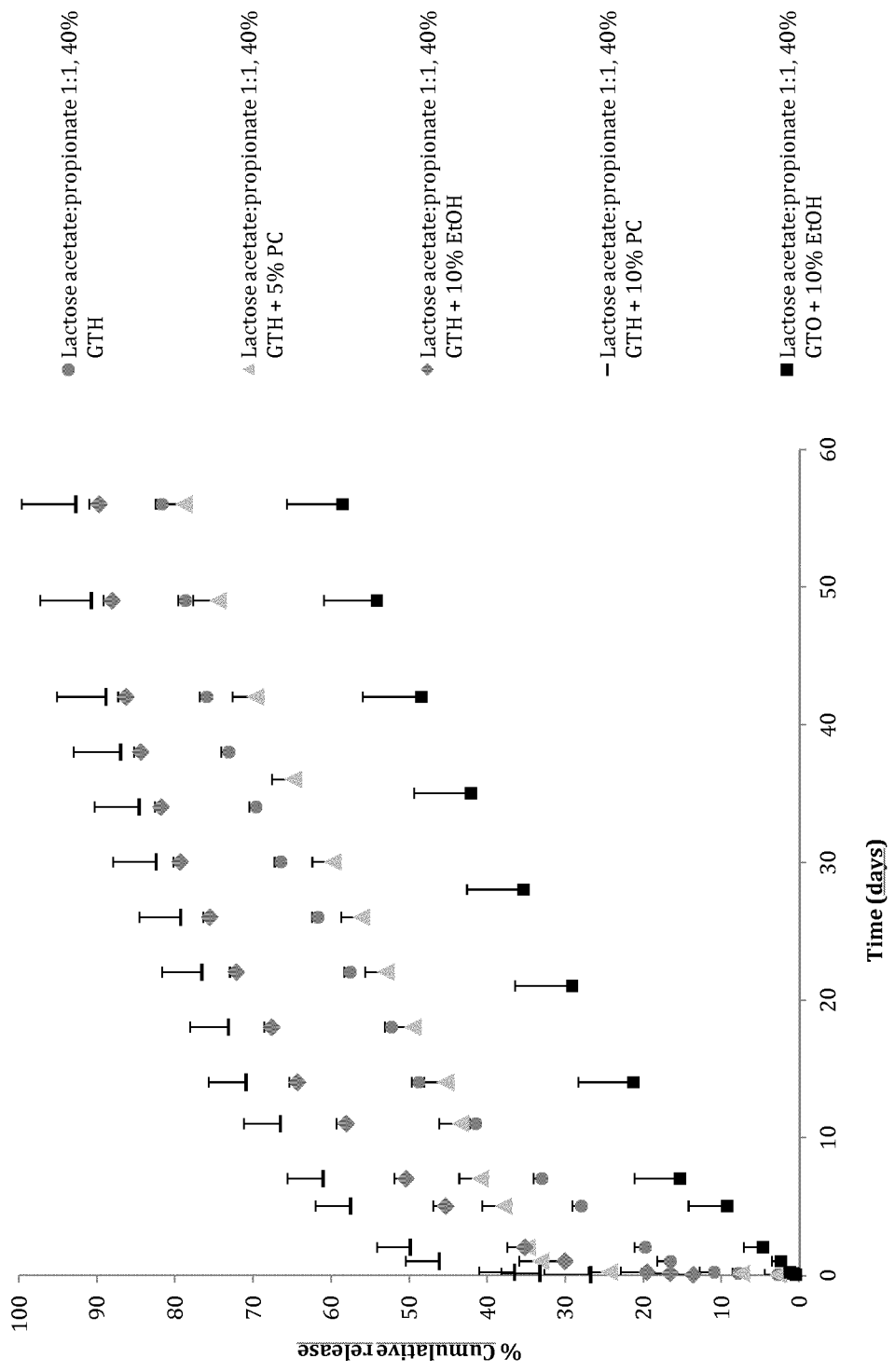

~400 mg of lactose isobutyrate or lactose acetate:propionate 1:1 was mixed with a 5-FU solution (in tBuOH/water) and freeze-dried overnight. The resultant carbohydrate-drug matrix was mixed with a) 10-50% triglyceride (glycerol trioctanoate (GTO) or glycerol trihexanoate (GTH)) tuning the formulations with 5-10% propylene carbonate/ethanol or 2-0.25% cellulose acetate butyrate (Mn ~12.000) or b) 20-30% propylene carbonate or ethanol, in case of EtOH with or without 2% PLGA (Mw 4000-15000). This resulted in an average 5-FU concentration of ~48 μg/μL 5-FU in the gels. ~50 μL of the formulations were injected into PBS. Aliquots of 1 mL buffer were removed at specific time intervals and replaced with clean buffer. Cumulative release was measured by UV-vis at 265 nm (see FIG. 26a, b, c and d+FIG. 27a, b, c and d).

Figure 28:
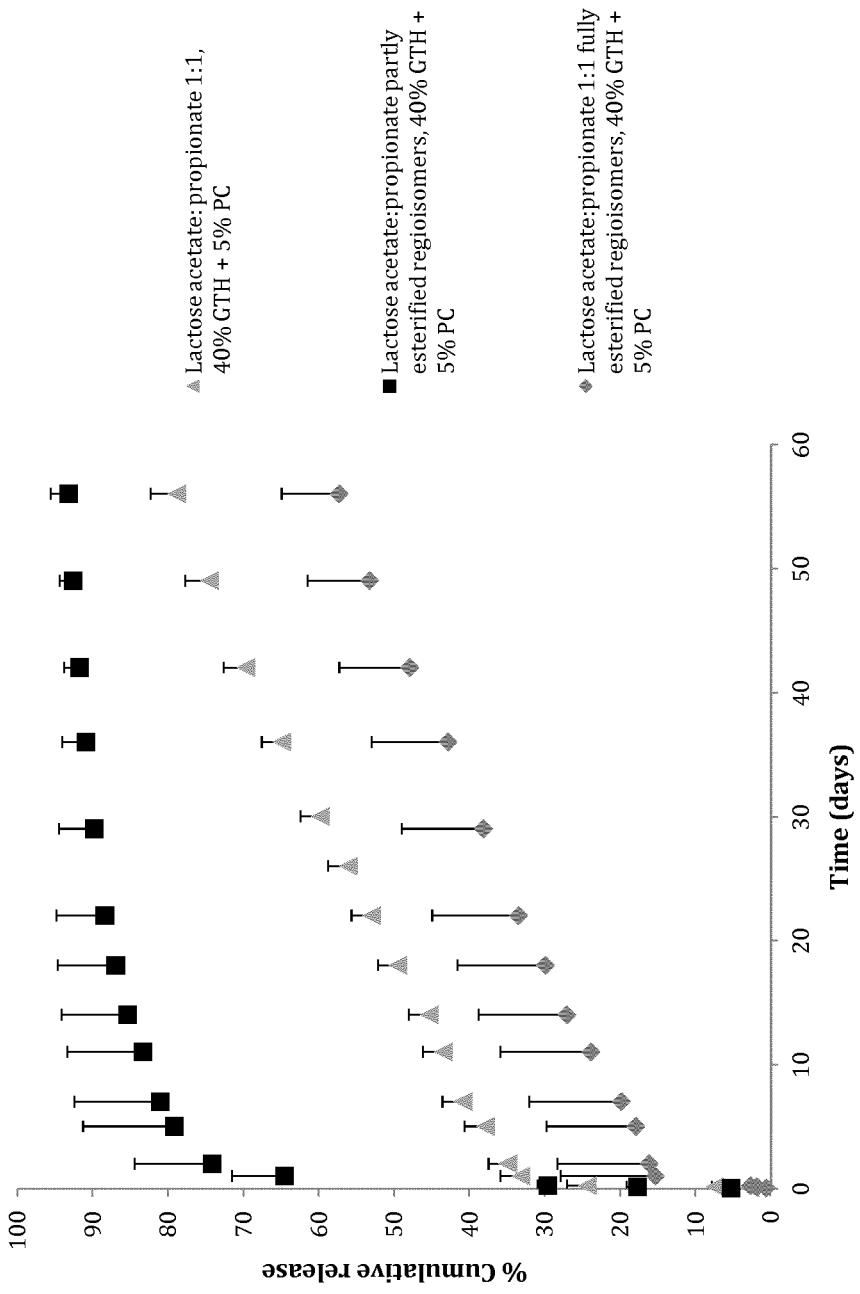
FIG. 28 a): Release of 5-FU from lactose acetate:propionate regioisomer-triglyceride/EtOH formulations.
Figure 28:
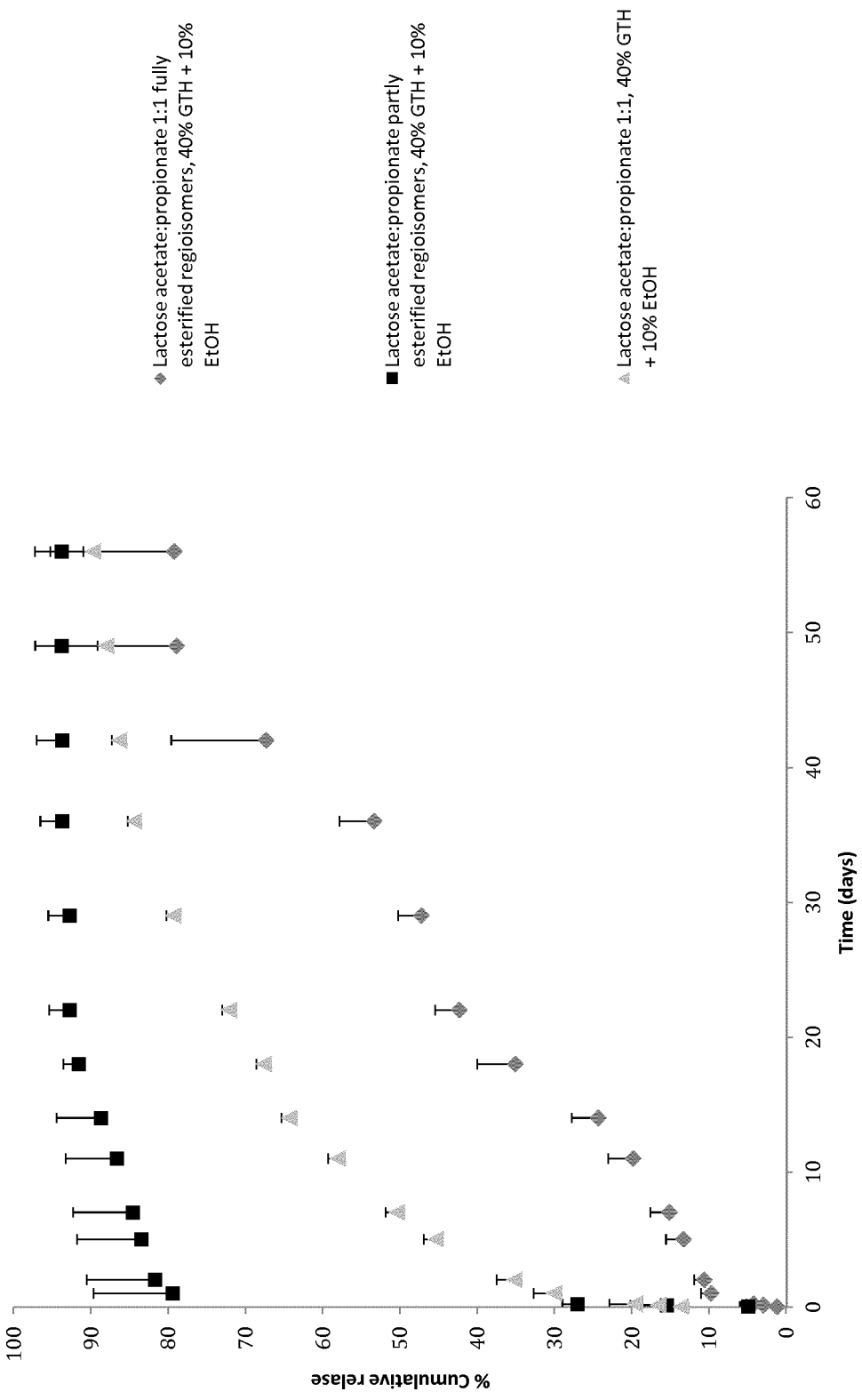
Figure 29:
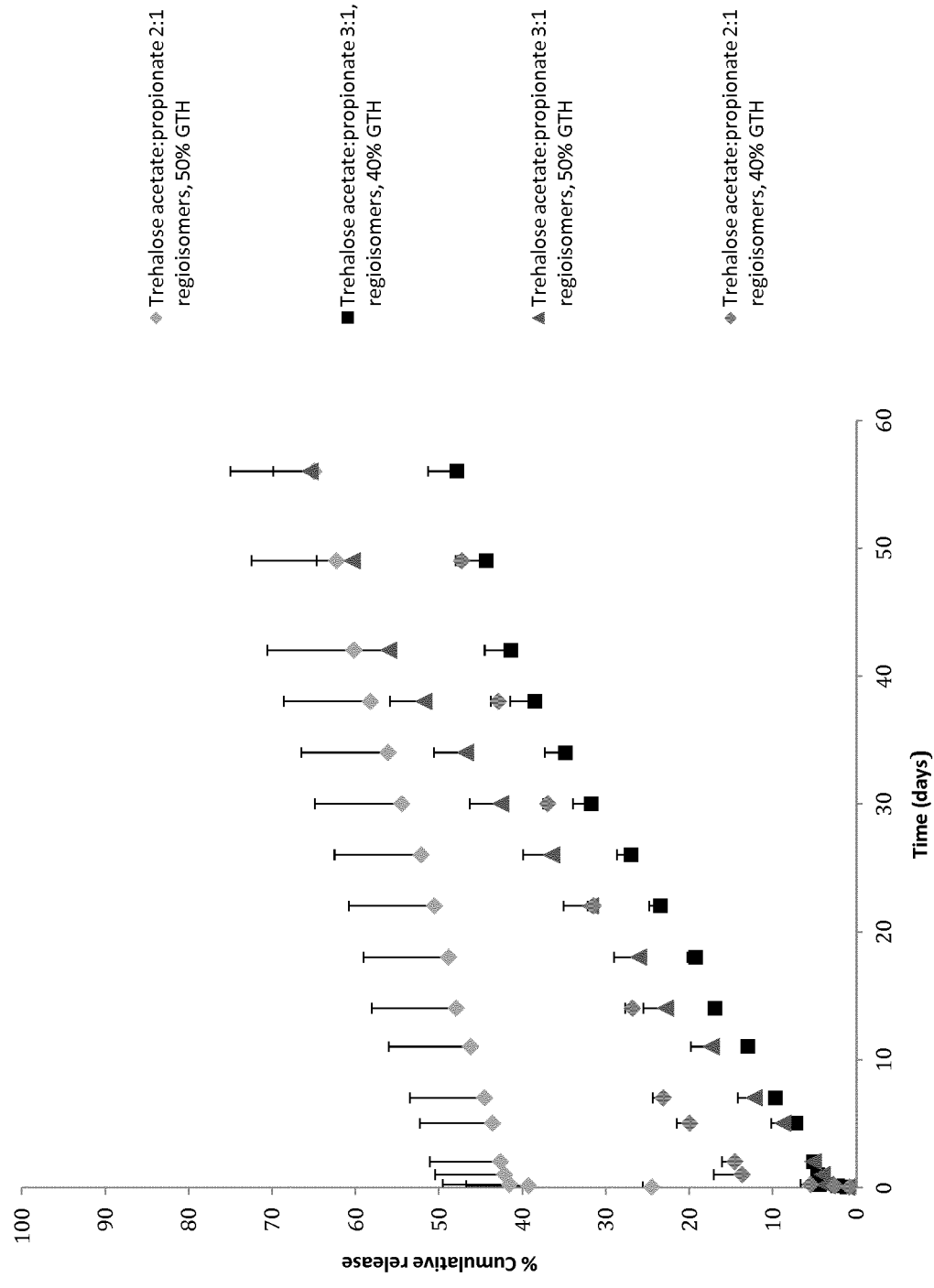
FIG. 29: Release of 5-FU from trehalose acetate:propionate regioisomer-triglyceride formulations.

~400 mg of lactose acetate:propionate 1:1 or lactose acetate:propionate regioisomers or trehalose acetate:propionate regioisomers were mixed with a 5-FU solution (in tBuOH/water) and freeze-dried overnight. The resultant carbohydrate-drug matrix was mixed with a) 40-50% triglyceride (glycerol trihexanoate (GTH)) tuning the formulations with 5-10% propylene carbonate/ethanol or b) 30% ethanol and 2% PLGA (Mw 4000-15000). This resulted in an average 5-FU concentration of ~48 μg/μL 5-FU in the gels. ~50 μL of the formulations were injected into PBS. Aliquots of 1 mL buffer were removed at specific time intervals and replaced with clean buffer. Cumulative release was measured by UV-vis at 265 nm. (FIG. 28 a, b and c+FIG. 29).

Example V

In Vivo Gel Stability Evaluation

Figure 18:
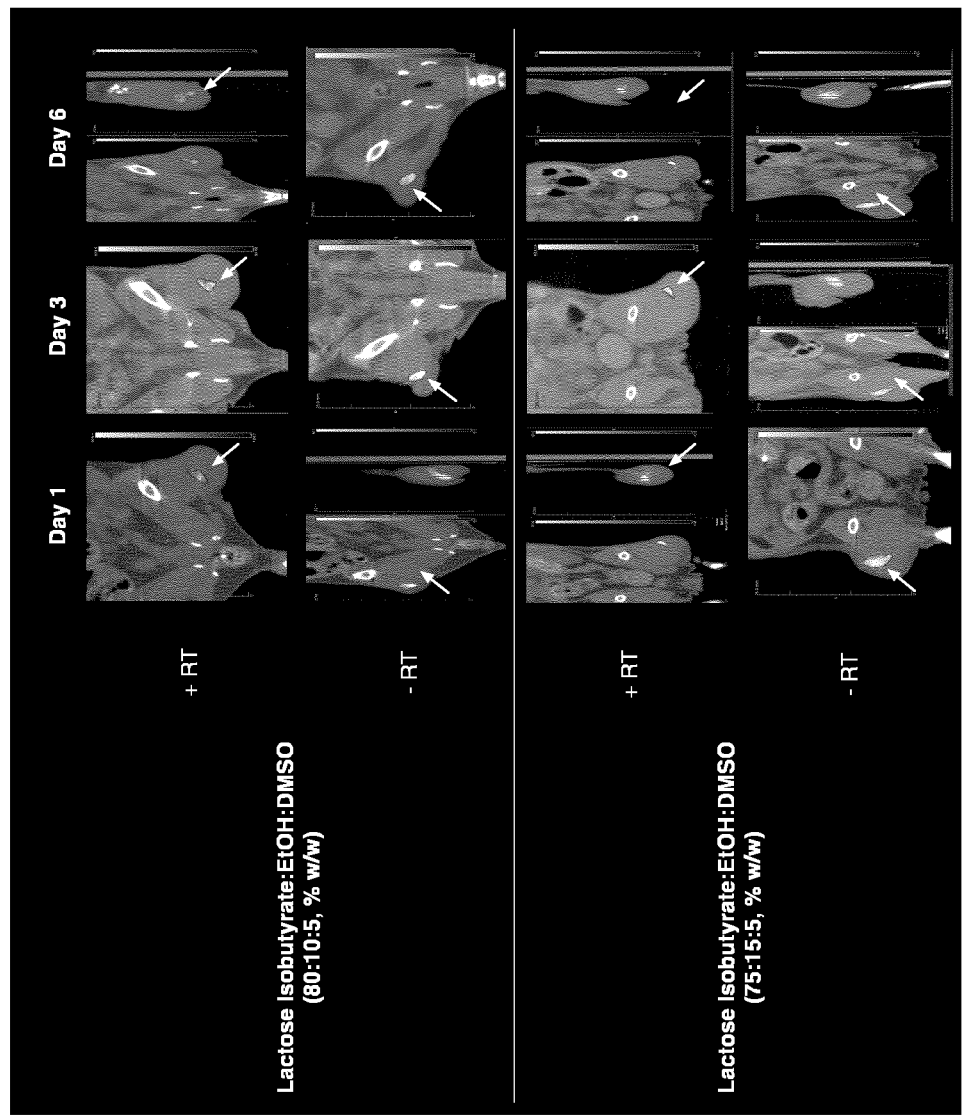
FIG. 18: In vivo gel stability evaluation of lactose isobutyrate gels by CT: CT-scans of mice injected with 25-30 uL of a lactose isobutyrate:IodoSAIB:EtOH 80:5:15 (% w/w) or a lactose isobutyrate:IodoSAIB:EtOH 75:5:20 (% w/w) gel formulation. The tumors treated with radiotherapy were exposed to three radiations of 5 gray each (day 2, day 3 and day 4 out of a period of 6 days). The white arrows indicate the location of the radiopaque gel-depots.
Figure 19:
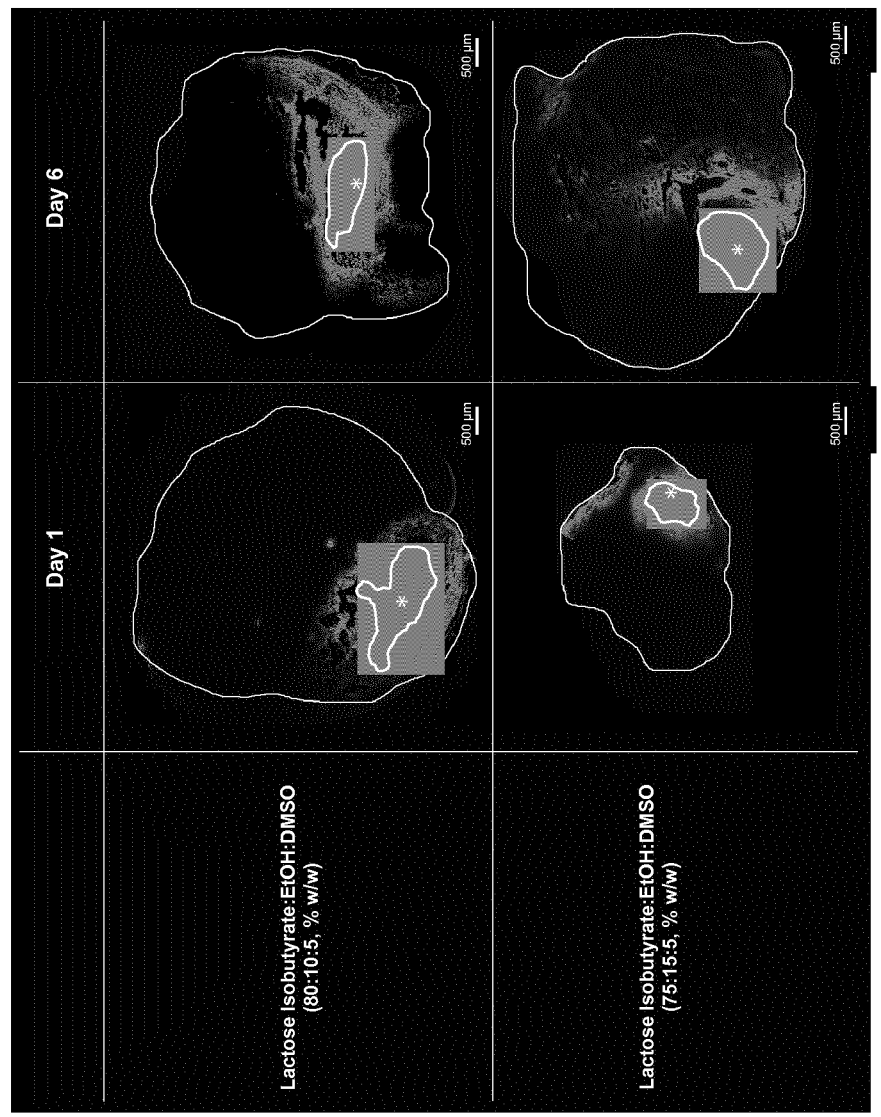
FIG. 19: Histological cross section of the tumor area showing diffusion of Hoechst 33342 from the lactose isobutyrate gel depots. These images represent cryo-sections made from tumors taken out at 1 day and day 6 post-injection. Intra-tumoral injection of the gel results in gaps in tumor sections as can also be seen in the image. The white line indicates the contour of the tumor section.

Formulations of lactose isobutyrate:X-SAIB (contrast agent): EtOH and DMSO with composition of 1)75:5:15:5, 2) 77, 5:5:12, 5:5 and 2) 80:5:10:5 were prepared along with formulations of lactose acetate:propionate(1:1):X-SAIB (contrast agent): EtOH and DMSO in 75:5:15:5 ratio. All of the gel formulations were prepared with ~0.7‰ of Hoechst 33342, as model of a DNA binding drug. 25-30 uL of each gel was injected into FaDu Head and Neck xenografts grown on the flank of NMRI nude mice (groups of 4-8 mice were injected with each formulation). Release and gel-stability was monitored for a maximum of 5-6 days. 2-3 mice were sacrificed at predetermined times (day 1, middle of the experimental period and at the end of the experimental period). The tumors were excised and snap-frozen with liquid $N_2$ to preserve the tumor tissue for histological examination. Stability of the radiopaque gel-depots was evaluated by micro-CT imaging (see FIG. 18). Only the lactose isobutyrate gel was subjected to X-rays, to evaluate the effect of radiation on gel-stability. Neither radiation nor the biological conditions in the tumor tissue seemed to significantly affect the gel stability, as the shape and size stayed relatively uniform over time. Diffusion of Hoechst was evaluated by fluorescent imaging of the tumor cryo-sections (see FIG. 19). Imaging confirmed release of Hoechst into the tumors, and showed distribution of the fluorophore across most of the tumor area over a period of 6 days.

Example VI

In Vivo Gel Efficacy Evaluation
Combination with Radiation Therapy

Figure 30A:
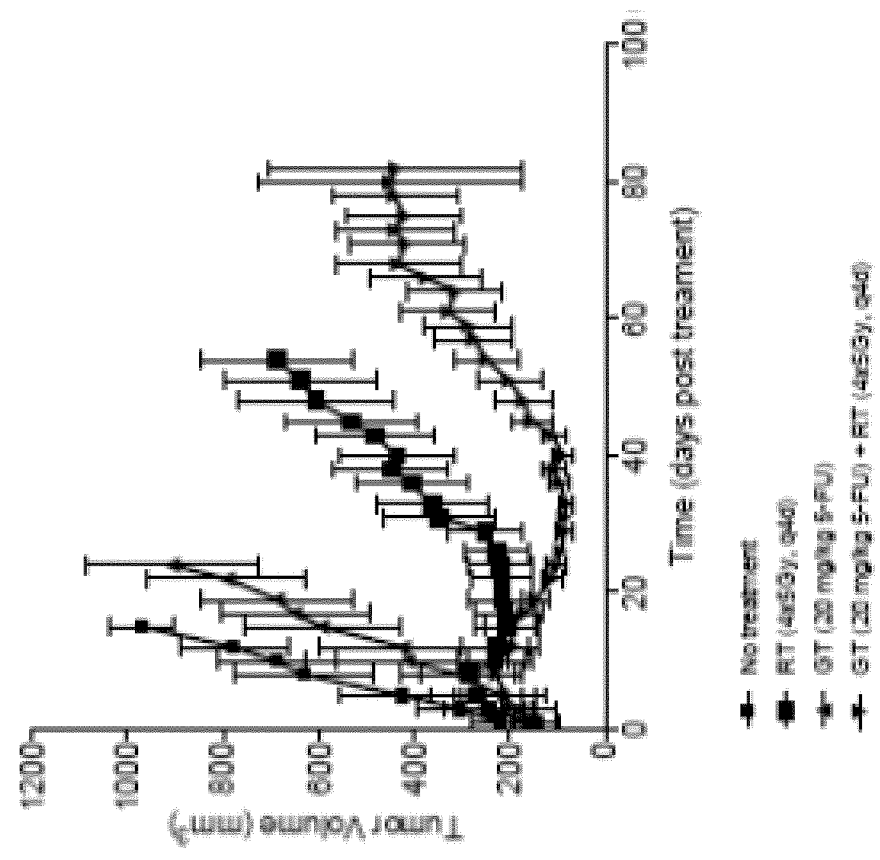
FIG. 30a: Tumor growth curve and survival from a Fadu Xenograft mouse model in vivo study with 5-FU release from Lactose isobutyrate:GTO formulations injected directly in tumor
Figure 30B:
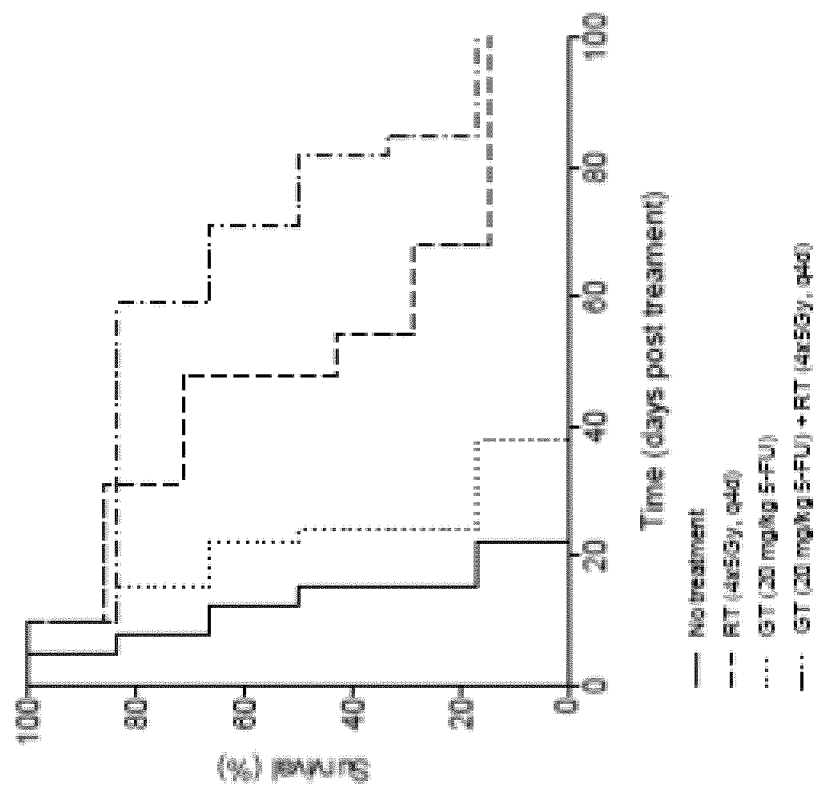
FIG. 30b: Tumor growth curve and survival from a Fadu Xenograft mouse model in vivo study with 5-FU release from Lactose isobutyrate:GTO formulations injected directly in tumor
Figure 31A:
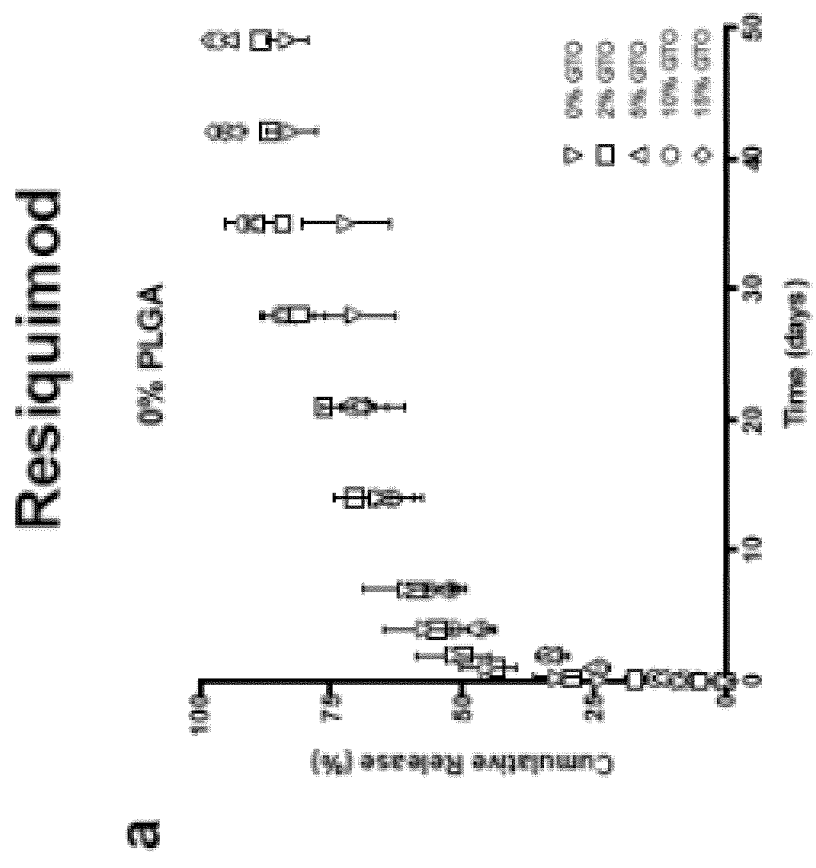
FIG. 31a: Cumulative release, Resiquimod
Figure 31B:
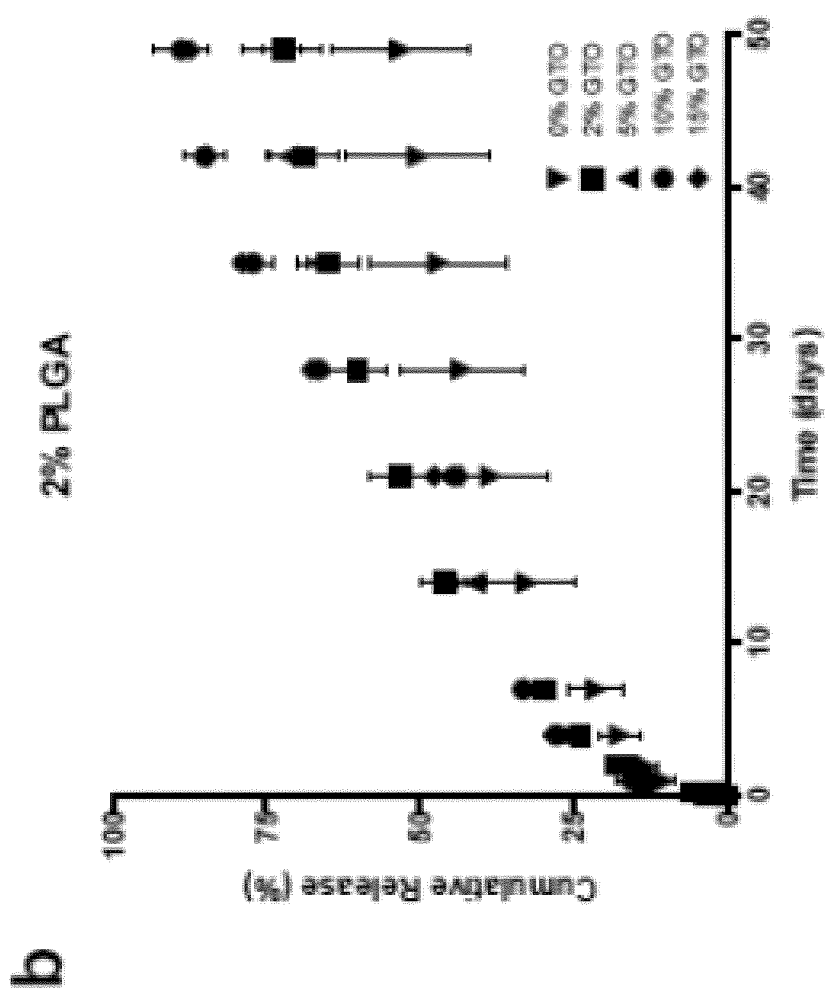
FIG. 31b: Cumulative release, Resiquimod
Figure 31C:
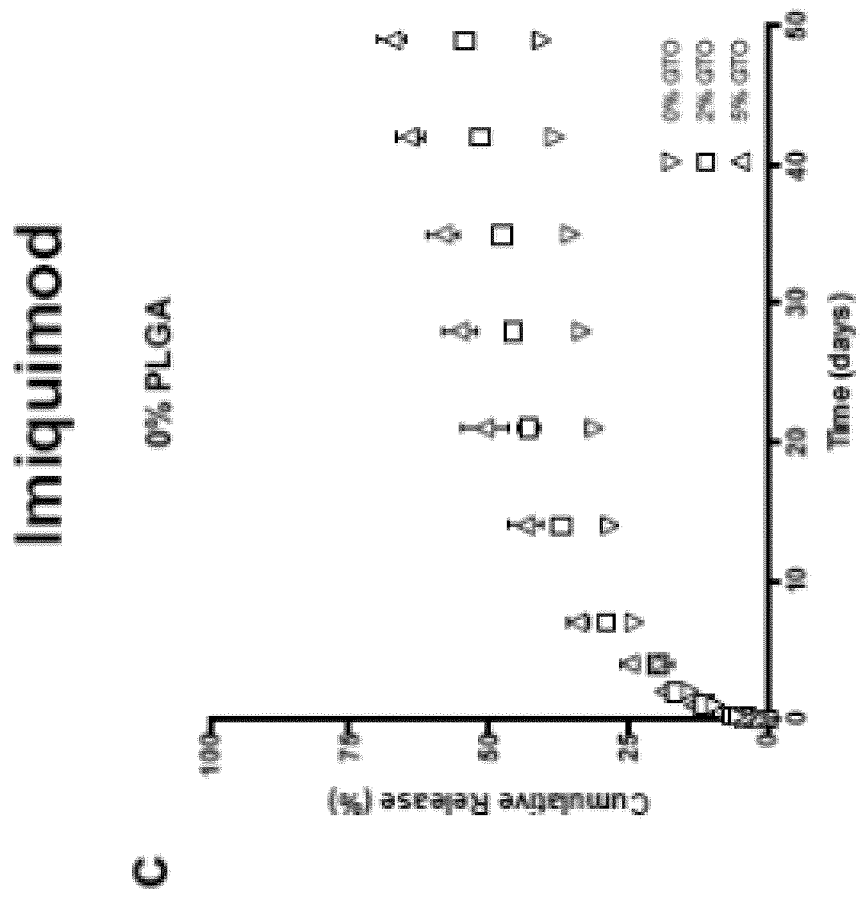
FIG. 31c: Cumulative release, Imiquimod
Figure 31D:
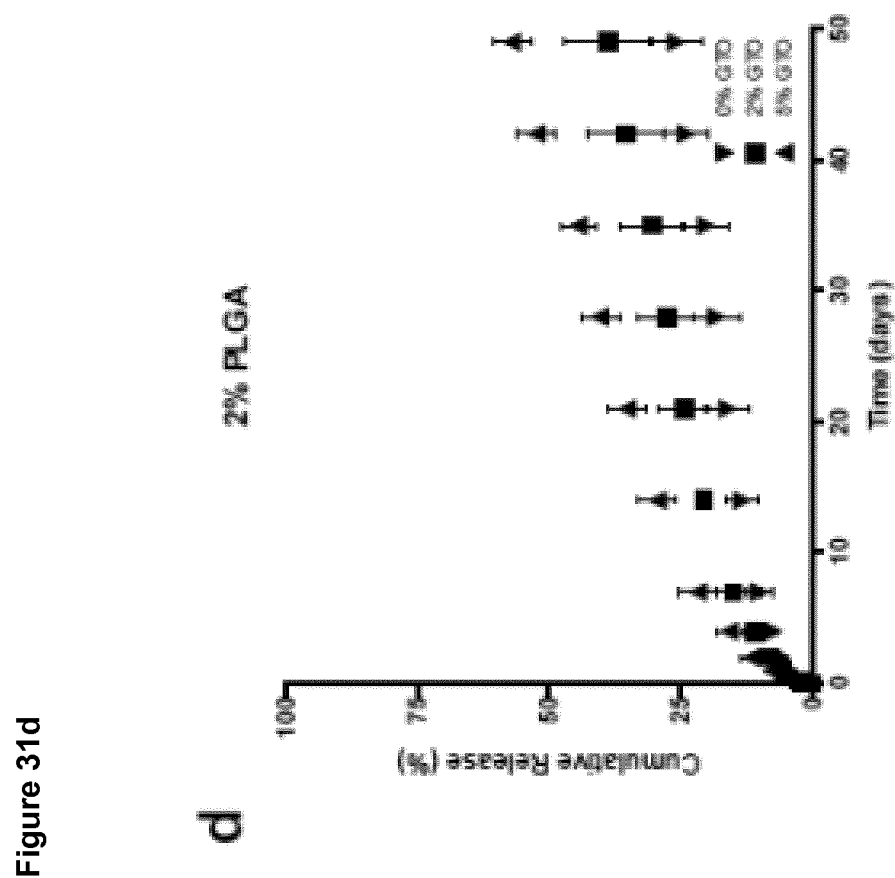
FIG. 31d: Cumulative release, Imiquimod

Lactose isobutyrate:GTO with composition 60:40 w/w % was prepared with 22.4 μg/μL 5-fluoruracil. 25 μL gel (5-FU dose per mouse: 20 mg/kg) was injected intratumoral into Fadu Head and Neck xenograft tumors (average tumor size: 150-200 mm3) subcutaneously grown on the flank of nude NMRI mice, at a flow rate of 5 μl/minute. On day 1 after gel injection, the tumors were subjected to radiation therapy (4 times 5 Gy on day 1, 4, 7 and 10). Each group consisted of 7-8 mice and the tumor growth progression was monitored 3 times a week. The mice were euthanized once their tumors had exceeded 1000 mm3. During the same period, weight of individual mice was monitored to observe the safety profile. (see FIG. 30, a: tumor growth curve, b: survival curve).

The invention claimed is:

1. A composition comprising non-water soluble carbohydrates and at least one triglyceride, wherein at least 50% of the non-water soluble carbohydrates are carbohydrates selected from derivatives of lactose, maltose, trehalose, or mixtures thereof, and wherein the composition is a liquid before administration into the human or animal body and increases in viscosity by more than 1,000 centipoise (cP) after administration to form a gel, wherein the non-water soluble carbohydrates are saccharides which are modified with hydrophobic moieties to provide a water-excluding gel forming component that is promoted by hydrophobic interactions and/or physical non-covalent cross-links, wherein the liquid composition is homogenous and gelled composition is homogenous in appearance, for use as a medicament for drug delivery as a controlled release system of an active pharmaceutical ingredient in a human or animal body, and wherein the active pharmaceutical ingredient is a drug that modulates an immune response, wherein said at least one triglyceride is arranged in an amount of 10-50 wt % of the composition wherein the non-water soluble carbohydrates are disaccharides with structures selected from

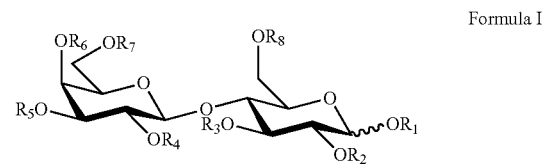

Formula I

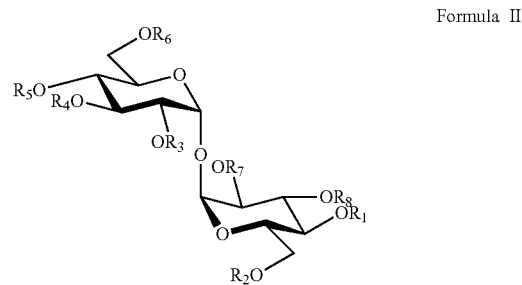

Formula II

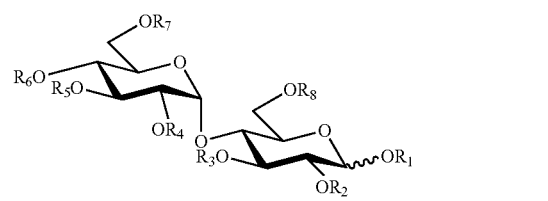

Formula III wherein R1, R2, R3, R4, R5, R6, R7, and R8 in formulae I, II and III are selected collectively from the group consisting of hydrogen, alkanoyl, hydroxyl-substituted alkanoyl, and acyloxy-substituted alkanoyl, alkanyl, hydroxysubstituted alkanyl and acyloxy substituted alkanyl; or wherein R1, R2, R3, R4, R5, R6, R7, and R8 are independently selected from the group consisting of hydrogen, alkanoyl, hydroxyl-substituted alkanoyl, and acyloxy-substituted alkanoyl, alkanyl, hydroxysubstituted alkanyl and acyloxy substituted alkanyl;
or wherein all groups of R1, R2, R3, R4, R5, R6, R7, and R8 are selected collectively from the group consisting of acetyl, isobutyryl or propionyl; or wherein R1, R2, R3, R4, R5, R6, R7, and R8 are independently selected from the group consisting acetyl, isobutyryl or propionyl; and wherein both pure anomers and mixtures of α- and β-anomers of the above mentioned structural variations are claimed.

2. The composition according to claim 1, wherein the composition is a liquid before administration into the human or animal body that increases in viscosity by more than 10,000 centipoise (cP) after administration into the human or animal body.

3. The composition according to claim 1, wherein the composition is a liquid before administration and transform into a gel like material after administration.

4. The composition according to claim 1, wherein the composition becomes a solid after administration, such as a crystalline or amorphous solid.

5. The composition according to claim 1, wherein an increase in viscosity after administration into the human or animal body is due to diffusion of a molecule out of the administered material and into surrounding tissue.

6. The composition according to claim 1, wherein an increase in viscosity after administration into the human or animal body is due to diffusion of solvent-like molecules.

7. The composition according to claim 1, wherein the release of one or more active pharmaceutical ingredients is controlled by mixing nonwater soluble carbohydrates with different hydrophobicity by alteration of the substitutions on the carbohydrate hydroxyl groups.

8. The composition according to claim 1, wherein the active pharmaceutical ingredient is selected from a protein, a peptide, a nucleoprotein, a mucoprotein, a lipoprotein, or a synthetic polypeptide.

9. The composition according to claim 1, wherein the active pharmaceutical ingredient is selected from a protein, which is a human growth hormone, fibroblast growth factor (FGF), erythropoietin (EPO), platelet derived growth factor (PDGF), granulocyte colony stimulating factor (g-CSF), bovine somatotropin (BST), tumor necrosis factor (TNF), transforming growth factor-beta (TGF-Beta), a cytokine, an interleukin, insulin, or interferon.

10. The composition according to claim 1, wherein the active pharmaceutical ingredient is selected from nucleic acids, nucleotides, nucleosides, oligonucleotides, DNA, RNA or fragments thereof.

11. The composition according to claim 1, wherein the active pharmaceutical ingredient is a small inorganic or organic drug molecule.

12. The composition according to claim 1, wherein the active pharmaceutical ingredient is a chemotherapeutic drug for treatment of cancer.

13. The composition according to claim 1, wherein the active pharmaceutical ingredients is a chemotherapeutic drug selected from the class of compounds that are anti-metabolites, anti-microtubule agents, topoisomerase inhibitors, cytotoxic antibiotics, alkylating agents, checkpoint inhibitors, or a radiosensitizer, or a photosensitizer.

14. The composition according to claim 1, wherein the active pharmaceutical ingredient enhances the effect of radiotherapy, photodynamic therapy (PDT), hyperthermia based treatments such as high-intensity focused ultrasound (HIFU), radiofrequency thermal ablation (RFA), laser-therapy, or laser-induced interstitial thermotherapy (LITT).

15. The composition according to claim 1, wherein the active pharmaceutical ingredient is an anesthetic.

16. The composition according to claim 1, wherein the active pharmaceutical ingredient is formulated in a nanoparticle or microsphere that is dispersed in the composition.

17. The composition according to claim 1, wherein the composition comprises contrast agents that makes the composition visible by PET imaging, SPECT imaging, Ultrasound imaging, CT imaging, x-ray imaging, fluoroscopy imaging, fluorescence imaging, or OCT imaging.

18. The composition according to claim 1, wherein the composition comprises organic radioisotopes or inorganic radionuclides for use as internal radiotherapy such as brachytherapy or in imaging of tissue in humans or animals.

19. The composition according to claim 1, wherein the composition contains an active pharmaceutical ingredient that is a TLR7 or TLR8 agonist, or wherein the compositions contains an active pharmaceutical ingredient that is a TLR7 or TLR8 agonist and at least one more active pharmaceutical ingredient that modulates an immune response.

20. The composition according to claim 1, wherein the composition contains an active pharmaceutical ingredient that is a TLR7 or TLR8 agonist, or wherein the compositions contains an active pharmaceutical ingredient that is a TLR7 or TLR8 agonist and at least one more active pharmaceutical ingredient that is a chemotherapeutic agent.

21. The composition according to claim 1, wherein the composition comprises resiquimod and/or imiquimod.

* * * * *